US008834900B2

(12) United States Patent
Krieg et al.

(10) Patent No.: US 8,834,900 B2
(45) Date of Patent: Sep. 16, 2014

(54) COMBINATION MOTIF IMMUNE STIMULATORY OLIGONUCLEOTIDES WITH IMPROVED ACTIVITY

(75) Inventors: Arthur M. Krieg, Wellesley, MA (US); Jorg Vollmer, Duesseldorf (DE)

(73) Assignees: University of Iowa Research Foundation, Iowa City, IA (US); Coley Pharmaceutical GmbH, Düsseldorf (DE)

( * ) Notice: Subject to any disclaimer, the term of this patent is extended or adjusted under 35 U.S.C. 154(b) by 1536 days.

(21) Appl. No.: 10/224,523

(22) Filed: Aug. 19, 2002

(65) Prior Publication Data

US 2003/0148976 A1 Aug. 7, 2003

Related U.S. Application Data

(60) Provisional application No. 60/313,273, filed on Aug. 17, 2001, provisional application No. 60/393,952, filed on Jul. 3, 2002.

(51) Int. Cl.
*A61K 45/00* (2006.01)
*C07H 21/02* (2006.01)

(52) U.S. Cl.
USPC ........................................ 424/278.1; 536/23.1

(58) Field of Classification Search
USPC ........................................... 514/44; 435/375
See application file for complete search history.

(56) References Cited

U.S. PATENT DOCUMENTS

| | | | |
|---|---|---|---|
| 3,854,480 A | 12/1974 | Zaffaroni et al. |
| 4,452,775 A | 6/1984 | Kent |
| 4,469,863 A | 9/1984 | Ts'o et al. |
| 4,675,189 A | 6/1987 | Kent et al. |
| 4,806,463 A | 2/1989 | Goodchild et al. |
| 4,925,793 A | 5/1990 | Goeddel et al. |
| 5,004,810 A | 4/1991 | Draper |
| 5,023,243 A | 6/1991 | Tullis |
| 5,133,974 A | 7/1992 | Paradissis et al. |
| 5,166,195 A | 11/1992 | Ecker |
| 5,194,428 A | 3/1993 | Agrawal et al. |
| 5,264,423 A | 11/1993 | Cohen et al. |
| 5,276,019 A | 1/1994 | Cohen et al. |
| 5,407,686 A | 4/1995 | Patel et al. |
| 5,457,189 A | 10/1995 | Crooke et al. |
| 5,475,096 A | 12/1995 | Gold et al. |
| 5,514,577 A | 5/1996 | Draper et al. |
| 5,514,788 A | 5/1996 | Bennett et al. |
| 5,576,208 A | 11/1996 | Monia et al. |
| 5,582,986 A | 12/1996 | Monia et al. |
| 5,587,361 A | 12/1996 | Cook et al. |
| 5,594,122 A | 1/1997 | Friesen |
| 5,663,153 A | 9/1997 | Hutcherson et al. |
| 5,670,637 A | 9/1997 | Gold et al. |
| 5,684,147 A | 11/1997 | Agrawal et al. |
| 5,696,249 A | 12/1997 | Gold et al. |
| 5,723,335 A | 3/1998 | Hutcherson et al. |
| 5,736,152 A | 4/1998 | Dunn |
| 5,780,448 A | 7/1998 | Davis |
| 5,843,653 A | 12/1998 | Gold et al. |
| 5,877,309 A | 3/1999 | McKay et al. |
| 5,932,556 A | 8/1999 | Tam |
| 5,977,340 A | 11/1999 | Pirotzky et al. |
| 6,030,955 A | 2/2000 | Stein et al. |
| 6,184,369 B1 | 2/2001 | Rando et al. |
| 6,194,388 B1 | 2/2001 | Krieg et al. |
| 6,207,646 B1 | 3/2001 | Krieg et al. |
| 6,214,806 B1 | 4/2001 | Krieg et al. |
| 6,218,371 B1 | 4/2001 | Krieg et al. |
| 6,221,882 B1 | 4/2001 | Macfarlane |
| 6,239,116 B1 | 5/2001 | Krieg et al. |
| 6,339,068 B1 | 1/2002 | Krieg et al. |
| 6,399,630 B1 | 6/2002 | Macfarlane |
| 6,406,705 B1 | 6/2002 | Davis et al. |
| 6,426,334 B1 | 7/2002 | Agrawal et al. |
| 6,429,199 B1 | 8/2002 | Krieg et al. |
| 6,479,504 B1 | 11/2002 | Macfarlane et al. |
| 6,498,147 B2 | 12/2002 | Nerenberg et al. |
| 6,498,148 B1 | 12/2002 | Raz |
| 6,503,533 B1 | 1/2003 | Korba et al. |

(Continued)

FOREIGN PATENT DOCUMENTS

| | | |
|---|---|---|
| EP | 092574 A1 | 4/1983 |
| EP | 0 302 758 A1 | 2/1989 |
| EP | 0 468 520 A2 | 1/1992 |
| RU | 2107728 C1 | 3/1998 |
| WO | WO 90/08777 A | 8/1990 |
| WO | WO 91/12811 A1 | 9/1991 |
| WO | WO 92/03456 A1 | 3/1992 |
| WO | WO 94/01550 A1 | 1/1994 |
| WO | WO 94/19945 A1 | 9/1994 |
| WO | WO 95/03407 A2 | 2/1995 |

(Continued)

OTHER PUBLICATIONS

Krieg A. M. BioDrugs, 5:341-346, 1998.*
Agrawal et al. Trends in Mol. Med., 8:114-121, 2002.*
Ballas ZK et al. (1996) *J Immunol* 157:1840-5.
Beaucage SL et al. (1981) *Tetrahedron Lett* 22:1859.
Cella M et al. (1999) *Nat Med* 5:919-23.
Cohen PA et al. (1994) *Cancer Res* 54:1055-8.
Crooke ST et al. (1996) *Annu Rev Pharmacol Toxicol* 36:107-129.
Froehler BC et al. (1986) *Nucl Acid Res* 14:5399-407.
Froehler BC et al. (1992) *J. Am Chem Soc* 114:8320.
Gaffney BL et al. (1988) *Tetrahedron Lett* 29:2619-22.

(Continued)

*Primary Examiner* — Patricia A Duffy
(74) *Attorney, Agent, or Firm* — Wolf, Greenfield & Sacks, P.C.

(57) ABSTRACT

A class of immunostimulatory nucleic acids having at least two functionally and structurally defined domains is provided. This class of combination motif immunostimulatory nucleic acids activates an immune response and is useful for treating a variety of immune related disorders such as cancer, infectious disease, and allergic disorders. The nucleic acids also stimulate activation of natural killer cells and production of type 1 interferon.

28 Claims, 29 Drawing Sheets

(56) References Cited

U.S. PATENT DOCUMENTS

| | | |
|---|---|---|
| 6,521,637 B2 | 2/2003 | Macfarlane |
| 6,558,670 B1 | 5/2003 | Friede et al. |
| 6,589,940 B1 | 7/2003 | Raz et al. |
| 6,610,308 B1 | 8/2003 | Haensler |
| 6,610,661 B1 | 8/2003 | Carson et al. |
| 6,653,292 B1 | 11/2003 | Krieg et al. |
| 6,727,230 B1 | 4/2004 | Hutcherson et al. |
| 6,821,957 B2 | 11/2004 | Krieg et al. |
| 6,835,395 B1 | 12/2004 | Semple et al. |
| 6,943,240 B2 | 9/2005 | Bauer et al. |
| 6,949,520 B1 | 9/2005 | Hartmann et al. |
| 6,977,245 B2 | 12/2005 | Klinman et al. |
| 7,001,890 B1 | 2/2006 | Wagner et al. |
| 7,223,741 B2 | 5/2007 | Krieg |
| 7,271,156 B2 | 9/2007 | Krieg et al. |
| 7,354,711 B2 | 4/2008 | Macfarlane |
| 7,402,572 B2 | 7/2008 | Krieg et al. |
| 7,410,975 B2 | 8/2008 | Lipford et al. |
| 7,488,490 B2 | 2/2009 | Davis et al. |
| 7,795,235 B2 | 9/2010 | Krieg et al. |
| 2001/0021772 A1 | 9/2001 | Uhlmann et al. |
| 2001/0044416 A1 | 11/2001 | Davis et al. |
| 2002/0064515 A1 | 5/2002 | Krieg et al. |
| 2002/0065236 A1 | 5/2002 | Yew et al. |
| 2002/0091097 A1 | 7/2002 | Bratzler et al. |
| 2002/0156033 A1 | 10/2002 | Bratzler et al. |
| 2002/0164341 A1 | 11/2002 | Davis et al. |
| 2002/0165178 A1 | 11/2002 | Schetter et al. |
| 2002/0192184 A1 | 12/2002 | Carpentier et al. |
| 2002/0198165 A1 | 12/2002 | Bratzler et al. |
| 2003/0026782 A1 | 2/2003 | Krieg et al. |
| 2003/0026801 A1 | 2/2003 | Weiner et al. |
| 2003/0049266 A1 | 3/2003 | Fearon et al. |
| 2003/0050261 A1 | 3/2003 | Krieg et al. |
| 2003/0050263 A1 | 3/2003 | Krieg et al. |
| 2003/0050268 A1 | 3/2003 | Krieg et al. |
| 2003/0055014 A1 | 3/2003 | Bratzler |
| 2003/0060440 A1 | 3/2003 | Klinman et al. |
| 2003/0064945 A1 | 4/2003 | Akhtar et al. |
| 2003/0087848 A1 | 5/2003 | Bratzler et al. |
| 2003/0091599 A1 | 5/2003 | Davis et al. |
| 2003/0100527 A1 | 5/2003 | Krieg et al. |
| 2003/0104523 A1 | 6/2003 | Lipford et al. |
| 2003/0119773 A1 | 6/2003 | Raz et al. |
| 2003/0125279 A1 | 7/2003 | Junghans et al. |
| 2003/0133988 A1 | 7/2003 | Fearon et al. |
| 2003/0139364 A1 | 7/2003 | Krieg et al. |
| 2003/0148316 A1 | 8/2003 | Lipford et al. |
| 2003/0148976 A1 | 8/2003 | Krieg et al. |
| 2003/0166001 A1 | 9/2003 | Lipford |
| 2003/0175731 A1 | 9/2003 | Fearon et al. |
| 2003/0181406 A1 | 9/2003 | Schetter et al. |
| 2003/0191079 A1 | 10/2003 | Krieg et al. |
| 2003/0199466 A1 | 10/2003 | Fearon et al. |
| 2003/0212026 A1 | 11/2003 | Krieg et al. |
| 2003/0224010 A1 | 12/2003 | Davis et al. |
| 2003/0232074 A1 | 12/2003 | Lipford et al. |
| 2003/0232856 A1 | 12/2003 | Macfarlane |
| 2004/0006034 A1 | 1/2004 | Raz et al. |
| 2004/0009949 A1 | 1/2004 | Krieg |
| 2004/0030118 A1 | 2/2004 | Wagner et al. |
| 2004/0038922 A1 | 2/2004 | Haensler et al. |
| 2004/0047869 A1 | 3/2004 | Garcon et al. |
| 2004/0053880 A1 | 3/2004 | Krieg |
| 2004/0067902 A9 | 4/2004 | Bratzler et al. |
| 2004/0067905 A1 | 4/2004 | Krieg |
| 2004/0087534 A1 | 5/2004 | Krieg et al. |
| 2004/0087538 A1 | 5/2004 | Krieg et al. |
| 2004/0092468 A1 | 5/2004 | Schwartz et al. |
| 2004/0092472 A1 | 5/2004 | Krieg |
| 2004/0106568 A1 | 6/2004 | Krieg et al. |
| 2004/0131628 A1 | 7/2004 | Bratzler et al. |
| 2004/0132685 A1 | 7/2004 | Krieg et al. |
| 2004/0142469 A1 | 7/2004 | Krieg et al. |
| 2004/0143112 A1 | 7/2004 | Krieg et al. |
| 2004/0147468 A1 | 7/2004 | Krieg et al. |
| 2004/0152649 A1 | 8/2004 | Krieg |
| 2004/0152656 A1 | 8/2004 | Krieg et al. |
| 2004/0152657 A1 | 8/2004 | Krieg et al. |
| 2004/0162258 A1 | 8/2004 | Krieg et al. |
| 2004/0162262 A1 | 8/2004 | Krieg et al. |
| 2004/0167089 A1 | 8/2004 | Krieg et al. |
| 2004/0171150 A1 | 9/2004 | Krieg et al. |
| 2004/0171571 A1 | 9/2004 | Krieg et al. |
| 2004/0181045 A1 | 9/2004 | Krieg et al. |
| 2004/0198680 A1 | 10/2004 | Krieg |
| 2004/0198688 A1 | 10/2004 | Krieg et al. |
| 2004/0229835 A1 | 11/2004 | Krieg et al. |
| 2004/0234512 A1 | 11/2004 | Wagner et al. |
| 2004/0235770 A1 | 11/2004 | McCluskie et al. |
| 2004/0235774 A1 | 11/2004 | Bratzler et al. |
| 2004/0235777 A1 | 11/2004 | Wagner et al. |
| 2004/0235778 A1 | 11/2004 | Wagner et al. |
| 2004/0247662 A1 | 12/2004 | Dow et al. |
| 2004/0266719 A1 | 12/2004 | McCluskie et al. |
| 2005/0004061 A1 | 1/2005 | Krieg et al. |
| 2005/0004062 A1 | 1/2005 | Krieg et al. |
| 2005/0009774 A1 | 1/2005 | Krieg et al. |
| 2005/0031638 A1 | 2/2005 | Dalemans et al. |
| 2005/0032734 A1 | 2/2005 | Davis et al. |
| 2005/0032736 A1 | 2/2005 | Krieg et al. |
| 2005/0037403 A1 | 2/2005 | Krieg et al. |
| 2005/0037985 A1 | 2/2005 | Krieg et al. |
| 2005/0043529 A1 | 2/2005 | Davis et al. |
| 2005/0049215 A1 | 3/2005 | Krieg et al. |
| 2005/0049216 A1 | 3/2005 | Krieg et al. |
| 2005/0054601 A1 | 3/2005 | Wagner et al. |
| 2005/0054602 A1 | 3/2005 | Krieg et al. |
| 2005/0059619 A1 | 3/2005 | Krieg et al. |
| 2005/0059625 A1 | 3/2005 | Krieg et al. |
| 2005/0070491 A1 | 3/2005 | Krieg et al. |
| 2005/0075302 A1 | 4/2005 | Hutcherson et al. |
| 2005/0100983 A1 | 5/2005 | Bauer et al. |
| 2005/0101554 A1 | 5/2005 | Krieg et al. |
| 2005/0101557 A1 | 5/2005 | Krieg et al. |
| 2005/0119273 A1 | 6/2005 | Lipford et al. |
| 2005/0123523 A1 | 6/2005 | Krieg et al. |
| 2005/0130911 A1 | 6/2005 | Uhlmann et al. |
| 2005/0148537 A1 | 7/2005 | Krieg et al. |
| 2005/0152921 A1 | 7/2005 | Kim et al. |
| 2005/0169888 A1 | 8/2005 | Hartman et al. |
| 2005/0171047 A1 | 8/2005 | Krieg et al. |
| 2005/0181422 A1 | 8/2005 | Bauer et al. |
| 2005/0182017 A1 | 8/2005 | Krieg |
| 2005/0197314 A1 | 9/2005 | Krieg et al. |
| 2005/0203039 A1 | 9/2005 | Jeon et al. |
| 2005/0209184 A1 | 9/2005 | Klinman et al. |
| 2005/0215501 A1 | 9/2005 | Lipford et al. |
| 2005/0233995 A1 | 10/2005 | Krieg et al. |
| 2005/0233999 A1 | 10/2005 | Krieg et al. |
| 2005/0239732 A1 | 10/2005 | Krieg et al. |
| 2005/0239733 A1 | 10/2005 | Jurk et al. |
| 2005/0239734 A1 | 10/2005 | Uhlmann et al. |
| 2005/0239736 A1 | 10/2005 | Krieg et al. |
| 2005/0244379 A1 | 11/2005 | Krieg et al. |
| 2005/0244380 A1 | 11/2005 | Krieg et al. |
| 2005/0245477 A1 | 11/2005 | Krieg et al. |
| 2005/0250726 A1 | 11/2005 | Krieg et al. |
| 2005/0256073 A1 | 11/2005 | Lipford et al. |
| 2005/0267064 A1 | 12/2005 | Krieg et al. |
| 2005/0277604 A1 | 12/2005 | Krieg et al. |
| 2005/0277609 A1 | 12/2005 | Krieg et al. |
| 2006/0003955 A1 | 1/2006 | Krieg et al. |
| 2006/0003962 A1 | 1/2006 | Ahluwalia et al. |
| 2006/0019916 A1 | 1/2006 | Krieg et al. |
| 2006/0019923 A1 | 1/2006 | Davis et al. |
| 2006/0058251 A1 | 3/2006 | Krieg et al. |
| 2006/0058254 A1 | 3/2006 | Dina et al. |
| 2006/0089326 A1 | 4/2006 | Krieg et al. |
| 2006/0094683 A1 | 5/2006 | Krieg et al. |
| 2006/0140875 A1 | 6/2006 | Krieg et al. |
| 2006/0154890 A1 | 7/2006 | Bratzler et al. |
| 2006/0172966 A1 | 8/2006 | Lipford et al. |
| 2006/0188913 A1 | 8/2006 | Krieg et al. |

(56) References Cited

U.S. PATENT DOCUMENTS

| | | |
|---|---|---|
| 2006/0211639 A1 | 9/2006 | Bratzler et al. |
| 2006/0211644 A1 | 9/2006 | Krieg et al. |
| 2006/0229271 A1 | 10/2006 | Krieg et al. |
| 2006/0241076 A1 | 10/2006 | Uhlmann et al. |
| 2006/0246035 A1 | 11/2006 | Ahluwalia et al. |
| 2006/0286070 A1 | 12/2006 | Hartmann et al. |
| 2006/0287263 A1 | 12/2006 | Davis et al. |
| 2007/0009482 A9 | 1/2007 | Krieg et al. |
| 2007/0010470 A9 | 1/2007 | Krieg et al. |
| 2007/0037767 A1 | 2/2007 | Bratzler et al. |
| 2007/0065467 A1 | 3/2007 | Krieg et al. |
| 2007/0066553 A1 | 3/2007 | Krieg et al. |
| 2007/0066554 A1 | 3/2007 | Krieg et al. |
| 2007/0078104 A1 | 4/2007 | Krieg et al. |
| 2007/0129320 A9 | 6/2007 | Davis et al. |
| 2007/0142315 A1 | 6/2007 | Forsbach et al. |
| 2007/0184465 A1 | 8/2007 | Wagner et al. |
| 2007/0202128 A1 | 8/2007 | Krieg et al. |
| 2007/0224210 A1 | 9/2007 | Krieg et al. |
| 2007/0232622 A1 | 10/2007 | Lipford et al. |
| 2008/0009455 A9 | 1/2008 | Krieg et al. |
| 2008/0026011 A1 | 1/2008 | Krieg et al. |
| 2008/0031936 A1 | 2/2008 | Krieg et al. |
| 2008/0045473 A1 | 2/2008 | Uhlmann et al. |
| 2008/0113929 A1 | 5/2008 | Lipford et al. |
| 2008/0226649 A1 | 9/2008 | Schetter et al. |
| 2009/0060927 A1 | 3/2009 | Wagner et al. |

FOREIGN PATENT DOCUMENTS

| | | |
|---|---|---|
| WO | WO 96/02555 A1 | 2/1996 |
| WO | WO 98/18810 A1 | 5/1998 |
| WO | WO 98/29430 A1 | 7/1998 |
| WO | WO 98/32462 A1 | 7/1998 |
| WO | WO 98/37919 A1 | 9/1998 |
| WO | WO 98/40100 A1 | 9/1998 |
| WO | WO 98/49288 A1 | 11/1998 |
| WO | WO 98/52581 A1 | 11/1998 |
| WO | WO 98/52962 A1 | 11/1998 |
| WO | WO 99/50297 A1 | 10/1999 |
| WO | WO 99/51259 A2 | 10/1999 |
| WO | WO 99/56755 A1 | 11/1999 |
| WO | WO 99/58118 A2 | 11/1999 |
| WO | WO 99/61056 A2 | 12/1999 |
| WO | WO 99/61056 A3 | 12/1999 |
| WO | WO 99/63975 A2 | 12/1999 |
| WO | WO 00/06588 A1 | 2/2000 |
| WO | WO 00/14217 A2 | 3/2000 |
| WO | WO 00/14217 A3 | 3/2000 |
| WO | WO 00/61151 A2 | 10/2000 |
| WO | WO 00/67023 A1 | 11/2000 |
| WO | WO 00/67787 A2 | 11/2000 |
| WO | WO 00/75304 A1 | 12/2000 |
| WO | WO 01 22972 A2 | 4/2001 |
| WO | WO 01/22990 A2 | 4/2001 |
| WO | WO 01/22990 A3 | 4/2001 |
| WO | WO 01/35991 A2 | 5/2001 |
| WO | WO 01/45750 A1 | 6/2001 |
| WO | WO 01/55370 A2 | 8/2001 |
| WO | WO 01/62909 A1 | 8/2001 |
| WO | WO 01 95935 A1 | 12/2001 |
| WO | WO 01/97843 A2 | 12/2001 |
| WO | WO 02/22809 A2 | 3/2002 |
| WO | WO 02/053141 A2 | 7/2002 |
| WO | WO 02/069369 A2 | 9/2002 |
| WO | WO 03/012061 A2 | 2/2003 |
| WO | WO 03/015711 A2 | 2/2003 |
| WO | WO 03/031573 A2 | 4/2003 |
| WO | WO 2004/007743 A2 | 1/2004 |
| WO | WO 2004/026888 A2 | 4/2004 |
| WO | WO 2004/094671 A2 | 11/2004 |
| WO | WO 2007/075626 A2 | 7/2007 |
| WO | WO 2008/030455 A2 | 3/2008 |
| WO | WO 2008/033432 A2 | 3/2008 |
| WO | WO 2008/039538 A2 | 4/2008 |
| WO | WO 2008/068638 A2 | 6/2008 |
| WO | WO 2008/139262 A2 | 11/2008 |

OTHER PUBLICATIONS

Garegg PJ et al. (1986) *Tetrahedron Lett* 27:4051-4.
Garegg PJ et al. (1986) *Tetrahedron Lett* 27:4055-8.
Goodchild J (1990) *Bioconjugate Chem* 1:165.
Grouard G et al. (1997) *J Exp Med* 185:1101-11.
Jahrsdoerfer B et al. "CpG DNA Increases Primary Malignant B Cell Expression of Costimulatory Molecules and Target Antigens." *J. of Leukocyte Biology, Federation of American Societies for Experimental*, US. vol. 1, No. 69, Jan. 2001: pp. 81-88.
Krieg AM et al., "Applications of Immune Stimulatory CpG DNA for Antigen-Specific and Antigen-Nonspecific Cancer Immunotherapy" *European Journal of Cancer*. Pergamon Press, Oxford. vol. 35. No. Suppl. 5. 1999: p. S10.
Krieg AM (2001) *Trends Microbiol* 9:249-52.
Krieg AM et al. (1995) *Nature* 374:546-9.
Krieg AM et al. (1998) *Proc Natl Acad Sci USA* 95:12631-12636.
Krieg. AM et al. *Vaccine* (2001) 19:618-622.
Langer R (1990) *Science* 249:1527-33.
Loetscher P et al. (2001) *J Biol Chem* 276:2986-91.
National Institutes of Health: Guidelines for the Diagnosis and Management of Asthma, Expert Panel Report 2. NIH Publication No. 97/4051. Jul. 19. 1997.
Nielsen PE et al. (1994) *Bioconjug Chem* 5:3-7.
Rissoan M-C et al. (1999) *Science* 283:1183-6.
Siegal FP et al. (1999) *Science* 284.1835-7.
Stirchak EP et al. (1989) *Nucleic Acids Res* 17:6129-41.
Tarkov M et al. (1993) *Helv Chim Acta* 76 481.
Uhlmann E et al. (1990) *Chem Rev* 90:544.
Vandendriessche F et al. (1993) *Tetrahedron* 49:7223.
Wagner RW et al. (1996) *Nat Biotechnol* 14:840-4.
Warren TL et al. "CpC, oligodeoxynucleotides enhance monoclonal antibody therapy of a murine lymphoma." *Clinical Lymphoma* vol. 1. No. 1. Jun. 2000. pp. 57-61.
Yamamoto S et al. (1992) *J Immunol* 148:4072-6.
Chatellier S et al., Preferential stimulation of human lymphocytes by oligodeoxynucleotides that copy DNA CpG motifs present in virulent genes of group A streptococci, *Eur J Immunol*. Apr. 2000;30(4):993-1001.
Pisetsky D et al., Influence of backbone chemistry on immune activation by synthetic oligonucleotides, *Biochem Pharmacol*. Dec. 15, 1999;58(12):1981-8.
Hartmann G et al., Delineation of a CpG phosphorothioate oligodeoxynucleotide for activating primate immune responses in vitro and in vivo. *J Immunol*. Feb. 1, 2000;164(3):1617-24.
Agrawal et al., In vivo pharmacokinetics of phosphorothioate oligonucleotides containing contiguous guanosines. Antisense Nucleic Acid Drug Dev. Jun. 1997;7(3):245-9.
Agrawal et al., Antisense therapeutics: is it as simple as complementary base recognition? Mol Med Today. Feb. 2000;6(2):72-81.
Agrawal et al., Chapter 19: Pharmacokinetics and bioavailability of antisense oligonucleotides following oral and colorectal administrations in experimental animals. 1998: 525-43.
Agrawal et al., Antisense oligonucleotides: towards clinical trials. Trends in Biotechnology, 1996; 14: 376-87.
Ballas et al., Induction of NK activity in murine and human cells by CpG motifs in oligodeoxynucleotides and bacterial DNA. J Immunol. Sep. 1, 1996;157(5):1840-5.
Bates et al., Antiproliferative activity of G-rich oligonucleotides correlates with protein binding. J Biol Chem. Sep. 10, 1999;274(37):26369-77.
Bauer et al., DNA activates human immune cells through a CpG sequence-dependent manner. Immunology. Aug. 1999;97(4):699-705.
Boggs et al., Characterization and modulation of immune stimulation by modified oligonucleotides. Antisense Nucleic Acid Drug Dev. Oct. 1997;7(5):461-71.
Branda et al., Immune stimulation by an antisense oligomer complementary to the rev gene of HIV-1. Biochem Pharmacol. May 25, 1993;45(10):2037-43.

(56) References Cited

OTHER PUBLICATIONS

Branda et al., Amplification of antibody production by phosphorothioate oligodeoxynucleotides. J Lab Clin Med. Sep. 1996;128(3):329-38.
Broide et al., DNA-Based immunization for asthma. Int Arch Allergy Immunol. Feb.-Apr. 1999;118(2-4):453-6.
Burgess et al., The antiproliferative activity of c-myb and c-myc antisense oligonucleotides in smooth muscle cells is caused by a nonantisense mechanism. Proc Natl Acad Sci U S A. Apr. 25, 1995;92(9):4051-5.
Carpentier et al., Successful treatment of intracranial gliomas in rat by oligodeoxynucleotides containing CpG motifs. Clin Cancer Res. Jun. 2000;6(6):2469-73.
Chu et al., CpG oligodeoxynucleotides act as adjuvants that switch on T helper 1 (Th 1) immunity. J Exp Med. Nov. 17, 1997;186(10):1623-31.
Coley Pharmaceutical Group Press Release, Coley Pharmaceutical Group Updated Hepatitis C Drug Development Strategy. Jan. 22, 2007.
Coley Pharmaceutical Group Press Release, Coley Pharmaceutical Announces Pfizer's Discontinuation of Clinical Trials for PF-3512676 Combined with Cytotoxic Chemotherapy in Advanced Non Small Cell Lung Cancer, Jun. 20, 2007.
Cowsert et al., In vitro evaluation of phosphorothioate oligonucleotides targeted to the E2 mRNA of papillomavirus: potential treatment for genital warts. Antimicrob Agents Chemother. Feb. 1993;37(2):171-7.
Crooke et al., Phosphorothioate Oligonucleotides. Therapeut Apps. 1995;ch5:63-84.
Crooke et al., Progress in antisense oligonucleotide therapeutics. Annu Rev Pharmacol Toxicol. 1996;36:107-29.
Dapic et al., Proceedings of AACR, pp. 42 Mar. 2001:1122.
Davis, Use of CpG DNA for enhancing specific immune responses. Curr Top Microbiol Immunol. 2000;247:171-83.
Davis et al., CpG ODN is safe and highly effective in humans as adjuvant to HBV vaccine: Preliminary results of Phase I trial with CpG ODN 7909. Third Annual Conference on Vaccine Res. 2000. Abstract s25, No. 47.
Gallichan et al., Intranasal immunization with CpG oligodeoxynucleotides as an adjuvant dramatically increases IgA and protection against herpes simplex virus-2 in the genital tract. J Immunol. Mar. 1, 2001;166(5):3451-7.
Hafner et al., Antimetastatic effect of CpG DNA mediated by type I IFN. Cancer Res. Jul. 15, 2001;61(14):5523-8.
Hahm et al., Efficacy of polyadenylic.polyuridylic acid in the treatment of chronic active hepatitis B. Int J Immunopharmacol. Mar. 1994;16(3):217-25.
Harrington et al., Adjuvant effects of low doses of a nuclease-resistant derivative of polyinosinic acid . polycytidylic acid on antibody responses of monkeys to inactivated Venezuelan equine encephalomyelitis virus vaccine. Infect Immun. Apr. 1979;24(1):160-6.
Hartmann et al., CpG DNA and LPS induce distinct patterns of activation in human monocytes. Gene Ther. May 1999;6(5):893-903.
Hartmann et al., Mechanism and function of a newly identified CpG DNA motif in human primary B cells. J Immunol. Jan. 15, 2000;164(2):944-53.
Hartmann et al., Specific suppression of human tumor necrosis factor-alpha synthesis by antisense oligodeoxynucleotides. Antisense Nucleic Acid Drug Dev. 1996 Winter;6(4):291-9.
Hartmann et al., Delineation of a CpG phosphorothioate oligodeoxynucleotide for activating primate immune responses in vitro and in vivo. J Immunol. Feb. 1, 2000;164(3):1617-24.
Hartmann et al., CpG DNA: a potent signal for growth, activation, and maturation of human dendritic cells. Proc Natl Acad Sci U S A. Aug. 3, 1999;96(16):9305-10.
Heeg et al., CpG DNA as a Th 1 trigger. Int Arch Allergy Immunol. Feb. 2000;121(2):87-97.
Henry et al., Chemically modified oligonucleotides exhibit decreased immune stimulation in mice. J Pharmacol Exp Ther. Feb. 2000;292(2):468-79.
Hopkin et al., Curbing the CpGs of Bacterial and Viral DNA. BioMedNet. Jun. 25, 1999; Issue 57.
Hughes et al., Influence of base composition on membrane binding and cellular uptake of 10-mer phosphorothioate oligonucleotides in Chinese hamster ovary (CHRC5) cells. Antisense Res Dev. 1994 Fall;4(3):211-5.
Iho et al., Oligodeoxynucleotides containing palindrome sequences with internal 5'-CpG-3' act directly on human NK and activated T cells to induce IFN-gamma production in vitro. J Immunol. Oct. 1, 1999;163(7):3642-52.
Iversen et al., Pharmacokinetics of an antisense phosphorothioate oligodeoxynucleotide against rev from human immunodeficiency virus type 1 in the adult male rat following single injections and continuous infusion. Antisense Res Dev. 1994 Spring;4(1):43-52.
Kataoka et al., Antitumor activity of synthetic oligonucleotides with sequences from cDNA encoding proteins of *Mycobacterium bovis* BCG. Jpn J Cancer Res. Mar. 1992;83(3):244-7.
Kataoka et al., Immunotherapeutic potential in guinea-pig tumor model of deoxyribonucleic acid from *Mycobacterium bovis* BCG complexed with poly-L-lysine and carboxymethylcellulose. Jpn J Med Sci Biol. Oct. 1990;43(5):171-82.
Kern et al., Herpesvirus *hominis* infection in newborn mice: treatment with interferon inducer polyinosinic-polycytidylic acid. Antimicrob Agents Chemother. Jun. 1975;7(6):793-800.
Kimura et al., Binding of oligoguanylate to scavenger receptors is required for oligonucleotides to augment NK cell activity and induce IFN. J Biochem (Tokyo). Nov. 1994;116(5):991-4.
Klinman et al., Immunotherapeutic applications of CpG-containing oligodeoxynucleotides. Drug News Perspect. Jun. 2000;13(5):289-96.
Klinman et al., Immune recognition of foreign DNA: a cure for bioterrorism? Immunity. Aug. 1999;11(2):123-9.
Klinman et al., CpG motifs present in bacteria DNA rapidly induce lymphocytes to secrete interleukin 6, interleukin 12, and interferon gamma. Proc Natl Acad Sci U S A. Apr. 2, 1996;93(7):2879-83.
Kovarik et al., CpG oligodeoxynucleotides can circumvent the Th2 polarization of neonatal responses to vaccines but may fail to fully redirect Th2 responses established by neonatal priming. J Immunol. Feb. 1, 1999;162(3):1611-7.
Krieg et al., Immune effects and therapeutic applications of CpG motifs in bacterial DNA. Immunopharmacology. Jul. 25, 2000;48(3):303-5.
Krieg et al., Lymphocyte activation mediated by oligodeoxynucleotides or DNA containing novel un-methylated CpG motifs. American College of Rheumatology 58th National Scientific Meeting. Minneapolis, Minnesota, Oct. 22, 1994. Abstracts. Arthritis Rheum. Sep. 1994;37(9 Suppl).
Krieg et al., Oligodeoxynucleotide modifications determine the magnitude of B cell stimulation by CpG motifs. Antisense Nucleic Acid Drug Dev. 1996 Summer;6(2):133-9.
Krieg et al., Phosphorothioate oligodeoxynucleotides: antisense or anti-protein? Antisense Res Dev. 1995 Winter;5(4):241.
Krieg et al., Leukocyte stimulation by oligodeoxynucleotides. In: Applied Antisense Oligonucleotide Technology. 1998:431-48.
Krieg, CpG DNA: a pathogenic factor in systemic lupus erythematosus? J Clin Immunol. Nov. 1995;15(6):284-92.
Krieg et al., CpG motifs in bacterial DNA trigger direct B-cell activation. Nature. Apr. 6, 1995;374(6522):546-9.
Krieg et al., The role of CpG dinucleotides in DNA vaccines. Trends Microbiol. Jan. 1998;6(1):23-7.
Krieg, An innate immune defense mechanism based on the recognition of CpG motifs in microbial DNA. J Lab Clin Med. Aug. 1996;128(2):128-33.
Krieg et al., Applications of immune stimulatory CpG DNA for antigen-specific and antigen-nonspecific cancer immunotherapy. Eur J Canc. Oct. 1999; 35/Suppl4:S10. Abstract #14.
Krieg et al., Causing a commotion in the blood: immunotherapy progresses from bacteria to bacterial DNA. Immunol Today. Oct. 2000;21(10):521-6.

(56) References Cited

OTHER PUBLICATIONS

Krieg et al., Chapter 8: Immune Stimulation by Oligonucleotides. In: Antisense Research and Application. Crooke, Ed. 1998:243-62.
Krieg et al., Bacterial DNA or oligonucleotides containing CpG motifs protect mice from lethal *L. monocytogenes* challenge. 1996 Meeting on Molecular Approaches to the Control of Infectious Diseases. Cold Spring Harbor Laboratory, Sep. 9-13, 1996:116.
Krieg et al., Enhancing vaccines with immune stimulatory CpG DNA. Curr Opin Mol Ther. Feb. 2001;3(1):15-24.
Krieg, Chapter 7: CpG oligonucleotides as immune adjuvants. Ernst Schering Research Found Workshop 2001; 30:105-18.
Krieg, Immune effects and mechanisms of action of CpG motifs. Vaccine. Nov. 8, 2001;19(6):61822.
Krieg et al., Chapter 17:Immune stimulation by oligonucleotides. in Antisense Drug Tech. 2001;1394:471-515.
Krieg et al., Mechanisms and applications of immune stimulatory CpG oligodeoxynucleotides. Biochim Biophys Acta. Dec. 10, 1999;1489(1):107-16.
Krieg et al., The CpG motif: Implications for clinical immunology. BioDrugs. Nov. 1, 1998;10(5):341-6.
Krieg, The role of CpG motifs in innate immunity. Curr Opin Immunol. Feb. 2000;12(1):35-43.
Krieg et al., Mechanisms and therapeutic applications of immune stimulatory CpG DNA. Pharmacol Ther. Nov. 1999;84(2):113-20.
Krieg et al., Sequence motifs in adenoviral DNA block immune activation by stimulatory CpG motifs. Proc Natl Acad Sci U S A. Oct. 13, 1998;95(21):12631-6.
Krieg et al., CpG DNA induces sustained IL-12 expression in vivo and resistance to *Listeria monocytogenes* challenge. J Immunol. Sep. 1, 1998;161(5):2428-34.
Krieg et al., CpG DNA: a novel immunomodulator. Trends Microbiol. Feb. 1999;7(2):64-5.
Krieg, Signal transduction induced by immunostimulatory CpG DNA. Springer Semin Immunopathol. 2000;22(1-2):97-105.
Krieg et al., How to exclude immunostimulatory and other nonantisense effects of antisense oligonucleotides. Manual of Antisense. 1999:79-89.
Krieg et al., Infection. In: McGraw Hill Book. 1996:242-3.
Krieg et al., Lymphocyte activation by CpG dinucleotide motifs in prokaryotic DNA. Trends Microbiol. Feb. 1996;4(2):73-6.
Krieg et al., Mechanism of action of CpG DNA. Curr Top Microbiol Immunol. 2000;247:1-21.
Kuramoto et al., Induction of T-cell-mediated immunity against MethA fibrosarcoma by intratumoral injections of a bacillus Calmette-Guerin nucleic acid fraction. Cancer Immunol Immunother. 1992;34(5):283-8.
Kuramoto et al., Changes of host cell infiltration into Meth A fibrosarcoma tumor during the course of regression induced by injections of a BCG nucleic acid fraction. Int J Immunopharmacol. Jul. 1992;14(5):773-82.
Kuramoto et al., Oligonucleotide sequences required for natural killer cell activation. Jpn J Cancer Res. Nov. 1992;83(11):1128-31.
Kuramoto et al., In situ infiltration of natural killer-like cells induced by intradermal injection of the nucleic acid fraction from BCG. Microbiol Immunol. 1989;33(11):929-40.
Lederman et al., Polydeoxyguanine motifs in a 12-mer phosphorothioate oligodeoxynucleotide augment binding to the v3 loop of HIV-1 gp120 and potency of HIV-1 inhibition independency of G-tetrad formation. Antisense Nucleic Acid Drug Dev. 1996 Winter;6(4):281-9.
Lee et al., An oligonucleotide blocks interferon-gamma signal transduction. Transplantation. Nov. 15, 1996;62(9):1297-301.
Leonard et al., Conformation of guanine-8-oxoadenine base pairs in the crystal structure of d(CGCGAATT(O8A)GCG). Biochemistry. Sep. 15, 1992;31(36):8415-20.
Levine et al., Phase I-II trials of poly IC stabilized with poly-L-lysine. Cancer Treat Rep. Nov. 1978;62(11):1907-12.
Levy et al., Prophylactic control of simian hemorrhagic fever in monkeys by an interferon inducer, polyriboinosinic-polyribocytidylic acid-poly-L-lysine. J Infect Dis. Jun. 1976;133 Suppl:A256-9.
Lipford et al., CpG-containing synthetic oligonucleotides promote B and cytotoxic T cell responses to protein antigen: a new class of vaccine adjuvants. Eur J Immunol. Sep. 1997;27(9):2340-4.
Lipford et al., Immunostimulatory DNA: sequence-dependent production of potentially harmful or useful cytokines. Eur J Immunol. Dec. 1997;27(12):3420-6.
Lipford et al., Bacterial DNA as immune cell activator. Trends Microbiol. Dec. 1998;6(12):496-500.
Lipford et al., Poly-guanosine motifs costimulate antigen-reactive CD8 T cells while bacterial CpG-DNA affect T-cell activation via antigen-presenting cell-derived cytokines. Immunology. Sep. 2000;101(1):46-52.
Liu et al., CpG ODN is an effective adjuvant in immunization with tumor antigen. J Invest Med. Sep. 7, 1997;45(7):333A.
Loke et al., Delivery of c-myc antisense phosphorothioate oligodeoxynucleotides to hematopoietic cells in culture by liposome fusion: specific reduction in c-myc protein expression correlates with inhibition of cell growth and DNA synthesis. Curr Top Microbiol Immunol. 1988;141:282-9.
Macaya et al., Thrombin-binding DNA aptamer forms a unimolecular quadruplex structure in solution. Proc Natl Acad Sci U S A. Apr. 15, 1993;90(8):3745-9.
Maltese et al., Sequence context of antisense RelA/NF-kappa B phosphorothioates determines specificity. Nucleic Acids Res. Apr. 11, 1995;23(7):1146-51.
Martin-Orozco et al., Enhancement of antigen-presenting cell surface molecules involved in cognate interactions by immunostimulatory DNA sequences. Int Immunol. Jul. 1999;11(7):1111-8.
Matson et al., Nonspecific suppression of [3H]thymidine incorporation by "control" oligonucleotides. Antisense Res Dev. 1992 Winter;2(4):325-30.
Matsukura et al., Regulation of viral expression of human immunodeficiency virus in vitro by an antisense phosphorothioate oligodeoxynucleotide against rev (art/trs) in chronically infected cells. Proc Natl Acad Sci U S A. Jun. 1989;86(11):4244-8.
McCluskie et al., CpG DNA is a potent enhancer of systemic and mucosal immune responses against hepatitis B surface antigen with intranasal administration to mice. J Immunol. Nov. 1, 1998;161(9):4463-6.
McCluskie et al., CpG DNA as mucosal adjuvant. Vaccine. 2000;18: 231-7.
McIntyre et al., A sense phosphorothioate oligonucleotide directed to the initiation codon of transcription factor NF-kappa B p65 causes sequence-specific immune stimulation. Antisense Res Dev. 1993 Winter;3(4):309-22.
Messina et al., The influence of DNA structure on the in vitro stimulation of murine lymphocytes by natural and synthetic polynucleotide antigens. Cell Immunol. Mar. 1993;147(1):148-57.
Michelson et al. Poly(A).poly(U) as adjuvant in cancer treatment distribution and pharmacokinetics in rabbits. Proc Soc Exp Biol Med. Jun. 1985;179(2):180-6.
Monteith et al., Immune stimulation—a class effect of phosphorothioate oligodeoxynucleotides in rodents. Anticancer Drug Des. Jul. 1997;12(5):421-32.
Nyce et al., DNA antisense therapy for asthma in an animal model. Nature. Feb. 20, 1997;385(6618):721-5.
Park et al., The enhanced effect of a hexameric deoxyriboguanosine run conjugation to CpG oligodeoxynucleotides on protection against allergic asthma. J Allergy Clin Immunol. Oct. 2001;108(4):570-6.
Perlaky et al., Growth inhibition of human tumor cell lines by antisense oligonucleotides designed to inhibit p120 expression. Anticancer Drug Des. Feb. 1993;8(1):3-14.
Pisetsky et al., The immunologic properties of DNA. J Immunol. Jan. 15, 1996;156(2):421-3.
Pisetsky et al., Influence of backbone chemistry on immune activation by synthetic oligonucleotides. Biochem Pharmacol. Dec. 15, 1999;58(12):1981-8.

(56) References Cited

OTHER PUBLICATIONS

Pisetsky et al., Stimulation of murine lymphocyte proliferation by a phosphorothioate oligonucleotide with antisense activity for herpes simplex virus. Life Sci. 1994;54(2):101-7.
Pisetsky, Immunologic consequences of nucleic acid therapy. Antisense Res Dev. 1995 Fall;5(3):219-25.
Pisetsky et al., Stimulation of in vitro proliferation of murine lymphocytes by synthetic oligodeoxynucleotides. Mol Biol Rep. Oct. 1993;18(3):217-21.
Pisetsky, The influence of base sequence on the immunostimulatory properties of DNA. Immunol Res. 1999;19(1):35-46.
Pisetsky et al., The influence of base sequence on the immunological properties of defined oligonucleotides. Immunopharmacology. Nov. 1998;40(3):199-208.
Polanczyk et al., Immunostimulatory effects of DNA and CpG motifs. Cent Eur J of Immunol. 2000;25(3): 160-6.
Rankin et al., CpG motif identification for veterinary and laboratory species demonstrates that sequence recognition is highly conserved. Antisense Nucleic Acid Drug Dev. Oct. 2001;11(5):333-40.
Roman et al., Immunostimulatory DNA sequences function as T helper-1-promoting adjuvants. Nat Med. Aug. 1997;3(8):849-54.
Sarmiento et al., In vivo toxicological effects of rel A antisense phosphorothioates in CD-1 mice. Antisense Res Dev. 1994 Summer;4(2):99-107.
Sato et al., Immunostimulatory DNA sequences necessary for effective intradermal gene immunization. Science. Jul. 19, 1996;273(5273):352-4.
Sester et al., Phosphorothioate backbone modification modulates macrophage activation by CpG DNA. J Immunol. Oct. 15, 2000;165(8):4165-73.
Sonehara et al., Hexamer palindromic oligonucleotides with 5'-CG-3' motif(s) induce production of interferon. J Interferon Cytokine Res. Oct. 1996;16(10):799-803.
Sparwasser et al., Bacterial DNA causes septic shock. Nature. Mar. 27, 1997;386(6623):336-7.
Stein et al., Problems in interpretation of data derived from in vitro and in vivo use of antisense oligonucleotides. Antisense Res Dev. 1994 Summer;4(2):67-9.
Stein et al., Non-antisense effects of oligodeoxynucleotides. Antisense Technology. 1997; ch11: 241-64.
Sun et al. Type I interferon-mediated stimulation of T cells by CpG DNA. J Exp Med. Dec. 21, 1998;188(12):2335-42.
Sun et al. Multiple effects of immunostimulatory DNA on T cells and the role of type I interferons. Springer Semin Immunopathol. 2000;22(1-2):77-84.
Talmadge et al., Immunomodulatory effects in mice of polyinosinic-polycytidylic acid complexed with poly-L-lysine and carboxymethylcellulose. Cancer Res. Mar. 1985;45(3):1058-65.
Threadgill et al., Mitogenic synthetic polynucleotides suppress the antibody response to a bacterial polysaccharide. Vaccine. Jan. 1998;16(1):76-82.
Tokunaga et al., A synthetic single-stranded DNA, poly(dG,dC), induces interferon-alpha/beta and -gamma, augments natural killer activity, and suppresses tumor growth. Jpn J Cancer Res. Jun. 1988;79(6):682-6.
Tortora et al., Oral antisense that targets protein kinase A cooperates with taxol and inhibits tumor growth, angiogenesis, and growth factor production. Clin Cancer Res. Jun. 2000;6(6):2506-12.
Valentine et al., Kinetics of formation of hypoxanthine containing base pairs by HIV-RT: RNA template effects on the base substitution frequencies. Nucleic Acids Res. 2001, 29(5): 1191-1199.
Verthelyi et al., Human peripheral blood cells differentially recognize and respond to two distinct CPG motifs. J Immunol. Feb. 15, 2001;166(4):2372-7.
Wagner et al., CpG motifs are efficient adjuvants for genetic vaccines to induce antigen-specific protective anti-tumor T cell responses. Immunobiology. 2000;203:429. Abstract R46.
Weeratna et al., CpG ODN can re-direct the Th bias of established Th2 immune responses in adult and young mice. FEMS Immunol Med Microbiol. Dec. 2001;32(1):65-71.
Weiner et al., The immunobiology and clinical potential of immunostimulatory CpG oligodeoxynucleotides. J Leukoc Biol. Oct. 2000;68(4):455-63.
Yamamoto et al., Lipofection of synthetic oligodeoxyribonucleotide having a palindromic sequence of AACGTT to murine splenocytes enhances interferon production and natural killer activity. Microbiol Immunol. 1994;38(10):831-6.
Yamamoto et al., Unique palindromic sequences in synthetic-oligonucleotides are required to induce IFN [correction of INF] and augment IFN-mediated [correction of INF] natural killer activity. J Immunol. Jun. 15, 1992;148(12):4072-6.
Yamamoto et al., Ability of oligonucleotides with certain palindromes to induce interferon production and augment natural killer cell activity is associated with their base length. Antisense Res Dev. 1994 Summer;4(2):119-22.
Yamamoto et al., Synthetic oligonucleotides with certain palindromes stimulate interferon production of human peripheral blood lymphocytes in vitro. Jpn J Cancer Res. Aug. 1994;85(8):775-9.
Yi et al. Rapid induction of mitogen-activated protein kinases by immune stimulatory CpG DNA. J Immunol. Nov. 1, 1998;161(9):4493-7.
Yi et al. CpG oligodeoxyribonucleotides rescue mature spleen B cells from spontaneous apoptosis and promote cell cycle entry. J Immunol. Jun. 15, 1998;160(12):5898-906.
Zhao et al., Pattern and kinetics of cytokine production following administration of phosphorothioate oligonucleotides in mice. Antisense Nucleic Acid Drug Dev. Oct. 1997;7(5):495-502.
Goldberg et al., Beyond danger: unmethylated CpG dinucleotides and the immunopathogenesis of disease. Immunol Lett. Jul. 3, 2000;73(1):13-8.
Hartmann et al., Rational design of new CpG oligonucleotides that combine B cell activation with high IFN-alpha induction in plasmacytoid dendritic cells. Eur J Immunol. Jun. 2003;33(6):1633-41.
Krieg, Now I know my CpGs.Trends Microbiol. Jun. 2001;9(6):249-52.
Lee et al., Effects of a hexameric deoxyriboguanosine run conjugation into CpG oligodeoxynucleotides on their immunostimulatory potentials. J Immunol. Oct. 1, 2000;165(7):3631-9.
Marshall et al., Identification of a novel CpG DNA class and motif that optimally stimulate B cell and plasmacytoid dendritic cell functions.J Leukoc Biol. Jun. 2003;73(6):781-92.
Mutwiri et al., Biological activity of immunostimulatory CpG DNA motifs in domestic animals. Vet Immunol Immunopathol. Jan. 30, 2003;91(2):89-103.
Scheule, The role of CpG motifs in immunostimulation and gene therapy. Adv Drug Deliv Rev. Nov. 15, 2000;44(2-3):119-34.
Storey et al., Anti-sense phosphorothioate oligonucleotides have both specific and non-specific effects on cells containing human papillomavirus type 16. Nucleic Acids Res. Aug. 11, 1991;19(15):4109-14.
Yamada et al., Effect of suppressive DNA on CpG-induced immune activation. J Immunol. Nov. 15, 2002;169(10):5590-4.
Zhang et al., Antisense oligonucleotide inhibition of hepatitis C virus (HCV) gene expression in livers of mice infected with an HCV-vaccinia virus recombinant. Antimicrob Agents Chemother. Feb. 1999;43(2):347-53.
Hanecak et al., Antisense oligonucleotide inhibition of hepatitis C virus gene expression in transformed hepatocytes. J Virol. Aug. 1996;70(8):5203-12.
Vollmer, TLR9 in health and disease. Int Rev Immunol. May-Aug. 2006;25(3-4):155-81.
Vollmer et al., Identification of a new class of CpG oligonucleotides capapble of inducing both B cell proliferation and hihg IFN-alpha secretion from PBMC of HCV chronic carriers. Antiv Ther. 2002;7:L115.

\* cited by examiner

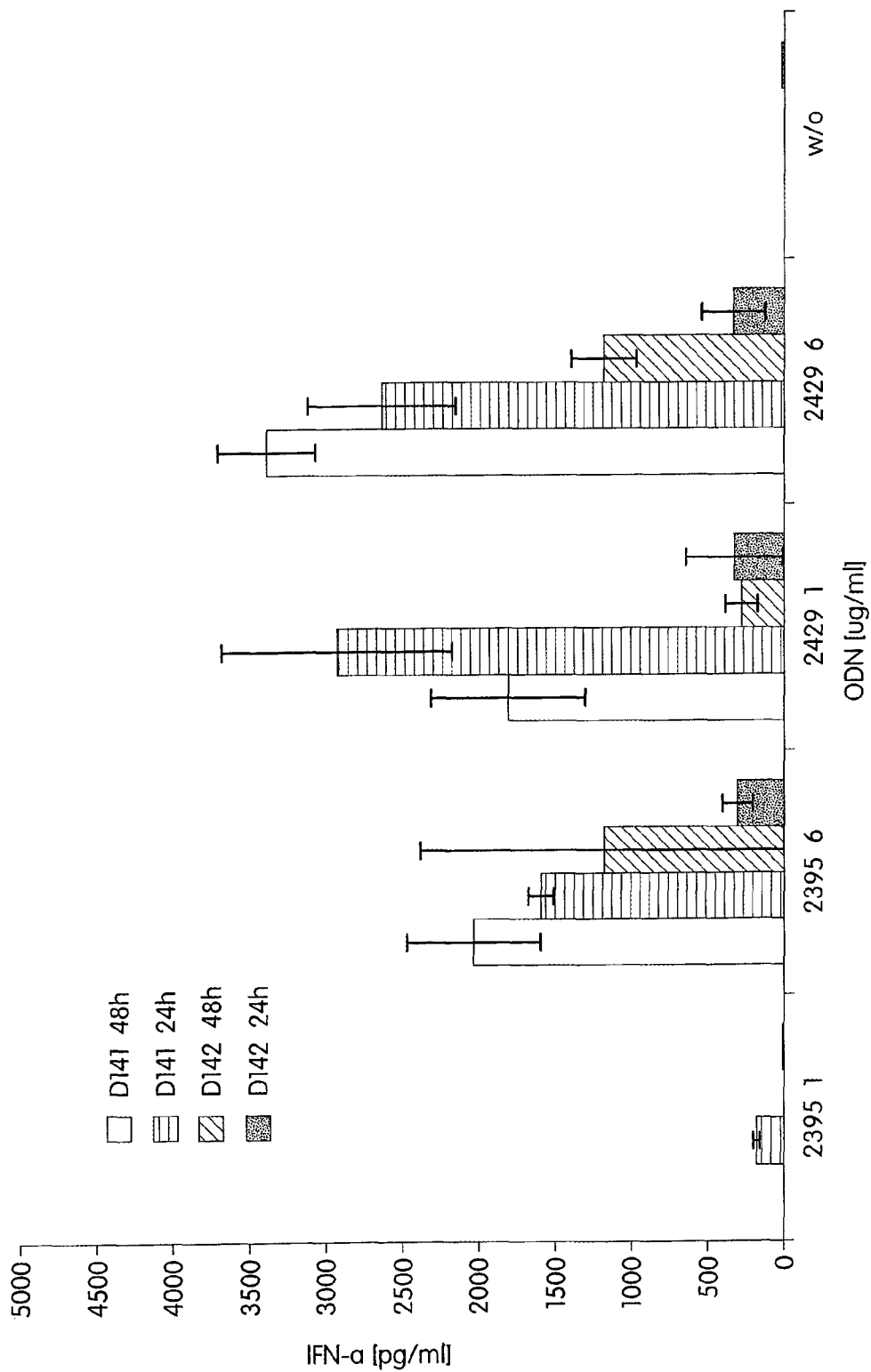

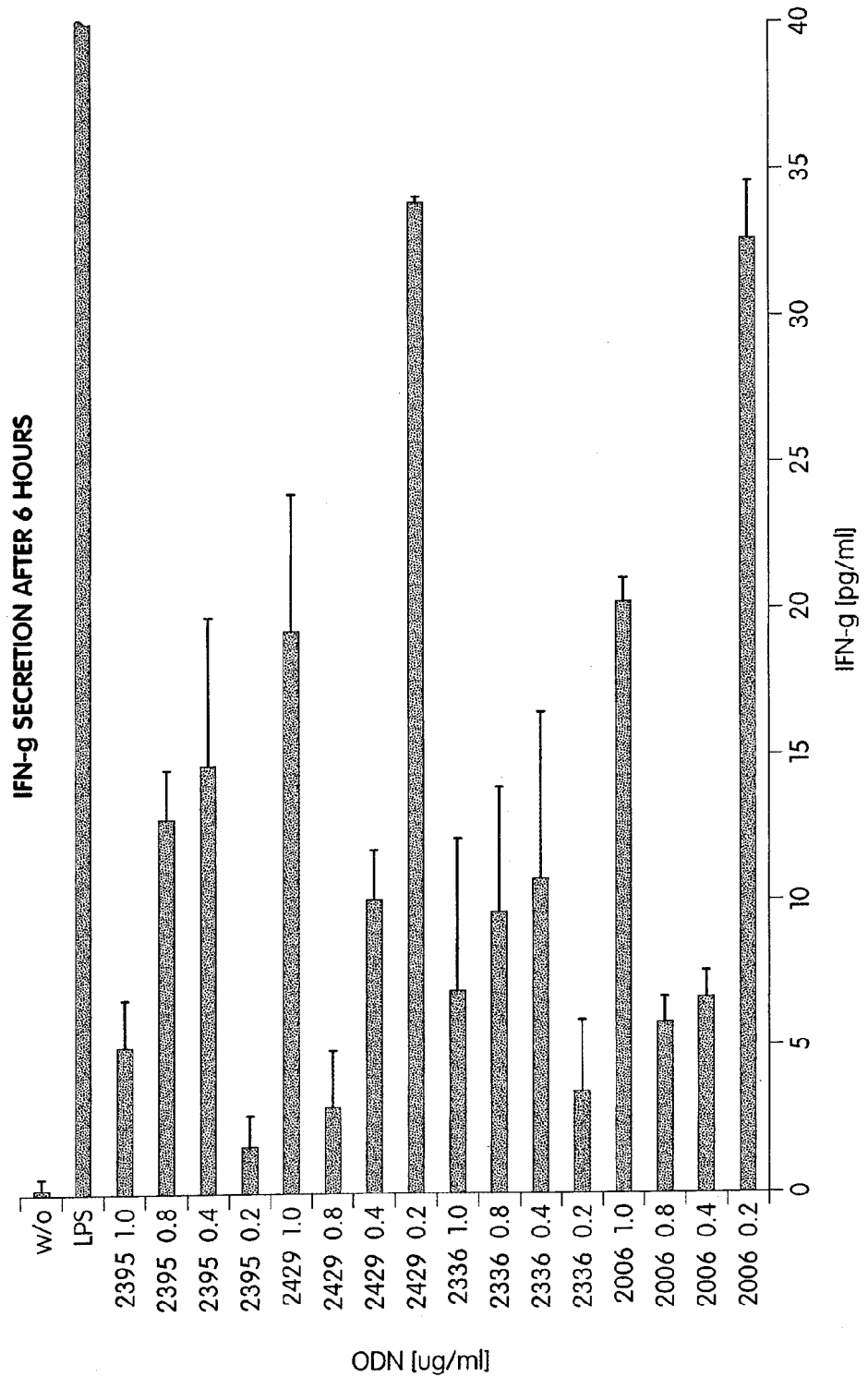

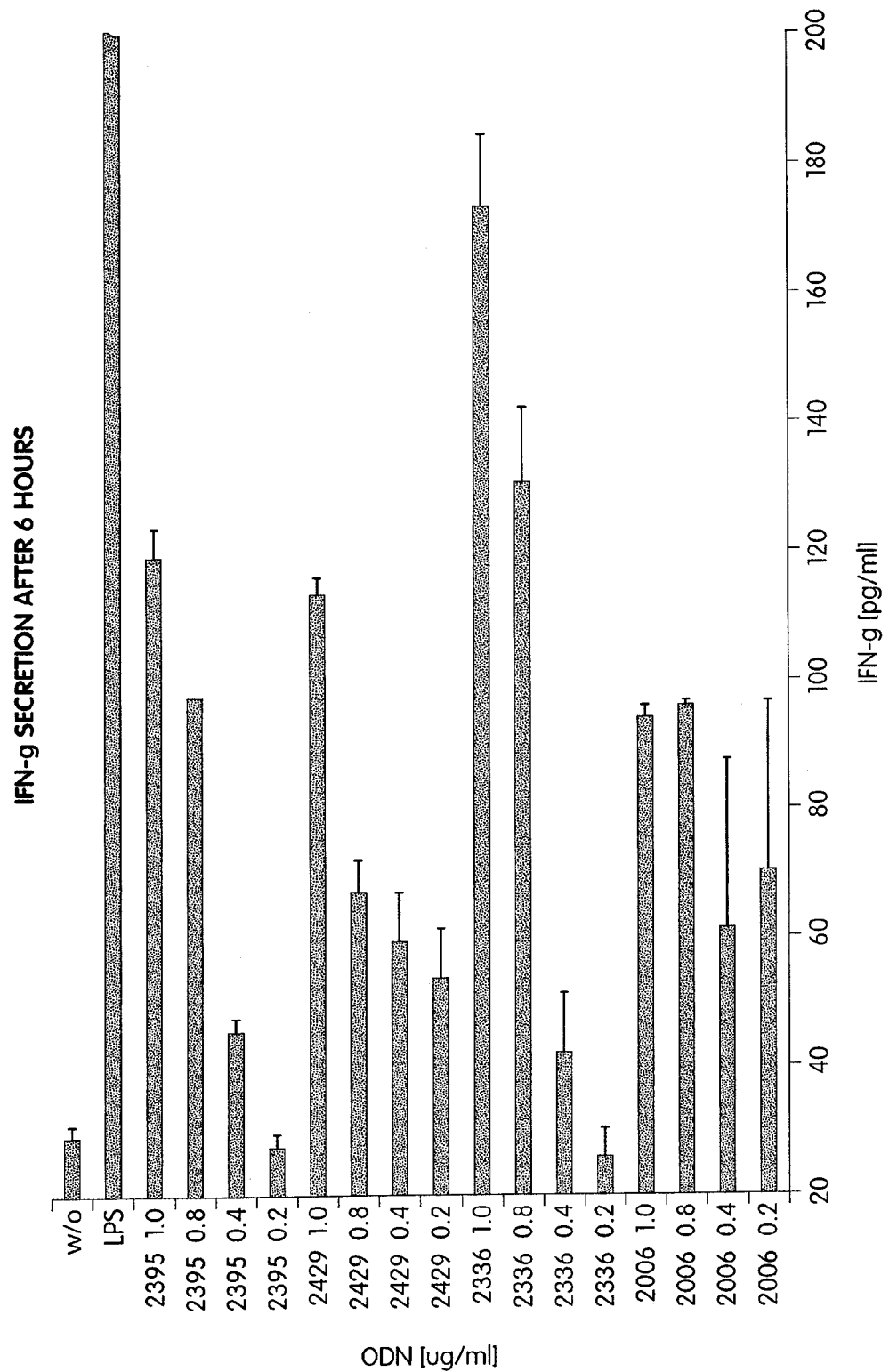

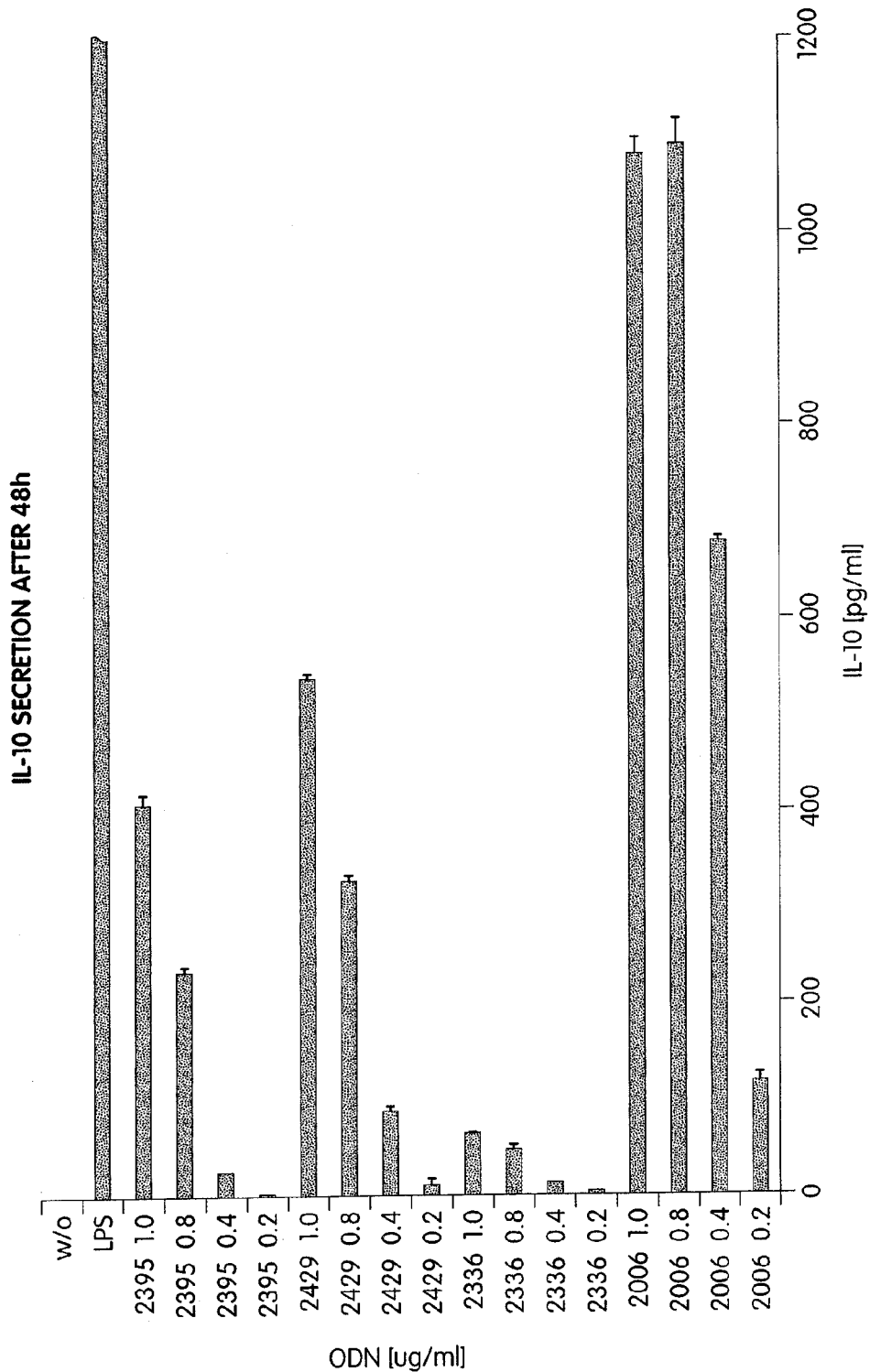

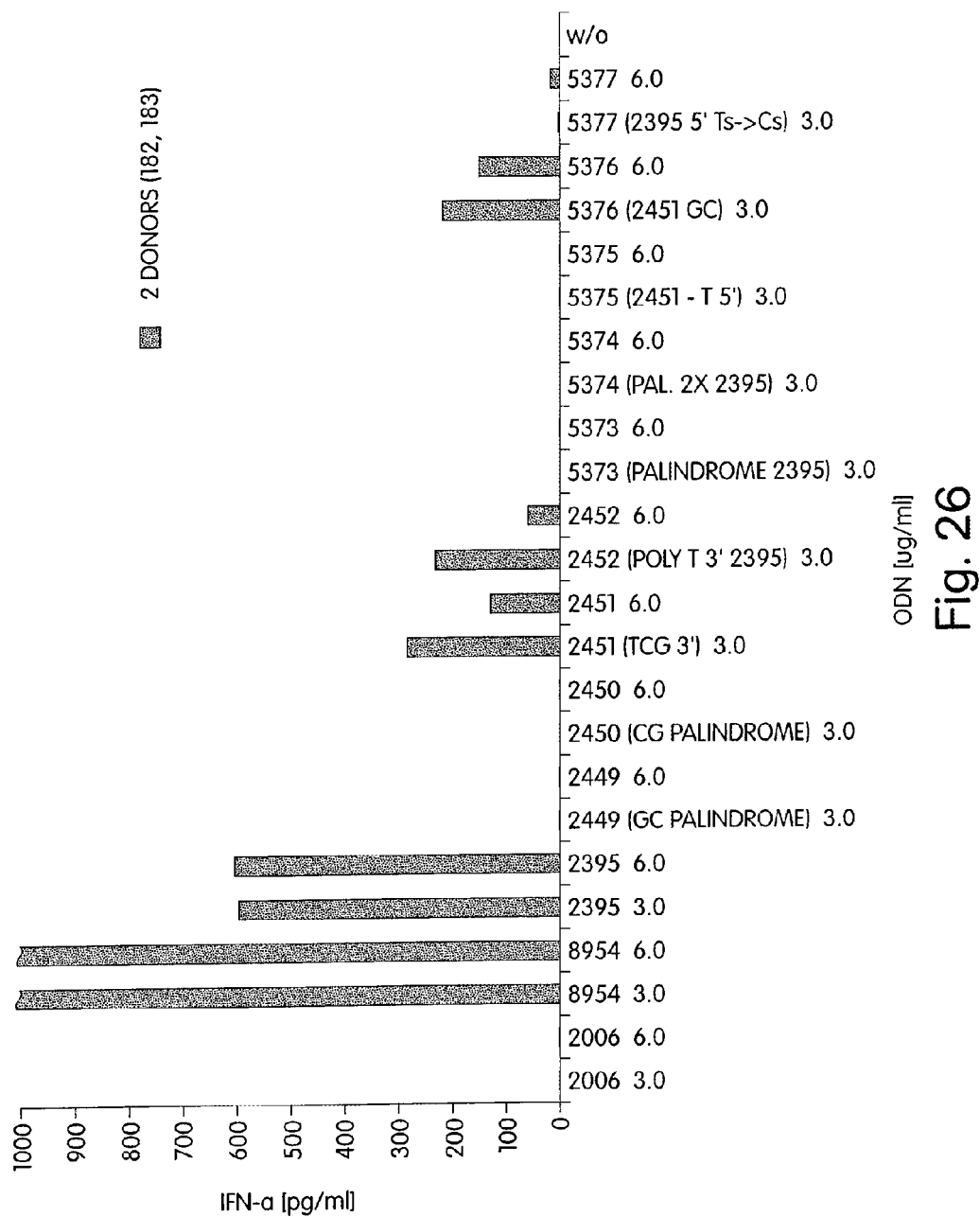

COMBINATION MOTIF IMMUNE STIMULATORY OLIGONUCLEOTIDES WITH IMPROVED ACTIVITY

RELATED APPLICATIONS

This application claims the benefit of priority of U.S. Provisional Application Ser. Nos. 60/313,273, filed Aug. 17, 2001 and 60/393,952, filed Jul. 3, 2002, each of which is incorporated by reference in its entirety.

FIELD OF THE INVENTION

The present invention relates generally to immunostimulatory nucleic acids, compositions thereof, and methods of using the immunostimulatory nucleic acids.

BACKGROUND

Two main classes of immune stimulatory sequences are known in the art which have differing profiles of immune stimulatory activity. Krieg A M (2001) *Trends Microbiol* 9:249-52. These are so-called class B CpG oligodeoxynucleotides (ODN), which are strong activators of B cells, and class A CpG ODN, which are strong activators of natural killer (NK) cells. In addition to these immune stimulatory sequences, at least two classes of neutralizing sequences are known, including CpG sequences in which the CG is preceded by aC or followed by a G (Krieg A M et al. (1998) *Proc Natl Acad Sci USA* 95:12631-12636), and DNA sequences in which the CG is methylated. A neutralizing motif is a motif which has some degree of immunostimulatory capability when present in an otherwise non-stimulatory motif, but, which when present in the context of other immunostimulatory motifs serves to reduce the immunostimulatory potential of the other motifs.

SUMMARY OF THE INVENTION

A new class of immune stimulatory nucleic acids is provided herein. In some instances these nucleic acids have a CG-rich palindrome or CG-rich neutralizing motif. Applicants previously recognized and described oligodeoxynucleotides (ODN) containing neutralizing motifs consisting of repeats of the sequence CG such as CGCGCG or a CG dinucleotide preceded by a C (i.e., CCG) and/or followed by a G (i.e., CGG, CCGG). These neutralizing motifs were believed cause some reduction in stimulatory effects of CpG containing ODN on multiple readouts, such as secretion of IL-6, IL-12, IFN-γ, TNF-α, and induction of an antigen-specific immune response. Krieg A M et al. (1998) *Proc Natl Acad Sci USA* 95:12631-6.

The present invention is based in part on the surprising discovery by the Applicants that certain ODN containing a combination of a stimulating motif and a neutralizing motif are highly immunostimulatory. The present invention is also based in part on the surprising discovery by the Applicants that ODN having certain CG-rich palindromic sequences, including palindromic sequences containing neutralizing motifs, are highly immunostimulatory. The neutralizing motif thus, may, but need not occur within the context of a palindromic sequence to be highly immunostimulatory.

Furthermore, the immunostimulatory ODN of the instant invention have immunostimulatory effects previously associated with both of two distinct classes of CpG ODN, those that characteristically activate B cells (class B CpG ODN) and those that characteristically activate NK cells and induce production of interferon (IFN)-α (class A CpG ODN). The novel immunostimulatory ODN of the instant invention thus have a spectrum of immunostimulatory effects distinct from either class A CpG ODN or class B CpG ODN. The new class of immunostimulatory ODN of the instant invention is referred to as type C CpG ODN. As described in greater detail below, in certain embodiments the ODN of the present invention involve a combination of motifs wherein one motif is a CG-rich palindrome or a neutralizing motif, and another motif is a stimulatory motif, e.g., a CpG motif or the sequence TCGTCG.

In some aspects an immunostimulatory nucleic acid of 14-100 nucleotides in length is provided. The nucleic acid has the formula: 5' $X_1DCGHX_2$ 3'. $X_1$ and $X_2$ are independently any sequence 0 to 10 nucleotides long. D is a nucleotide other than C. C is cytosine. G is guanine. H is a nucleotide other than G. The nucleic acid sequence also includes a nucleic acid sequence selected from the group consisting of P and N positioned immediately 5' to $X_1$ or immediately 3' to $X_2$. N is a B-cell neutralizing sequence which begins with a CGG trinucleotide and is at least 10 nucleotides long. P is a GC-rich palindrome containing sequence at least 10 nucleotides long.

In some embodiments the immunostimulatory nucleic acid is 5' $NX_1DCGHX_2$ 3', 5' $X_1DCGHX_2N$ 3', 5' $PX_1DCGHX_2$ 3', 5' $X_1DCGHX_2P$ 3', 5' $X_1DCGHX_2PX_3$ 3', 5' $X_1DCGHPX_3$ 3', 5' $DCGHX_2PX_3$ 3', 5' $TCGHX_2PX_3$ 3', or 5' $DCGHPX_3$ 3'. $X_3$ is any sequence 0 to 10 nucleotides long. In other embodiments the immunostimulatory nucleic acid is 5" DCGHP 3'.

Optionally D and/or H are thymine (T).

In other embodiments H is T and $X_2$ is CG, CGT, CGTT, CGTTT, or CGTTTT.

H is T and $X_2$ is CG or CGTTTT according to other embodiments.

According to other embodiments C is unmethylated.

N includes at least four CG dinucleotides and no more than two CCG trinucleotides in some embodiments.

Optionally P includes at least one Inosine.

The nucleic acid may also include a poly-T sequence at the 5' end or the 3' end.

An immunostimulatory nucleic acid of 13-100 nucleotides in length is provided according to other aspects of the invention. The nucleic acid has the formula: 5' $N_1PyGN_2P$ 3'. G is guanine.

$N_1$ is any sequence 1 to 6 nucleotides long. In some embodiments $N_1$ is at least 50% pyrimidines and preferably at least 50% T. In other embodiments $N_1$ includes at least one CG motif, at least one TCG motif, at least one CT motif, at least one TCI motif, at least one IG motif, or at least one TIG motif. $N_1$ is TCGG or TCGH in other embodiments. H is a nucleotide other than G.

Py is a pyrimidine. In some embodiments Py is an unmethylated C.

$N_2$ is any sequence 0 to 30 nucleotides long. In some embodiments $N_2$ is at least 50% pyrimidines or is at least 50% T. In other embodiments $N_2$ does not includes any poly G or poly A motifs.

P is a GC-rich palindrome containing sequence at least 10 nucleotides long. In some embodiments P is completely palindromic. In other embodiments P is a palindrome having between 1 and 3 consecutive intervening nucleotides. Optionally the intervening nucleotides may be TG. In other embodiments P includes at least 3, 4, or 5 C and at least 3, 4, or 5 G nucleotides. According to other embodiments P includes at least one Inosine.

In one embodiment the GC-rich palindrome has a base content of at least two-thirds G and C. In another embodiment the GC-rich palindrome has a base content of at least 81 percent G and C. In some embodiments the GC-rich palindrome is at least 12 nucleotides long. The GC-rich palindrome may be made up exclusively of C and G. In some embodiments the GC-rich palindrome can include at least one nucleotide that is neither C nor G.

In some embodiments the GC-rich palindrome includes at least one CGG trimer, at least one CCG trimer, or at least one CGCG tetramer. In some embodiments the GC-rich palindrome includes at least four CG dinucleotides. In certain preferred embodiments the GC-rich palindrome has a central CG dinucleotide.

In certain embodiments the GC-rich palindrome is CGGCGCGCGCCG (SEQ ID NO: 23), CGGCGGCCGCCG (SEQ ID NO: 28), CGACGATCGTCG (SEQ ID NO: 68) or CGACGTACGTCG (SEQ ID NO: 69).

In certain embodiments the GC-rich palindrome is not CGCGCGCGCGCG (SEQ ID NO: 29), GCGCGCGCGCGC (SEQ ID NO: 30), CCCCCCGGGGGG (SEQ ID NO: 31), GGGGGGCCCCCC (SEQ ID NO: 32), CCCCCGGGGG (SEQ ID NO: 33) or GGGGGCCCCC (SEQ ID NO: 34).

In some embodiments $N_1PyGN_2$ is a sequence selected from the group consisting of TTTTTCG, TCG, TTCG, TTTCG, TTTTCG, TCGT, TTCGT, TTTCGT, and TCGTCGT.

An immunostimulatory nucleic acid of 13-100 nucleotides in length is provided according to other aspects of the invention. The nucleic acid has the formula: 5' $N_1PyG/IN_2P$ 3'. G/I refers to single nucleotide which is either a G or an I. G is guanine and I is Inosine.

$N_1$ is any sequence 1 to 6 nucleotides long. Py is a pyrimidine. $N_2$ is any sequence 0 to 30 nucleotides long.

P is a palindrome containing sequence at least 10 nucleotides long. In some embodiments P is a GC-rich palindrome. In other embodiments P is an IC-rich palindrome.

$N_1PyIN_2$ in some embodiments is TCITCITTTT (SEQ ID NO: 47).

The nucleic acid molecules described herein may have any type of backbone composition. In some embodiments the immunostimulatory nucleic acid has a completely nuclease-resistant backbone. The nuclease-resistant backbone may be composed of phosphorothioate linkages. In other embodiments the immunostimulatory nucleic acid has a completely phosphodiester backbone. In yet other embodiments the immunostimulatory nucleic acid has a chimeric backbone. In one embodiment the immunostimulatory nucleic acid has at least one phosphodiester linkage between a CG, CI or a IG motif. Alternatively, the ODN of the instant invention are formulated with microparticles, emulsions, or other means to avoid rapid digestion in vivo.

The immunostimulatory nucleic acid molecules described herein have a variety of lengths. In some embodiments the immunostimulatory nucleic acid is 13-100, 13-40, 13-30, 14-100, 14-40, or 14-30 nucleotides in length or any integer therebetween.

An immunostimulatory nucleic acid having one of the following sequences is also provided: TCGTCGTTTTCGGCGCGCGCCG (SEQ ID NO: 1), TCGTCGTTTTCGGCGGCCGCCG (SEQ ID NO: 4), TCGTCGTTTTCGGCGCGCCGCG (SEQ ID NO: 5), TCGTCGTTTTCGGCGCCGGCCG (SEQ ID NO: 6), TCGTCGTTTTCGGCCCGCGCGG (SEQ ID NO: 7), TCGTCGTTTTCGGCGCGCGCCGTTTTT (SEQ ID NO: 12), TCCTGACGTTCGGCGCGCGCCG (SEQ ID NO: 13), TZGTZGTTTTZGGZGZGZGZZG (SEQ ID NO: 14), wherein Z is 5-methylcytosine, TCCTGACGTTCGGCGCGCGCCC (SEQ ID NO: 19), TCGGCGCGCGCCGTCGTCGTTT (SEQ ID NO: 11), TCCTGACGTTCGGCGCGCGCCC (ODN 2136, SEQ ID NO: 19), TCGTCGTTTTCGGCGGCCGACG (ODN 5513, SEQ ID NO: 64), TCGTCGTTTTCGTCGGCCGCCG (ODN 5514, SEQ ID NO: 65), TCGTCGTTTTCGACGGCCGCCG (ODN 5515, SEQ ID NO: 66), and TCGTCGTTTTCGGCGGCCGTCG (ODN 5516, SEQ ID NO: 67).

Further according to other embodiments of the invention the immunostimulatory nucleic acid is one of the following sequences: TCGTCGTTTTCGGCGCGCGCCG (ODN 2395), TCGTCGTTTTCGGCGGCCGCCG (ODN 2429), TCGTCGTTTTCGGCGCGCCGCG (ODN 2430), TCGTCGTTTTCGGCGCCGGCCG (ODN 2431), TCGTCGTTTTCGGCCCGCGCGG (ODN 2432), TCGTCGTTTTCGGCGCGCGCCGTTTTT (ODN 2452), TCCTGACGTTCGGCGCGCGCCG (ODN 5315), TZGTZGTTTTZGGZGZGZGZZG (ODN 5327, wherein Z is 5-methylcytosine), TCCTGACGTTCGGCGCGCGCCC (ODN 2136), TCGTCGTTTTCGGCGGCCGACG (ODN 5513), TCGTCGTTTTCGTCGGCCGCCG (ODN 5514), TCGTCGTTTTCGACGGCCGCCG (ODN 5515), TCGTCGTTTTCGGCGGCCGTCG (ODN 5516), TCGTCGTTTTCGGCGCGCGCCG (ODN 2395), TCGTCGTTTTCGGCGGCCGCCG (ODN 2429), TCGTCGTTTTCGGCGCGCCGCG (ODN 2430), TCGTCGTTTTCGGCGCCGGCCG (ODN 2431), TCGTCGTTTTCGGCCCGCGCGG (ODN 2432), TCGTCGTTTTCGGCGCGCGCCGTTTTT (ODN 2452), TCCTGACGTTCGGCGCGCGCCG (ODN 5315), TZGTZGTTTTZGGZGZGZGZZG (ODN 5327, wherein Z is 5-methylcytosine), TCCTGACGTTCGGCGCGCGCCC (ODN 2136), TCGTCGTTTTCGGCGGCCGACG (ODN 5513), TCGTCGTTTTCGTCGGCCGCCG (ODN 5514), TCGTCGTTTTCGACGGCCGCCG (ODN 5515), TCGTCGTTTTCGGCGGCCGTCG (ODN 5516), TCGGCGCGCCGTCGTCGTTT (ODN 2451), TCGTCGTTTCGACGGCCGTCG (ODN 20173, SEQ ID NO: 71), TCGTCGTTTCGACGATCGTCG (ODN 20176, SEQ ID NO: 72), TCGTCGTTTCGACGTACGTCG (ODN 20177, SEQ ID NO: 73), TCGTCGCGACGGCCGTCG (ODN 20178, SEQ ID NO: 74), TCGTCGCGACGATCGTCG (ODN 20179, SEQ ID NO: 75), TCGTCGCGACGTACGTCG (ODN 20180, SEQ ID NO: 76), TCGTTTTTTTCGACGGCCGTCG (ODN 20184, SEQ ID NO: 77), TCGTTTTTTTCGACGATCGTCG (ODN 20185, SEQ ID NO: 78), and TCGTTTTTTTCGACGTACGTCG (ODN 20186, SEQ ID NO: 79).

According to certain embodiments the immunostimulatory nucleic acid includes the sequence TCGGCGCGCGCCGTCGTCGTTT (ODN 2451, SEQ ID NO: 11). In certain embodiments the immunostimulatory nucleic acid is the sequence TCGGCGCGCGCCGTCGTCGTTT (ODN 2451).

A pharmaceutical composition, comprising the immunostimulatory nucleic acids described herein and a pharmaceutically acceptable carrier is provided according to other aspects of the invention.

In other aspects of the invention a method for inducing type 1 interferon (IFN) expression is provided. The method involves contacting a cell capable of expressing type 1 IFN with an effective amount of an immunostimulatory nucleic acid described herein to induce expression of type 1 IFN.

The invention in other aspects is a method for activating a natural killer (NK) cell. The method involves contacting an NK cell with an effective amount of an immunostimulatory nucleic acid described herein to activate the NK cell.

In yet other aspects the invention is a method for treating infection by administering to a subject having or at risk of developing an infection an effective amount of an immunostimulatory nucleic acid described herein, to treat or prevent the infection. In some embodiments the subject has or is at risk of developing an infection selected from the group consisting of a viral, bacterial, fungal and parasitic infection.

In certain embodiments the method involves administering an immunostimulatory nucleic acid of the invention alone to treat or prevent the infection. In certain embodiments the method according to this aspect of the invention further includes administering to the subject an antibiotic agent, which may be an antibacterial agent, an antiviral agent, an antifungal agent, or an antiparasitic agent.

In other aspects the invention is a method for treating an allergic condition by administering to a subject having or at risk of developing an allergic condition an effective amount of an immunostimulatory nucleic acid described herein, to treat or prevent the allergic condition. In some embodiments the allergic condition is allergic asthma. In one embodiment the allergic condition is asthma. In certain embodiments the method involves administering an immunostimulatory nucleic acid of the invention alone to treat or prevent the allergic condition. In certain embodiments the method according to this aspect of the invention further includes administering to the subject an asthma/allergy medicament e.g., steroids, antihistamines, and prostaglandin inducers.

A method for treating cancer is provided according to other aspects of the invention. The method involves administering to a subject having or at risk of developing a cancer an effective amount of an immunostimulatory nucleic acid described herein, to treat or prevent the cancer. In some embodiments the cancer is selected from the group consisting of basal cell carcinoma, biliary tract cancer; bladder cancer; bone cancer; brain and CNS cancer; breast cancer; cervical cancer; choriocarcinoma; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; leukemia; liver cancer; lung cancer (e.g. small cell and non-small cell); lymphoma including Hodgkin's and Non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; cancer of the urinary system, and other carcinomas and sarcomas In certain embodiments the method involves administering an immunostimulatory nucleic acid of the invention alone to treat the cancer. In certain embodiments the method according to this aspect of the invention further includes administering to the subject an anti-cancer medicament or treatment e.g., chemotherapeutic agents, radiation.

Each of the limitations of the invention can encompass various embodiments of the invention. It is, therefore, anticipated that each of the limitations of the invention involving any one element or combinations of elements can be included in each aspect of the invention.

BRIEF DESCRIPTION OF THE DRAWINGS

The following figures are provided for illustrative purposes only and are not required for understanding or practicing the invention.

FIG. 26 is a bar graph depicting amounts of IFN-α secretion (pg/ml) by PBMC following 24 hours of culture alone (w/o) or in the presence of the indicated ODN at the indicated concentrations (3.0 and 6.0 μg/ml).

DETAILED DESCRIPTION OF THE INVENTION

Figure 1:
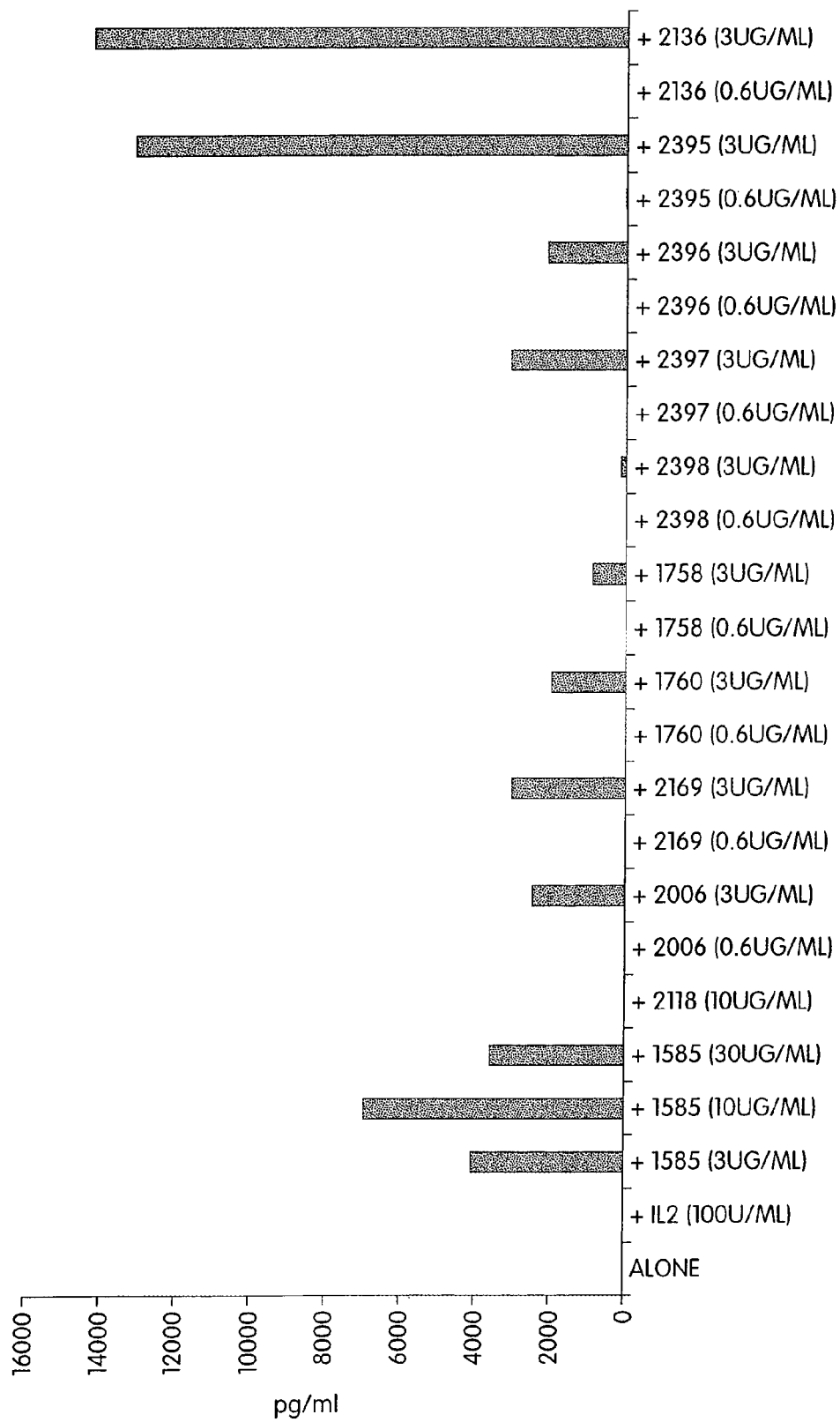
FIG. 1 is a bar graph depicting amounts of IFN-α (pg/ml) induced in human PBMCs after 24 hours of culture alone, with IL-2, or in the presence of the indicated ODN at the indicated concentrations.

It has been discovered that certain oligodeoxynucleotides (ODN), which contain at least two distinct motifs have unique and desirable stimulatory effects on cells of the immune system. Some of these ODN have both a traditional "stimulatory" CpG sequence and a "GC-rich" or "B-cell neutralizing" motif. These combination motif nucleic acids have immune stimulating effects that fall somewhere between those effects associated with traditional "class B" CpG ODN, which are strong inducers of B cell activation and dendritic cell (DC) activation, and those effects associated with a more recently described class of immune stimulatory nucleic acids ("class A" CpG ODN) which are strong inducers of IFN-α and natural killer (NK) cell activation but relatively poor inducers of B-cell and DC activation. Krieg A M et al. (1995) *Nature* 374:546-9; Ballas Z K et al. (1996) *J Immunol* 157: 1840-5; Yamamoto S et al. (1992) *J Immunol* 148:4072-6. While preferred class B CpG ODN often have phosphorothioate backbones and preferred class A CpG ODN have mixed or chimeric backbones, the new class of combination motif immune stimulatory nucleic acids may have either stabilized, e.g., phosphorothioate, chimeric, or phosphodiester backbones.

In one aspect the invention provides immune stimulatory nucleic acids belonging to this new class of combination motif immune-stimulatory nucleic acids. The B cell stimulatory domain is defined by a formula: 5' $X_1DCGHX_2$ 3'. D is a nucleotide other than C. C is cytosine. G is guanine. H is a nucleotide other than G.

$X_1$ and $X_2$ are any nucleic acid sequence 0 to 10 nucleotides long. $X_1$ may include a CG, in which case there is preferably a T immediately preceding this CG. In some embodiments DCG is TCG. $X_1$ is preferably from 0 to 6 nucleotides in length. In some embodiments $X_2$ does not contain any poly G or poly A motifs. In other embodiments the immunostimulatory nucleic acid has a poly-T sequence at the 5' end or at the 3' end. As used herein, "poly-A" or "poly-T" shall refer to a stretch of four or more consecutive A's or T's respectively, e.g., 5' AAAA 3' or 5' TTTT 3'.

As used herein, "poly-G end" shall refer to a stretch of four or more consecutive G's, e.g., 5' GGGG 3', occurring at the 5' end or the 3' end of a nucleic acid. As used herein, "poly-G nucleic acid" shall refer to a nucleic acid having the formula 5' $X_1X_2GGGX_3X_4$ 3' wherein $X_1$, $X_2$, $X_3$, and $X_4$ are nucleotides and preferably at least one of $X_3$ and $X_4$ is a G.

Some preferred designs for the B cell stimulatory domain under this formula comprise TTTTTCG, TCG, TTCG, TTTCG, TTTTCG, TCGT, TTCGT, TTTCGT, TCGTCGT.

The second motif of the nucleic acid is referred to as either P or N and is positioned immediately 5' to $X_1$ or immediately 3' to $X_2$.

N is a B-cell neutralizing sequence that begins with a CGG trinucleotide and is at least 10 nucleotides long. A B-cell neutralizing motif includes at least one CpG sequence in which the CG is preceded by a C or followed by a G (Krieg A M et al. (1998) *Proc Natl Acad Sci USA* 95:12631-12636) or is a CG containing DNA sequence in which the C of the CG is methylated. As used herein, "CpG" shall refer to a 5' cytosine (C) followed by a 3' guanine (G) and linked by a phosphate bond. At least the C of the 5' CG 3' must be unmethylated. Neutralizing motifs are motifs which has some degree of immunostimulatory capability when present in an otherwise non-stimulatory motif, but, which when present in the context of other immunostimulatory motifs serve to reduce the immunostimulatory potential of the other motifs.

P is a GC-rich palindrome containing sequence at least 10 nucleotides long. As used herein, "palindrome" and, equivalently, "palindromic sequence" shall refer to an inverted repeat, i.e., a sequence such as ABCDEE'D'C'B'A' in which A and A', B and B', etc., are bases capable of forming the usual Watson-Crick base pairs.

As used herein, "GC-rich palindrome" shall refer to a palindrome having a base composition of at least two-thirds G's and C's. In some embodiments the GC-rich domain is preferably 3' to the "B cell stimulatory domain". In the case of a 10-base long GC-rich palindrome, the palindrome thus contains at least 8 G's and C's. In the case of a 12-base long GC-rich palindrome, the palindrome also contains at least 8 G's and C's. In the case of a 14-mer GC-rich palindrome, at least ten bases of the palindrome are G's and C's. In some embodiments the GC-rich palindrome is made up exclusively of G's and C's.

In some embodiments the GC-rich palindrome has a base composition of at least 81 percent G's and C's. In the case of such a 10-base long GC-rich palindrome, the palindrome thus is made exclusively of G's and C's. In the case of such a 12-base long GC-rich palindrome, it is preferred that at least ten bases (83 percent) of the palindrome are G's and C's. In some preferred embodiments, a 12-base long GC-rich palindrome is made exclusively of G's and C's. In the case of a 14-mer GC-rich palindrome, at least twelve bases (86 percent) of the palindrome are G's and C's. In some preferred embodiments, a 14-base long GC-rich palindrome is made exclusively of G's and C's. The C's of a GC-rich palindrome can be unmethylated or they can be methylated.

In general this domain has at least 3 Cs and Gs, more preferably 4 of each, and most preferably 5 or more of each. The number of Cs and Gs in this domain need not be identical. It is preferred that the Cs and Gs are arranged so that they are able to form a self-complementary duplex, or palindrome, such as CCGCGCGG. This may be interrupted by As or Ts, but it is preferred that the self-complementarity is at least partially preserved as for example in the motifs CGACGT-TCGTCG (SEQ ID NO: 80) or CGGCGCCGTGCCG (SEQ ID NO: 81). When complementarity is not preserved, it is preferred that the non-complementary base pairs be TG. In a preferred embodiment there are no more than 3 consecutive bases that are not part of the palindrome, preferably no more than 2, and most preferably only 1. In some embodiments the GC-rich palindrome includes at least one CGG trimer, at least one CCG trimer, or at least one CGCG tetramer. In other embodiments the GC-rich palindrome is not CCCCCCGGGGGG (SEQ ID NO: 31) or GGGGGGC-CCCCC (SEQ ID NO: 32), CCCCCGGGGG (SEQ ID NO: 33) or GGGGGCCCCC (SEQ ID NO: 34).

At least one of the G's of the GC rich region may be substituted with an inosine (I). In some embodiments P includes more than one I.

In certain embodiments the immunostimulatory nucleic acid has one of the following formulas 5' NX$_1$DCGHX$_2$ 3', 5' X$_1$DCGHX$_2$N 3', 5' PX$_1$DCGHX$_2$ 3', 5' X$_1$DCGHX$_2$P 3', 5' X$_1$DCGHX$_2$PX$_3$ 3', 5' X$_1$DCGHPX$_3$ 3', 5' DCGHX$_2$PX$_3$ 3', 5' TCGHX$_2$PX$_3$ 3', 5' DCGHPX$_3$ 3', or 5' DCGHP 3'.

In other aspects the invention provides immune stimulatory nucleic acids which are defined by a formula: 5' N$_1$PyGN$_2$P 3'. N$_1$ is any sequence 1 to 6 nucleotides long. Py is a pyrimidine. G is guanine. N$_2$ is any sequence 0 to 30 nucleotides long. P is a GC-rich palindrome containing sequence at least 10 nucleotides long.

N$_1$ and N$_2$ may contain more than 50% pyrimidines, and more preferably more than 50% T. N$_1$ may include a CG, in which case there is preferably a T immediately preceding this CG. In some embodiments N$_1$PyG is TCG (such as ODN 5376, which has a 5' TCGG), and most preferably a TCGN$_2$, where N$_2$ is not G.

N$_1$PyGN$_2$P may include one or more inosine (I) nucleotides. Either the C or the G in N1 may be replaced by inosine, but the CpI is preferred to the IpG. For inosine substitutions such as IpG, the optimal activity may be achieved with the use of a "semi-soft" or chimeric backbone, where the linkage between the IG or the CI is phosphodiester. N$_1$ may include at least one CI, TCI, IG or TIG motif.

In certain embodiments N$_1$PyGN$_2$ is a sequence selected from the group consisting of TTTTTCG, TCG, TTCG, TTTCG, TTTTCG, TCGT, TTCGT, TTTCGT, and TCGTCGT.

In other aspects the invention provides immune stimulatory nucleic acids which are defined by a formula: 5' N$_1$PyG/IN$_2$P 3'. N$_1$ is any sequence 1 to 6 nucleotides long. Py is a pyrimidine, G/I refers to single nucleotide which is either a G or an I. G is guanine and I is inosine. N$_2$ is any sequence 0 to 30 nucleotides long. P is a GC or IC rich palindrome containing sequence at least 10 nucleotides long. In some embodiments N$_1$PyIN$_2$ is TCITCITTTT (SEQ ID NO: 47).

Some non-limiting examples of combination motif immune stimulatory nucleic acids, which are described by the formulas above, include the following:
TCGTCGTTTTCGGCGCGCGCCG (ODN 2395),
TCGTCGTTTTCGGCGGCCGCCG (ODN 2429),
TCGTCGTTTTCGGCGCGCCGCG (ODN 2430),
TCGTCGTTTTCGGCGCCGGCCG (ODN 2431),
TCGTCGTTTTCGGCCCGCGCGG (ODN 2432),
TCGTCGTTTTCGGCGCGCGCCGTTTTT (ODN 2452),
TCCTGACGTTCGGCGCGCGCCG (ODN 5315),
TZGTZGTTTTZGGZGZGZGZZG (ODN 5327, wherein Z is 5-methylcytosine),
TCCTGACGTTCGGCGCGCGCCC (ODN 2136),
TCGTCGTTTTCGGCGGCCGACG (ODN 5513),
TCGTCGTTTTCGTCGGCCGCCG (ODN 5514),
TCGTCGTTTTCGACGGCCGCCG (ODN 5515),
TCGTCGTTTTCGGCGGCCGTCG (ODN 5516),
TCGGCGCGCGCCGTCGTCGTTT (ODN 2451),
TCGTCGTTTCGACGGCCGTCG (ODN 20173),
TCGTCGTTTCGACGATCGTCG (ODN 20176),
TCGTCGTTTCGACGTACGTCG (ODN 20177),
TCGTCGCGACGGCCGTCG (ODN 20178),
TCGTCGCGACGATCGTCG (ODN 20179),
TCGTCGCGACGTACGTCG (ODN 20180),
TCGTTTTTTCGACGGCCGTCG (ODN 20184),
TCGTTTTTTCGACGATCGTCG (ODN 20185),
TCGTTTTTTCGACGTACGTCG (ODN 20186),
TIGTIGTTTTCGGCGGCCGCCG (ODN 5569, SEQ ID NO: 63), and
TCITCITTTTCGGCGGCCGCCG (ODN 5570, SEQ ID NO: 70).

As used herein, "nucleic acid" and "oligonucleotide" are used interchangeably and shall refer to mean multiple nucleotides (i.e., molecules comprising a sugar (e.g., ribose or deoxyribose) linked to a phosphate group and to an exchangeable organic base, which is either a substituted pyrimidine (e.g., cytosine (C), thymine (T) or uracil (U)) or a substituted purine (e.g., adenine (A) or guanine (G)). As used herein, the terms refer to oligoribonucleotides as well as oligodeoxyribonucleotides (ODN). The terms shall also include polynucleosides (i.e., a polynucleotide minus the phosphate) and any other organic base containing polymer. Nucleic acid molecules can be obtained from existing nucleic acid sources (e.g., genomic or cDNA), but are preferably synthetic (e.g., produced by nucleic acid synthesis).

The terms nucleic acid and oligonucleotide also encompass nucleic acids or oligonucleotides with substitutions or modifications, such as in the bases and/or sugars. For example, they include nucleic acids having backbone sugars which are covalently attached to low molecular weight organic groups other than a hydroxyl group at the 3' position and other than a phosphate group at the 5' position. Thus modified nucleic acids may include a 2'-O-alkylated ribose group. In addition, modified nucleic acids may include sugars such as arabinose instead of ribose. Thus the nucleic acids may be heterogeneous in backbone composition thereby containing any possible combination of polymer units linked together such as peptide-ucleic acids (which have amino acid backbone with nucleic acid bases). In some embodiments, the nucleic acids are homogeneous in backbone composition. Nucleic acids also include substituted purines and pyrimidines such as C-5 propyne modified bases. Wagner R W et al. (1996) *Nat Biotechnol* 14:840-4. Purines and pyrimidines include but are not limited to adenine, cytosine, guanine, thymidine, 5-methylcytosine, 2-aminopurine, 2-amino-6-chloropurine, 2,6-diaminopurine, hypoxanthine, and other naturally and non-naturally occurring nucleobases, substituted and unsubstituted aromatic moieties. Other such modifications are well known to those of skill in the art.

The immunostimulatory oligonucleotides of the instant invention can encompass various chemical modifications and substitutions, in comparison to natural RNA and DNA, involving a phosphodiester internucleoside bridge, a β-D-ribose unit and/or a natural nucleoside base (adenine, guanine, cytosine, thymine, uracil). Examples of chemical modifications are known to the skilled person and are described, for example, in Uhlmann E et al. (1990) *Chem Rev* 90:543; "Protocols for Oligonucleotides and Analogs" Synthesis and Properties & Synthesis and Analytical Techniques, S. Agrawal, Ed, Humana Press, Totowa, USA 1993; Crooke S T et al. (1996) *Annu Rev Pharmacol Toxicol* 36:107-129; and Hunziker J et al. (1995) *Mod Synth Methods* 7:331-417. An oligonucleotide according to the invention can have one or more modifications, wherein each modification is located at the a particular phosphodiester internucleoside bridge and/or at a particular β-D-ribose unit and/or at a particular natural nucleoside base position in comparison to an oligonucleotide of the same sequence which is composed of natural DNA or RNA.

For example, the invention relates to an oligonucleotide which comprises one or more modifications and wherein each modification is independently selected from:
a) the replacement of a sugar phosphate unit from the sugar phosphate backbone by another unit,
b) the replacement of a β-D-ribose unit by a modified sugar unit, and
c) the replacement of a natural nucleoside base by a modified nucleoside base.

More detailed examples for the chemical modification of an oligonucleotide are as follows.

A sugar phosphate unit (i.e., a β-D-ribose and phosphodiester internucleoside bridge together forming a sugar phosphate unit) from the sugar phosphate backbone (i.e., a sugar phosphate backbone is composed of sugar phosphate units) can be replaced by another unit, wherein the other unit is for example suitable to build up a "morpholino-derivative" oligomer (as described, for example, in Stirchak E P et al. (1989) *Nucleic Acids Res* 17:6129-41), that is, e.g., the replacement by a morpholino-derivative unit; or to build up a polyamide nucleic acid ("PNA"; as described for example, in Nielsen P E et al. (1994) *Bioconjug Chem* 5:3-7), that is, e.g., the replacement by a PNA backbone unit, e.g., by 2-aminoethylglycine.

A β-ribose unit or a β-D-2'-deoxyribose unit can be replaced by a modified sugar unit, wherein the modified sugar unit is for example selected from β-D-ribose, α-D-2'-deoxyribose, L-2'-deoxyribose, 2'-F-2'-deoxyribose, 2'-O—($C_1$-$C_6$)alkyl-ribose, preferably 2'-O—($C_1$-$C_6$)alkyl-ribose is 2'-O-methylribose, 2'-O—($C_2$-$C_6$)alkenyl-ribose, 2'-[O—($C_1$-$C_6$)alkyl-O—($C_1$-$C_6$)alkyl]-ribose, 2'-NH$_2$-2'-deoxyribose, β-D-xylo-furanose, α-arabinofuranose, 2,4-dideoxy-β-D-erythro-hexo-pyranose, and carbocyclic (described, for example, in Froehler J (1992) *Am Chem Soc* 114:8320) and/or open-chain sugar analogs (described, for example, in Vandendriessche et al. (1993) *Tetrahedron* 49:7223) and/or bicyclo-sugar analogs (described, for example, in Tarkov M et al. (1993) *Helv Chim Acta* 76:481).

A natural nucleoside base can be replaced by a modified nucleoside base, wherein the modified nucleoside base is for example selected from hypoxanthine, uracil, dihydrouracil, pseudouracil, 2-thiouracil, 4-thiouracil, 5-aminouracil, 5-($C_1$-$C_6$)-alkyluracil, 5-($C_2$-$C_6$)-alkenyluracil, 5-($C_2$-$C_6$)-alkynyluracil, 5-(hydroxymethyl)uracil, 5-chlorouracil, 5-fluorouracil, 5-bromouracil, 5-hydroxycytosine, 5-($C_1$-$C_6$)-alkylcytosine, 5-($C_2$-$C_6$)-alkenylcytosine, 5-($C_2$-$C_6$)-alkynylcytosine, 5-chlorocytosine, 5-fluorocytosine, 5-bromocytosine, $N^2$-dimethylguanosine, 2,4-diamino-purine, 8-azapurine, a substituted 7-deazapurine, preferably 7-deaza-7-substituted and/or 7-deaza-8-substituted purine or other modifications of a natural nucleoside bases. This list is meant to be exemplary and is not to be interpreted to be limiting.

As used herein, "immune stimulatory nucleic acid" and, equivalently, "immunostimulatory nucleic acid" shall refer to a ribonucleic acid or deoxyribonucleic acid molecule, derivative or analog thereof, characterized by its capacity to induce a functional aspect of a cell of the immune system. Such functional aspect of a cell of the immune system can include, for example, elaboration of a cytokine or chemokine, expression of a cell surface marker, secretion of an antibody, proliferation, or other activity in response to or directed against an antigen or antigen-bearing membrane-bound target.

For use in the instant invention, the nucleic acids of the invention can be synthesized de novo using any of a number of procedures well known in the art, for example, the β-cyanoethyl phosphoramidite method (Beaucage S L and Caruthers M H (1981) *Tetrahedron Lett* 22:1859); and the nucleoside H-phosphonate method (Garegg et al. (1986) *Tetrahedron Lett* 27:4051-4; Froehler et al. (1986) *Nucl Acid Res* 14:5399-407; Garegg et al. (1986) *Tetrahedron Lett* 27:4055-8; Gaffney et al. (1988) *Tetrahedron Lett* 29:2619-22). These chemistries can be performed by a variety of automated nucleic acid synthesizers available in the market. These nucleic acids are referred to as synthetic nucleic acids. Alternatively, nucleic acids of the invention can be produced on a large scale in plasmids, (see Sambrook T et al., "Molecular Cloning: A Laboratory Manual", Cold Spring Harbor Laboratory Press, New York, 1989) and separated into smaller pieces or administered whole. Nucleic acids can be prepared from existing nucleic acid sequences (e.g., genomic or cDNA) using known techniques, such as those employing restriction enzymes, exonucleases or endonucleases. Nucleic acids prepared in this manner are referred to as isolated nucleic acids. An isolated nucleic acid generally refers to a nucleic acid which is separated from components which it is normally associated with in nature. As an example, an isolated nucleic acid may be one which is separated from a cell, from a nucleus, from mitochondria or from chromatin. The combination motif nucleic acids of the instant invention encompass both synthetic and isolated combination motif nucleic acids.

For use in vivo, the combination motif immunostimulatory nucleic acids may optionally be relatively resistant to degradation (e.g., are stabilized). A "stabilized nucleic acid molecule" shall mean a nucleic acid molecule that is relatively resistant to in vivo degradation (e.g., via an exonuclease or endonuclease). Nucleic acid stabilization can be accomplished via phosphate backbone modifications. Preferred stabilized nucleic acids of the instant invention have a modified backbone. It has been demonstrated that modification of the nucleic acid backbone provides enhanced activity of the combination motif immunostimulatory nucleic acids when administered in vivo. Combination motif immunostimulatory nucleic acids having phosphorothioate linkages in some instances provide maximal activity and protect the nucleic acid from degradation by intracellular exonucleases and endonucleases. Other modified nucleic acids include modified phosphodiester nucleic acids, combinations of phosphodiester and phosphorothioate nucleic acids (i.e., chimeric), methylphosphonate, methylphosphorothioate, phosphorodithioate, p-ethoxy, and combinations thereof.

Modified backbones such as phosphorothioates may be synthesized using automated techniques employing either phosphoramidate or H-phosphonate chemistries. Aryl- and alkyl-phosphonates can be made, e.g., as described in U.S. Pat. No. 4,469,863; and alkylphosphotriesters (in which the charged oxygen moiety is alkylated as described in U.S. Pat. No. 5,023,243 and European Patent No. 092,574) can be prepared by automated solid phase synthesis using commercially available reagents. Methods for making other DNA backbone modifications and substitutions have been described. Uhlmann E and Peyman A (1990) *Chem Rev* 90:544; Goodchild J (1990) *Bioconjugate Chem* 1:165.

Other stabilized nucleic acids include: nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Nucleic acids which contain diol, such as tetraethyleneglycol or hexaethyleneglycol, at either or both termini have also been shown to be substantially resistant to nuclease degradation.

In other embodiments the immunostimulatory nucleic acids may have phosphodiester or chimeric e.g., soft or semi-soft backbones. A chimeric backbone includes a combination of phosphodiester and modified backbone linkages. A chimeric oligonucleotide, for instance, may be a soft oligonucleotide or a semi-soft oligonucleotide.

A soft oligonucleotide is an immunostimulatory oligonucleotide having a partially stabilized backbone, in which phosphodiester or phosphodiester-like internucleoside linkages occur only within and immediately adjacent to at least one internal pyrimidine nucleoside-guanosine (YG) dinucleotide. The at least one internal YG dinucleotide itself has a phosphodiester or phosphodiester-like internucleoside linkage. A phosphodiester or phosphodiester-like internucleoside linkage occurring immediately adjacent to the at least one internal YG dinucleotide can be 5', 3', or both 5' and 3' to the at least one internal YG dinucleotide. Preferably a phosphodiester or phosphodiester-like internucleoside linkage occurring immediately adjacent to the at least one internal YG dinucleotide is itself an internal internucleoside linkage. Thus for a sequence $N_1YGN_2$, wherein $N_1$ and $N_2$ are each, independent of the other, any single nucleotide, the YG dinucleotide has a phosphodiester or phosphodiester-like internucleoside linkage, and in addition (a) $N_1$ and Y are linked by a phosphodiester or phosphodiester-like internucleoside linkage when $N_1$ is an internal nucleotide, (b) G and $N_2$ are linked by a phosphodiester or phosphodiester-like internucleoside linkage when $N_2$ is an internal nucleotide, or (c) $N_1$ and Y are linked by a phosphodiester or phosphodiester-like internucleoside linkage when $N_1$ is an internal nucleotide and G and $N_2$ are linked by a phosphodiester or phosphodiester-like internucleoside linkage when $N_2$ is an internal nucleotide.

A semi-soft oligonucleotide is an immunostimulatory oligonucleotide having a partially stabilized backbone, in which phosphodiester or phosphodiester-like internucleoside linkages occur only within at least one internal pyrimidine nucleoside-guanosine (YG) dinucleotide. Semi-soft oligonucleotides can have a number of advantages over immunostimulatory oligonucleotides with fully stabilized backbones. For instance, semi-soft oligonucleotides may possess increased immunostimulatory potency relative to corresponding fully stabilized immunostimulatory oligonucleotides.

The immunostimulatory nucleic acids may be used to treat a subject to induce an immune response or treat an immune related disease such as, for example, infectious disease, cancer, and allergic disorders. As used herein, "subject" shall refer to a human or vertebrate animal including, but not limited to, a dog, cat, horse, cow, pig, sheep, goat, chicken, monkey, rabbit, rat, mouse, etc.

As used herein, the terms "treat", "treating" and "treated" shall refer to a prophylactic treatment which increases the resistance of a subject to developing a disease or, in other words, decreases the likelihood that the subject will develop a disease or slows the development of the disease, as well as to a treatment after the subject has developed the disease in order to fight the disease, e.g., reduce or eliminate it altogether or prevent it from becoming worse. For example, when used with respect to the treatment of an infectious disease the terms refer to a prophylactic treatment which increases the resistance of a subject to a microorganism or, in other words, decreases the likelihood that the subject will develop an infectious disease to the microorganism, as well as to a treatment after the subject has been infected in order to fight the infectious disease, e.g., reduce or eliminate it altogether or prevent it from becoming worse. When used with respect to a disease such as cancer the terms refer to the prevention or delay of the development of a cancer, reducing the symptoms of cancer, and/or inhibiting or slowing the growth of an established cancer.

Thus, the nucleic acids are useful as prophylactics for the induction of immunity of a subject at risk of developing an infection with an infectious organism or a subject at risk of developing an allergic disorder or cancer. A "subject at risk" as used herein is a subject who has any risk of exposure to an infection-causing infectious pathogen, exposure to an allergen, or developing cancer. For instance, a subject at risk may be a subject who is planning to travel to an area where a particular type of infectious agent or allergen is found or it may be a subject who through lifestyle or medical procedures is exposed to bodily fluids which may contain infectious organisms or even any subject living in an area that an infectious organism or an allergen has been identified and is exposed directly to the infectious agent or allergen. It also may be a subject at risk of biowarfare such as military personnel or those living in areas at risk of terrorist attack. Subjects at risk of developing infection also include general populations to which a medical agency recommends vaccination with a particular infectious organism antigen. If the antigen is an allergen and the subject develops allergic responses to that particular antigen and the subject is exposed to the antigen, i.e., during pollen season, then that subject is at risk of exposure to the antigen. Subjects at risk of developing cancer include those with a genetic predisposition or previously treated for cancer, and those exposed to carcinogens such as tobacco, asbestos, and other chemical toxins or excessive sunlight and other types of radiation. The nucleic acids are also useful as therapeutics in the treatment of infectious disease, cancer and allergic disorders.

A "subject having an infection" is a subject that has been exposed to an infectious pathogen and has acute or chronic detectable levels of the pathogen in the body. The nucleic acids can be used alone, or in conjunction with other therapeutic agents such as an antigen or an antimicrobial medicament to mount an immune response that is capable of reducing the level of or eradicating the infectious pathogen. The method entails administering to a subject having or at risk of developing an infection an effective amount of a combination motif immune stimulatory nucleic acid of the invention to treat the infection. The method can be used to treat viral, bacterial, fungal, and parasitic infections in human and non-human vertebrate subjects.

As used herein, "infection" and, equivalently, "infectious disease" shall refer to a disease arising from the presence of a foreign microorganism in the body of a subject. A foreign microorganism may be a virus, a bacterium, a fungus, or a parasite.

Examples of infectious viruses include: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes viruses); Poxviridae (variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Examples of infectious bacteria include: *Actinomyces israelii, Bacillus anthracis*, Bacteroides spp., *Borrelia burgdorferi, Chlamydia trachomatis, Clostridium perfringens, Clostridium tetani, Corynebacterium diphtheriae*, Corynebacterium spp., *Enterobacter aerogenes*, Enterococcus sp., *Erysipelothrix rhusiopathiae, Fusobacterium nucleatum, Haemophilus influenzae, Helicobacter pyloris, Klebsiella pneumoniae, Legionella pneumophilia*, Leptospira, *Listeria monocytogenes*, Mycobacteria spp. (e.g., *M. tuberculosis, M. avium, M. intracellulare, M. kansasii, M. gordonae*), *Neisseria gonorrhoeae, Neisseria meningitidis, Pasturella multocida*, pathogenic Campylobacter sp., *Staphylococcus aureus, Streptobacillus moniliformis*, Streptococcus (anaerobic spp.), Streptococcus (viridans group), *Streptococcus agalactiae* (Group B Streptococcus), *Streptococcus bovis, Streptococcus faecalis, Streptococcus pneumoniae, Streptococcus pyogenes* (Group A Streptococcus), *Treponema pallidium*, and *Treponema pertenue*.

Examples of infectious fungi include: *Candida albicans, Cryptococcus neoformans, Histoplasma capsulatum, Coccidioides immitis*, and *Blastomyces dermatitidis*.

Other infectious organisms (i.e., protists) include Plasmodium spp. such as *Plasmodium falciparum, Plasmodium malariae, Plasmodium ovale*, and *Plasmodium vivax*, and *Toxoplasma gondii*. Blood-borne and/or tissue parasites include Plasmodium spp., *Babesia microti, Babesia divergens, Leishmania tropica*, Leishmania spp., *Leishmania braziliensis, Leishmania donovani, Trypanosoma gambiense* and *Trypanosoma rhodesiense* (African sleeping sickness), *Trypanosoma cruzi* (Chagas' disease), and *Toxoplasma gondii*.

The foregoing lists of viruses, bacteria, fungi, and other infectious microorganisms is understood to be representative and not limiting. Other medically relevant microorganisms have been described extensively in the literature, e.g., see C. G. A Thomas, *Medical Microbiology*, Bailliere Tindall, Great Britain 1983, the entire contents of which is hereby incorporated by reference.

Although many of the microbial agents described above relate to human disorders, the invention is also useful for treating non-human vertebrates. Non-human vertebrates are also capable of developing infections which can be prevented or treated with the immunostimulatory nucleic acids disclosed herein. For instance, in addition to the treatment of infectious human diseases, the methods of the invention are useful for treating infections of animals.

Infectious viruses of both human and non-human vertebrates include retroviruses, RNA viruses and DNA viruses. This group of retroviruses includes both simple retroviruses and complex retroviruses. The simple retroviruses include the subgroups of B-type retroviruses, C-type retroviruses and D-type retroviruses. An example of a B-type retrovirus is mouse mammary tumor virus (MMTV). The C-type retroviruses include subgroups C-type group A (including Rous sarcoma virus (RSV), avian leukemia virus (ALV), and avian myeloblastosis virus (AMV)) and C-type group B (including feline leukemia virus (FeLV), gibbon ape leukemia virus (GALV), spleen necrosis virus (SNV), reticuloendotheliosis virus (RV) and simian sarcoma virus (SSV)). The D-type retroviruses include Mason-Pfizer monkey virus (MPMV) and simian retrovirus type 1 (SRV-1). The complex retroviruses include the subgroups of lentiviruses, T-cell leukemia viruses and the foamy viruses. Lentiviruses include HIV-1, but also include HIV-2, SIV, Visna virus, feline immunodeficiency virus (FIV), and equine infectious anemia virus (EIAV). The T-cell leukemia viruses include HTLV-1, HTLV-II, simian T-cell leukemia virus (STLV), and bovine leukemia virus (BLV). The foamy viruses include human foamy virus (HFV), simian foamy virus (SFV) and bovine foamy virus (BFV).

Examples of other RNA viruses that are infectious agents in vertebrate animals include, but are not limited to, members of the family Reoviridae, including the genus Orthoreovirus (multiple serotypes of both mammalian and avian retroviruses), the genus Orbivirus (Bluetongue virus, Eugenangee virus, Kemerovo virus, African horse sickness virus, and Colorado Tick Fever virus), the genus Rotavirus (human rotavirus, Nebraska calf diarrhea virus, simian rotavirus, bovine or ovine rotavirus, avian rotavirus); the family Picornaviridae, including the genus Enterovirus (poliovirus, Coxsackie virus A and B, enteric cytopathic human orphan (ECHO) viruses, hepatitis A virus, Simian enteroviruses, Murine encephalomyelitis (ME) viruses, Poliovirus muris, Bovine enteroviruses, Porcine enteroviruses, the genus Cardiovirus (Encephalomyocarditis virus (EMC), Mengovirus), the genus Rhinovirus (Human rhinoviruses including at least 113 subtypes; other rhinoviruses), the genus Apthovirus (Foot and Mouth disease virus (FMDV); the family Calciviridae, including Vesicular exanthema of swine virus, San Miguel sea lion virus, Feline picornavirus and Norwalk virus; the family Togaviridae, including the genus Alphavirus (Eastern equine encephalitis virus, Semliki forest virus, Sindbis virus, Chikungunya virus, O'Nyong-Nyong virus, Ross river virus, Venezuelan equine encephalitis virus, Western equine encephalitis virus), the genus Flavivirus (Mosquito-borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus Pestivirus (Mucosal disease virus, Hog cholera virus, Border disease virus); the family Bunyaviridae, including the genus Bunyvirus (Bunyamwera and related viruses, California encephalitis group viruses), the genus Phlebovirus (Sandfly fever Sicilian virus, Rift Valley fever virus), the genus Nairovirus (Crimean-Congo hemorrhagic fever virus, Nairobi sheep disease virus), and the genus Uukuvirus (Uukuniemi and related viruses); the family Orthomyxoviridae, including the genus Influenza virus (Influenza virus type A, many human subtypes); Swine influenza virus, and Avian and Equine Influenza viruses; influenza type B (many human subtypes), and influenza type C (possible separate genus); the family paramyxoviridae, including the genus Paramyxovirus (Parainfluenza virus type 1, Sendai virus, Hemadsorption virus, Parainfluenza viruses types 2 to 5, Newcastle Disease Virus, Mumps virus), the genus Morbillivirus (Measles virus, subacute sclerosing panencephalitis virus, distemper virus, Rinderpest virus), the genus Pneumovirus (respiratory syncytial virus (RSV), Bovine respiratory syncytial virus and Pneumonia virus); the family Rhabdoviridae, including the genus Vesiculovirus (VSV), Chandipura virus, Flanders-Hart Park virus), the genus Lyssavirus (Rabies virus), fish Rhabdoviruses, and two probable Rhabdoviruses (Marburg virus and Ebola virus); the family Arenaviridae, including Lymphocytic choriomeningitis virus (LCM), Tacaribe virus complex, and Lassa virus; the family Coronoaviridae, including Infectious Bronchitis Virus (IBV), Hepatitis virus, Human enteric corona virus, and Feline infectious peritonitis (Feline coronavirus).

Illustrative DNA viruses that are infectious agents in vertebrate animals include, but are not limited to, the family Poxviridae, including the genus Orthopoxvirus (Variola major, Variola minor, Monkey pox Vaccinia, Cowpox, Buffalopox, Rabbitpox, Ectromelia), the genus Leporipoxvirus (Myxoma, Fibroma), the genus Avipoxvirus (Fowlpox, other avian poxvirus), the genus Capripoxvirus (sheep-pox, goat-pox), the genus Suipoxvirus (Swinepox), the genus Parapoxvirus (contagious pustular dermatitis virus, pseudocowpox, bovine papular stomatitis virus); the family Iridoviridae (African swine fever virus, Frog viruses 2 and 3, Lymphocystis virus of fish); the family Herpesviridae, including the alpha-Herpesviruses (Herpes Simplex Types 1 and 2, Varicella-Zoster, Equine abortion virus, Equine herpes virus 2 and 3, pseudorabies virus, infectious bovine keratoconjunctivitis virus, infectious bovine rhinotracheitis virus, feline rhinotracheitis virus, infectious laryngotracheitis virus), the Beta-herpesviruses (Human cytomegalovirus and cytomegaloviruses of swine and monkeys); the gamma-herpesviruses (Epstein-Barr virus (EBV), Marek's disease virus, Herpes saimiri, Herpesvirus ateles, Herpesvirus sylvilagus, guinea pig herpes virus, Lucke tumor virus); the family Adenoviridae, including the genus Mastadenovirus (Human subgroups A, B, C, D, E and ungrouped; simian adenoviruses (at least 23 serotypes), infectious canine hepatitis, and adenoviruses of cattle, pigs, sheep, frogs and many other species, the genus Aviadenovirus (Avian adenoviruses); and non-cultivatable adenoviruses; the family Papoviridae, including the genus Papillomavirus (Human papilloma viruses, bovine papilloma viruses, Shope rabbit papilloma virus, and various pathogenic papilloma viruses of other species), the genus Polyomavirus (polyomavirus, Simian vacuolating agent (SV-40), Rabbit vacuolating agent (RKV), K virus, BK virus, JC virus, and other primate polyoma viruses such as Lymphotrophic papilloma virus); the family Parvoviridae including the genus Adeno-associated viruses, the genus Parvovirus (Feline panleukopenia virus, bovine parvovirus, canine parvovirus, Aleutian mink disease virus, etc). Finally, DNA viruses may include viruses which do not fit into the above families, such as Kuru and Creutzfeldt-Jacob disease viruses and chronic infectious neuropathic agents (CHINA virus).

The nucleic acids may be administered to a subject with an anti-microbial agent. An anti-microbial agent, as used herein, refers to a naturally-occurring, synthetic, or semi-synthetic compound which is capable of killing or inhibiting infectious microorganisms. The type of anti-microbial agent useful according to the invention will depend upon the type of microorganism with which the subject is infected or at risk of becoming infected. Anti-microbial agents include but are not limited to anti-bacterial agents, anti-viral agents, anti-fungal agents and anti-parasitic agents. Phrases such as "anti-infective agent", "anti-bacterial agent", "anti-viral agent", "anti-fungal agent", "anti-parasitic agent" and "parasiticide" have well-established meanings to those of ordinary skill in the art and are defined in standard medical texts. Briefly, anti-bacterial agents kill or inhibit bacteria, and include antibiotics as well as other synthetic or natural compounds having similar functions. Antibiotics are low molecular weight molecules which are produced as secondary metabolites by cells, such as microorganisms. In general, antibiotics interfere with one or more bacterial functions or structures which are specific for the microorganism and which are not present in host cells.

Anti-viral agents can be isolated from natural sources or synthesized and are useful for killing or inhibiting viruses. Anti-fungal agents are used to treat superficial fungal infections as well as opportunistic and primary systemic fungal infections. Anti-parasite agents kill or inhibit parasites.

Antibacterial agents kill or inhibit the growth or function of bacteria. A large class of antibacterial agents is antibiotics. Antibiotics, which are effective for killing or inhibiting a wide range of bacteria, are referred to as broad spectrum antibiotics. Other types of antibiotics are predominantly effective against the bacteria of the class gram-positive or gram-negative. These types of antibiotics are referred to as narrow spectrum antibiotics. Other antibiotics which are effective against a single organism or disease and not against other types of bacteria, are referred to as limited spectrum antibiotics. Antibacterial agents are sometimes classified based on their primary mode of action. In general, antibacterial agents are cell wall synthesis inhibitors, cell membrane inhibitors, protein synthesis inhibitors, nucleic acid synthesis or functional inhibitors, and competitive inhibitors.

Antiviral agents are compounds which prevent infection of cells by viruses or replication of the virus within the cell. There are many fewer antiviral drugs than antibacterial drugs because the process of viral replication is so closely related to DNA replication within the host cell, that non-specific antiviral agents would often be toxic to the host. There are several stages within the process of viral infection which can be blocked or inhibited by antiviral agents. These stages include, attachment of the virus to the host cell (immunoglobulin or binding peptides), uncoating of the virus (e.g., amantadine), synthesis or translation of viral mRNA (e.g., interferon), replication of viral RNA or DNA (e.g., nucleoside analogues), maturation of new virus proteins (e.g., protease inhibitors), and budding and release of the virus.

Nucleotide analogues are synthetic compounds which are similar to nucleotides, but which have an incomplete or abnormal deoxyribose or ribose group. Once the nucleotide analogues are in the cell, they are phosphorylated, producing the triphosphate formed which competes with normal nucleotides for incorporation into the viral DNA or RNA. Once the triphosphate form of the nucleotide analogue is incorporated into the growing nucleic acid chain, it causes irreversible association with the viral polymerase and thus chain termination. Nucleotide analogues include, but are not limited to, acyclovir (used for the treatment of herpes simplex virus and varicella-zoster virus), gancyclovir (useful for the treatment of cytomegalovirus), idoxuridine, ribavirin (useful for the treatment of respiratory syncitial virus), dideoxyinosine, dideoxycytidine, and zidovudine (azidothymidine).

Immunoglobulin therapy is used for the prevention of viral infection. Immunoglobulin therapy for viral infections is different than bacterial infections, because rather than being antigen-specific, the immunoglobulin therapy functions by binding to extracellular virions and preventing them from attaching to and entering cells which are susceptible to the viral infection. The therapy is useful for the prevention of viral infection for the period of time that the antibodies are present in the host. In general there are two types of immunoglobulin therapies, normal immunoglobulin therapy and hyper-immunoglobulin therapy. Normal immune globulin therapy utilizes a antibody product which is prepared from the serum of normal blood donors and pooled. This pooled product contains low titers of antibody to a wide range of human viruses, such as hepatitis A, parvovirus, enterovirus (especially in neonates). Hyper-immune globulin therapy utilizes antibodies which are prepared from the serum of individuals who have high titers of an antibody to a particular virus. Those antibodies are then used against a specific virus. Examples of hyper-immune globulins include zoster immune globulin (useful for the prevention of varicella in immuno-compromised children and neonates), human rabies immunoglobulin (useful in the post-exposure prophylaxis of a subject bitten by a rabid animal), hepatitis B immune globulin (useful in the prevention of hepatitis B virus, especially in a subject exposed to the virus), and RSV immune globulin (useful in the treatment of respiratory syncitial virus infections).

Another type of immunoglobulin therapy is active immunization. This involves the administration of antibodies or antibody fragments to viral surface proteins. Two types of vaccines which are available for active immunization of hepatitis B include serum-derived hepatitis B antibodies and recombinant hepatitis B antibodies. Both are prepared from hepatitis B surface antigen (HbsAg). The antibodies are administered in three doses to subjects at high risk of infection with hepatitis B virus, such as health care workers, sexual partners of chronic carriers, and infants.

Anti-fungal agents are useful for the treatment and prevention of infective fungi. Anti-fungal agents are sometimes classified by their mechanism of action. Some anti-fungal agents function as cell wall inhibitors by inhibiting glucose synthase. These include, but are not limited to, basiungin/ECB. Other anti-fungal agents function by destabilizing membrane integrity. These include, but are not limited to, immidazoles, such as clotrimazole, sertaconzole, fluconazole, itraconazole, ketoconazole, miconazole, and voriconacole, as well as FK 463, amphotericin B, BAY 38-9502, MK 991, pradimicin, UK 292, butenafine, and terbinafine. Other anti-fungal agents function by breaking down chitin (e.g., chitinase) or immunosuppression (501 cream).

The immunostimulatory nucleic acids may be used, either alone or in combination with an anti-cancer therapy, for the treatment of cancer. The method entails administering to a subject having or at risk of developing cancer an effective amount of a combination motif immune stimulatory nucleic acid of the invention to treat cancer.

A "subject having a cancer" is a subject that has detectable cancerous cells. The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g., small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas. In one embodiment the cancer is hairy cell leukemia, chronic myelogenous leukemia, cutaneous T-cell leukemia, multiple myeloma, follicular lymphoma, malignant melanoma, squamous cell carcinoma, renal cell carcinoma, prostate carcinoma, bladder cell carcinoma, or colon carcinoma.

Cancer is one of the leading causes of death in companion animals (i.e., cats and dogs). Malignant disorders commonly diagnosed in dogs and cats include but are not limited to lymphosarcoma, osteosarcoma, mammary tumors, mastocytoma, brain tumor, melanoma, adenosquamous carcinoma, carcinoid lung tumor, bronchial gland tumor, bronchiolar adenocarcinoma, fibroma, myxochondroma, pulmonary sarcoma, neurosarcoma, osteoma, papilloma, retinoblastoma, Ewing's sarcoma, Wilms' tumor, Burkitt's lymphoma, microglioma, neuroblastoma, osteoclastoma, oral neoplasia, fibrosarcoma, osteosarcoma and rhabdomyosarcoma. Other neoplasms in dogs include genital squamous cell carcinoma, transmissible venereal tumor, testicular tumor, seminoma, Sertoli cell tumor, hemangiopericytoma, histiocytoma, chloroma (granulocytic sarcoma), corneal papilloma, corneal squamous cell carcinoma, hemangiosarcoma, pleural mesothelioma, basal cell tumor, thymoma, stomach tumor, adrenal gland carcinoma, oral papillomatosis, hemangioendothelioma and cystadenoma. Additional malignancies diagnosed in cats include follicular lymphoma, intestinal lymphosarcoma, fibrosarcoma and pulmonary squamous cell carcinoma. The ferret, an ever-more popular house pet, is known to develop insulinoma, lymphoma, sarcoma, neuroma, pancreatic islet cell tumor, gastric MALT lymphoma and gastric adenocarcinoma.

The immunostimulatory nucleic acids may also be administered in conjunction with an anti-cancer therapy. Anti-cancer therapies include cancer medicaments, radiation and surgical procedures. As used herein, a "cancer medicament" refers to an agent which is administered to a subject for the purpose of treating a cancer. Various types of medicaments for the treatment of cancer are described herein. For the purpose of this specification, cancer medicaments are classified as chemotherapeutic agents, immunotherapeutic agents, cancer vaccines, hormone therapy, and biological response modifiers.

Cancer medicaments function in a variety of ways. Some cancer medicaments work by targeting physiological mechanisms that are specific to tumor cells. Examples include the targeting of specific genes and their gene products (i.e., proteins primarily) which are mutated in cancers. Such genes include but are not limited to oncogenes (e.g., Ras, Her2, bcl-2), tumor suppressor genes (e.g., EGF, p53, Rb), and cell cycle targets (e.g., CDK4, p21, telomerase). Cancer medicaments can alternately target signal transduction pathways and molecular mechanisms which are altered in cancer cells. Targeting of cancer cells via the epitopes expressed on their cell surface is accomplished through the use of monoclonal antibodies. This latter type of cancer medicament is generally referred to herein as immunotherapy.

Other cancer medicaments target cells other than cancer cells. For example, some medicaments prime the immune system to attack tumor cells (i.e., cancer vaccines). Still other medicaments, called angiogenesis inhibitors, function by attacking the blood supply of solid tumors. Since the most malignant cancers are able to metastasize (i.e., exist the primary tumor site and seed a distal tissue, thereby forming a secondary tumor), medicaments that impede this metastasis are also useful in the treatment of cancer. Angiogenic mediators include basic FGF, VEGF, angiopoietins, angiostatin, endostatin, TNF-α, TNP-470, thrombospondin-1, platelet factor 4, CAI, and certain members of the integrin family of proteins. One category of this type of medicament is a metalloproteinase inhibitor, which inhibits the enzymes used by the cancer cells to exist the primary tumor site and extravasate into another tissue.

Immunotherapeutic agents are medicaments which derive from antibodies or antibody fragments which specifically bind or recognize a cancer antigen. As used herein a cancer antigen is broadly defined as an antigen expressed by a cancer cell. Preferably, the antigen is expressed at the cell surface of the cancer cell. Even more preferably, the antigen is one which is not expressed by normal cells, or at least not expressed to the same level as in cancer cells. Antibody-based immunotherapies may function by binding to the cell surface of a cancer cell and thereby stimulate the endogenous immune system to attack the cancer cell. Another way in which antibody-based therapy functions is as a delivery system for the specific targeting of toxic substances to cancer cells. Antibodies are usually conjugated to toxins such as ricin (e.g., from castor beans), calicheamicin and maytansinoids, to radioactive isotopes such as Iodine-131 and Yttrium-90, to chemotherapeutic agents (as described herein), or to biological response modifiers. In this way, the toxic substances can be concentrated in the region of the cancer and non-specific toxicity to normal cells can be minimized. In addition to the use of antibodies which are specific for cancer antigens, antibodies which bind to vasculature, such as those which bind to endothelial cells, are also useful in the invention. This is because generally solid tumors are dependent upon newly formed blood vessels to survive, and thus most tumors are capable of recruiting and stimulating the growth of new blood vessels. As a result, one strategy of many cancer medicaments is to attack the blood vessels feeding a tumor and/or the connective tissues (or stroma) supporting such blood vessels.

The use of immunostimulatory nucleic acids in conjunction with immunotherapeutic agents such as monoclonal antibodies is able to increase long-term survival through a number of mechanisms including significant enhancement of antibody-dependent cellular cytotoxicity (ADCC), activation of NK cells and an increase in IFN-α levels. ADCC can be performed using a immunostimulatory nucleic acid in combination with an antibody specific for a cellular target, such as a cancer cell. When the immunostimulatory nucleic acid is administered to a subject in conjunction with the antibody the subject's immune system is induced to kill the tumor cell. The antibodies useful in the ADCC procedure include antibodies which interact with a cell in the body. Many such antibodies specific for cellular targets have been described in the art and many are commercially available. The nucleic acids when used in combination with monoclonal antibodies serve to reduce the dose of the antibody required to achieve a biological result.

Other types of chemotherapeutic agents which can be used according to the invention include Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erythropoietin, Hexamethylmelamine (HMM), Interleukin 2, Mitoguazone (methyl-GAG; methyl glyoxal bis-guanylhydrazone; MGBG), Pentostatin (2'deoxycoformycin), Semustine (methyl-CCNU), Teniposide (VM-26) and Vindesine sulfate.

Cancer vaccines are medicaments which are intended to stimulate an endogenous immune response against cancer cells. Currently produced vaccines predominantly activate the humoral immune system (i.e., the antibody dependent immune response). Other vaccines currently in development are focused on activating the cell-mediated immune system including cytotoxic T lymphocytes which are capable of killing tumor cells. Cancer vaccines generally enhance the presentation of cancer antigens to both antigen presenting cells (e.g., macrophages and dendritic cells) and/or to other immune cells such as T cells, B cells, and NK cells. In some instances, cancer vaccines may be used along with adjuvants, such as those described above.

Some cancer cells are antigenic and thus can be targeted by the immune system. In one aspect, the combined administration of immunostimulatory nucleic acids and cancer medicaments, particularly those which are classified as cancer immunotherapies, is useful for stimulating a specific immune response against a cancer antigen. used herein, the terms "cancer antigen" and "tumor antigen" are used interchangeably to refer to antigens which are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses. "Tumor-associated" antigens are present in both tumor cells and normal cells but are present in a different quantity or a different form in tumor cells. Examples of such antigens are oncofetal antigens (e.g., carcinoembryonic antigen), differentiation antigens (e.g., T and Tn antigens), and oncogene products (e.g., HER/neu).

Cancer antigens, such as those present in cancer vaccines or those used to prepare cancer immunotherapies, can be prepared from crude cancer cell extracts, as described in Cohen P A et al. (1994) *Cancer Res* 54:1055-8, or by partially purifying the antigens, using recombinant technology, or de novo synthesis of known antigens. Cancer antigens can be used in the form of immunogenic portions of a particular antigen or in some instances a whole cell or a tumor mass can be used as the antigen. Such antigens can be isolated or prepared recombinantly or by any other means known in the art.

Other vaccines take the form of dendritic cells which have been exposed to cancer antigens in vitro, have processed the antigens and are able to express the cancer antigens at their cell surface in the context of MHC molecules for effective antigen presentation to other immune system cells. Dendritic cells form the link between the innate and the acquired immune system by presenting antigens and through their expression of pattern recognition receptors which detect microbial molecules like LPS in their local environment.

The combination motif immunostimulatory nucleic acids are useful for the treatment of allergy, including asthma. The combination motif immune stimulatory nucleic acids can be used, either alone or in combination with an allergy/asthma medicament, to treat allergy. The method entails administering to a subject having or at risk of developing an allergic or asthmatic condition an effective amount of a combination motif immune stimulatory nucleic acid of the invention to treat the allergic or asthmatic condition.

As used herein, "allergy" shall refer to acquired hypersensitivity to a substance (allergen). Allergic conditions include eczema, allergic rhinitis or coryza, hay fever, bronchial asthma, urticaria (hives) and food allergies, and other atopic conditions. A "subject having an allergy" is a subject that has or is at risk of developing an allergic reaction in response to an allergen. An "allergen" refers to a substance that can induce an allergic or asthmatic response in a susceptible subject. The list of allergens is enormous and can include pollens, insect venoms, animal dander, dust, fungal spores and drugs (e.g., penicillin).

Examples of natural animal and plant allergens include proteins specific to the following genuses: Canine (*Canis familiaris*); Dermalophagoides (e.g., *Dermalophagoides farinae*); Felis (*Felis domesticus*); Ambrosia (*Ambrosia artemiisfolia*; Lolium (e.g., *Lolium perenne* or *Lolium multiflorum*); Cryptomeria (*Cryptomeria japonica*); Alternaria (*Alternaria alternata*); Alder; Alnus (*Alnus gultinosa*); Betula (*Betula verrucosa*); Quercus (*Quercus alba*); Olea (*Olea europa*); Artemisia (*Artemisia vulgaris*); Plantago (e.g., *Plantago lanceolata*); Parielaria (e.g., *Parietaria officinalis* or *Parietaria judaica*); Blattella (e.g., *Blattella germanica*); Apis (e.g., *Apis mulliflorum*); Cupressus (e.g., *Cupressus sempervirens, Cupressus arizonica* and *Cupressus macrocarpa*); Juniperus (e.g., *Juniperus sabinoides, Juniperus virginiana, Juniperus communis* and *Juniperus ashei*); Thuya (e.g., *Thuya orientalis*); Chamaecyparis (e.g., *Chamaecyparis obtusa*); Periplaneta (e.g., *Periplaneta americana*); Agropyron (e.g., *Agropyron repens*); Secale (e.g., *Secale cereals*); Triticum (e.g., *Triticum aestivum*); Dactylis (e.g., *Dactylis glomerata*); Festuca (e.g., *Festuca elatior*); Poa (e.g., *Poa pratensis* or *Poa compressa*); Avena (e.g., *Avena sativa*); Holcus (e.g., *Holcus lanatus*); Anthoxanthum (e.g., *Anthoxanthum odoratum*); Arrhenatherum (e.g., *Arrhenatherum elatius*); Agrostis (e.g., *Agrostis alba*); Phleum (e.g., *Phleum pratense*); Phalaris (e.g., *Phalaris arundinacea*); Paspalum (e.g., *Paspalum notatum*); Sorghum (e.g., *Sorghum halepensis*); and Bromus (e.g., *Bromus inermis*).

As used herein, "asthma" shall refer to a disorder of the respiratory system characterized by inflammation, narrowing of the airways and increased reactivity of the airways to inhaled agents. Asthma is frequently, although not exclusively, associated with atopic or allergic symptoms.

An "asthma/allergy medicament" as used herein is a composition of matter which reduces the symptoms, inhibits the asthmatic or allergic reaction, or prevents the development of an allergic or asthmatic reaction. Various types of medicaments for the treatment of asthma and allergy are described in the Guidelines For The Diagnosis and Management of Asthma, Expert Panel Report 2, NIH Publication No. 97/4051, Jul. 19, 1997, the entire contents of which are incorporated herein by reference. The summary of the medicaments as described in the NIH publication is presented below.

In most embodiments the asthma/allergy medicament is useful to some degree for treating both asthma and allergy. Some asthma/allergy medicaments are preferably used in combination with the immunostimulatory nucleic acids to treat asthma. These are referred to as asthma medicaments. Asthma medicaments include, but are not limited, PDE-4 inhibitors, bronchodilator/beta-2 agonists, K+ channel openers, VLA-4 antagonists, neurokin antagonists, TXA2 synthesis inhibitors, xanthanines, arachidonic acid antagonists, 5 lipoxygenase inhibitors, thromboxin A2 receptor antagonists, thromboxane A2 antagonists, inhibitor of 5-lipoxygenase activation proteins, and protease inhibitors.

Other asthma/allergy medicaments are preferably used in combination with the immunostimulatory nucleic acids to treat allergy. These are referred to as allergy medicaments. Allergy medicaments include, but are not limited to, anti-histamines, steroids, immunomodulators, and prostaglandin inducers. Anti-histamines are compounds which counteract histamine released by mast cells or basophils. These compounds are well known in the art and commonly used for the treatment of allergy. Anti-histamines include, but are not limited to, loratidine, cetirizine, buclizine, ceterizine analogues, fexofenadine, terfenadine, desloratadine, norastemizole, epinastine, ebastine, ebastine, astemizole, levocabastine, azelastine, tranilast, terfenadine, mizolastine, betatastine, CS 560, and HSR 609. Prostaglandin inducers are compounds which induce prostaglandin activity. Prostaglandins function by regulating smooth muscle relaxation. Prostaglandin inducers include, but are not limited to, S-5751.

The steroids include, but are not limited to, beclomethasone, fluticasone, tramcinolone, budesonide, corticosteroids and budesonide. The combination of immunostimulatory nucleic acids and steroids are particularly well suited to the treatment of young subjects (e.g., children). To date, the use of steroids in children has been limited by the observation that some steroid treatments have been reportedly associated with growth retardation. Thus, according to the present invention, the immunostimulatory nucleic acids can be used in combination with growth retarding steroids, and can thereby provide a "steroid sparing effect." The combination of the two agents can result in lower required doses of steroids.

The immunomodulators include, but are not limited to, the group consisting of anti-inflammatory agents, leukotriene antagonists, IL-4 muteins, soluble IL-4 receptors, immunosuppressants (such as tolerizing peptide vaccine), anti-IL-4 antibodies, IL-4 antagonists, anti-IL-5 antibodies, soluble IL-13 receptor-Fc fusion proteins, anti-IL-9 antibodies, CCR3 antagonists, CCR5 antagonists, VLA-4 inhibitors, and, and downregulators of IgE.

The immunostimulatory nucleic acids of the invention can be used to induce type 1 IFN, i.e., IFN-α and IFN-β. The method involves contacting a cell capable of expressing a type 1 IFN with an effective amount of a combination motif immune stimulatory nucleic acid of the invention to induce type 1 IFN expression by the cell. It has recently been appreciated that the major producer cell type of IFN-α in humans is the plasmacytoid dendritic cell (pDC). This type of cell occurs at very low frequency (0.2-0.4 percent) in PBMC and is characterized by a phenotype that is lineage negative (i.e., does not stain for CD3, CD14, CD19, or CD56) and CD11c negative, while positive for CD4, CD123 (IL-3Rα), and class II major histocompatibility complex (MHC class II). Grouard G et al. (1997) *J Exp Med* 185:1101-11; Rissoan M-C et al. (1999) *Science* 283:1183-6; Siegal F P et al. (1999) *Science* 284:1835-7; Cella M et al. (1999) *Nat Med* 5:919-23. Methods of measuring type 1 IFN are well known by those skilled in the art, and they include, for example, enzyme-linked immunosorbent assay (ELISA), bioassay, and fluorescence-activated cell sorting (FACS). Assays of this sort can be performed using readily available commercial reagents and kits.

The immunostimulatory nucleic acids of the invention may be used to activate NK cells. The method involves contacting an NK cell with an effective amount of a combination motif immune stimulatory nucleic acid of the invention to activate the NK cell. The activation of the NK cells may be direct activation or indirect activation. Indirect activation refers to the induction of cytokines or other factors which cause the subsequent activation of the NK cells. NK cell activation can be assessed by various methods, including measurement of lytic activity, measurement of induction of activation markers such as CD69, and measurement of induction of certain cytokines. In addition to their characteristic ability to kill certain tumor targets spontaneously, NK cells participate in ADCC and are major producers of IFN-γ, TNF-α, GM-CSF and IL-3.

The prototypical NK-sensitive cell target for mouse NK cells is yeast artificial chromosome (YAC)-1, a thymoma derived from Moloney virus-infected A strain mice. For human NK cells, a standard target is K562, a cell line derived from an erythroleukemic lineage. In microtiter plates, a constant number of radiolabeled targets (e.g., $^{51}$Cr-labeled K562) is incubated either alone (spontaneous), with detergent (maximum), or with varying numbers of effector cells (experimental). The ratio of effector to target cells is referred to as the E:T ratio. Enriched, activated NK cells typically are effective at E:T ratios of less than 10:1, while unfractionated PBMCs or splenocytes require E:T ratios of 100:1 or more.

The immunostimulatory nucleic acids also are useful as adjuvants for inducing a systemic and/or mucosal immune response. The combination motif immune stimulatory nucleic acids of the invention can be delivered to a subject exposed to an antigen to produce an enhanced immune response to the antigen. Thus for example combination motif immune stimulatory nucleic acids are useful as vaccine adjuvants.

The immunostimulatory nucleic acids may be administered in combination with non-nucleic acid adjuvants. A non-nucleic acid adjuvant is any molecule or compound except for the immunostimulatory nucleic acids described herein which can stimulate the humoral and/or cellular immune response. Non-nucleic acid adjuvants include, for instance, adjuvants that create a depot effect, immune stimulating adjuvants, and adjuvants that create a depo effect and stimulate the immune system.

An adjuvant that creates a depot effect as used herein is an adjuvant that causes the antigen to be slowly released in the body, thus prolonging the exposure of immune cells to the antigen. This class of adjuvants includes but is not limited to alum (e.g., aluminum hydroxide, aluminum phosphate); or emulsion-based formulations including mineral oil, non-mineral oil, water-in-oil or oil-in-water-in oil emulsion, oil-in-water emulsions such as Seppic ISA series of Montanide adjuvants (e.g., Montanide ISA 720, AirLiquide, Paris, France); MF-59 (a squalene-in-water emulsion stabilized with Span 85 and Tween 80; Chiron Corporation, Emeryville, Calif.; and PROVAX (an oil-in-water emulsion containing a stabilizing detergent and a micelle-forming agent; IDEC, Pharmaceuticals Corporation, San Diego, Calif.).

An immune stimulating adjuvant is an adjuvant that causes activation of a cell of the immune system. It may, for instance, cause an immune cell to produce and secrete cytokines. This class of adjuvants includes but is not limited to saponins purified from the bark of the *Q. saponaria* tree, such as QS21 (a glycolipid that elutes in the 21$^{st}$ peak with HPLC fractionation; Aquila Biopharmaceuticals, Inc., Worcester, Mass.); poly[di(carboxylatophenoxy)phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; O M Pharma S A, Meyrin, Switzerland); and Leishmania elongation factor (a purified Leishmania protein; Corixa Corporation, Seattle, Wash.).

Adjuvants that create a depot effect and stimulate the immune system are those compounds which have both of the above-identified functions. This class of adjuvants includes but is not limited to ISCOMS (Immunostimulating complexes which contain mixed saponins, lipids and form virus-sized particles with pores that can hold antigen; CSL, Melbourne, Australia); SB-AS2 (SmithKline Beecham adjuvant system #2 which is an oil-in-water emulsion containing MPL and QS21: SmithKline Beecham Biologicals [SBB], Rixensart, Belgium); SB-AS4 (SmithKline Beecham adjuvant system #4 which contains alum and MPL; SBB, Belgium); non-ionic block copolymers that form micelles such as CRL 1005 (these contain a linear chain of hydrophobic polyoxypropylene flanked by chains of polyoxyethylene; Vaxcel, Inc., Norcross, Ga.); and Syntex Adjuvant Formulation (SAF, an oil-in-water emulsion containing Tween 80 and a nonionic block copolymer; Syntex Chemicals, Inc., Boulder, Colo.).

A non-nucleic acid mucosal adjuvant as used herein is an adjuvant other than a immunostimulatory nucleic acid that is capable of inducing a mucosal immune response in a subject when administered to a mucosal surface in conjunction with an antigen. Mucosal adjuvants include but are not limited to Bacterial toxins e.g., Cholera toxin (CT), CT derivatives including but not limited to CT B subunit (CTB) (Wu et al., 1998, Tochikubo et al., 1998); CTD53 (Val to Asp) (Fontana et al., 1995); CTK97 (Val to Lys) (Fontana et al., 1995); CTK104 (Tyr to Lys) (Fontana et al., 1995); CTD53/K63 (Val to Asp, Ser to Lys) (Fontana et al., 1995); CTH54 (Arg to His) (Fontana et al., 1995); CTN107 (His to Asn) (Fontana et al., 1995); CTE114 (Ser to Glu) (Fontana et al., 1995); CTE112K (Glu to Lys) (Yamamoto et al., 1997a); CTS61F (Ser to Phe) (Yamamoto et al., 1997a, 1997b); CTS106 (Pro to Ser) (Douce et al., 1997, Fontana et al., 1995); and CTK63 (Ser to Lys) (Douce et al., 1997, Fontana et al., 1995), Zonula occludens toxin, zot, *Escherichia coli* heat-labile enterotoxin, Labile Toxin (LT), LT derivatives including but not limited to LIT B subunit (LTB) (Verweij et al., 1998); LT7K (Arg to Lys) (Komase et al., 1998, Douce et al., 1995); LT61F (Ser to Phe) (Komase et al., 1998); LT112K (Glu to Lys) (Komase et al., 1998); LT118E (Gly to Glu) (Komase et al., 1998); LT146E (Arg to Glu) (Komase et al., 1998); LT192G (Arg to Gly) (Komase et al., 1998); LTK63 (Ser to Lys) (Marchetti et al., 1998, Douce et al., 1997, 1998, Di Tommaso et al., 1996); and LTR72 (Ala to Arg) (Giuliani et al., 1998), Pertussis toxin, PT. (Lycke et al., 1992, Spangler B D, 1992, Freytag and Clemments, 1999, Roberts et al., 1995, Wilson et al., 1995) including PT-9K/129G (Roberts et al., 1995, Cropley et al., 1995); Toxin derivatives (see below) (Holmgren et al., 1993, Verweij et al., 1998, Rappuoli et al., 1995, Freytag and Clements, 1999); Lipid A derivatives (e.g., monophosphoryl lipid A, MPL) (Sasaki et al., 1998, Vancott et al., 1998;

Muramyl Dipeptide (MDP) derivatives (Fukushima et al., 1996, Ogawa et al., 1989, Michalek et al., 1983, Morisaki et al., 1983); Bacterial outer membrane proteins (e.g., outer surface protein A (OspA) lipoprotein of *Borrelia burgdorferi*, outer membrane protein of *Neisseria meningitidis*) (Marinaro et al., 1999, Van de Verg et al., 1996); Oil-in-water emulsions (e.g., MF59) (Barchfield et al., 1999, Verschoor et al., 1999, O'Hagan, 1998); Aluminum salts (Isaka et al., 1998, 1999); and Saponins (e.g., QS21) Aquila Biopharmaceuticals, Inc., Worcester, Mass.) (Sasaki et al., 1998, MacNeal et al., 1998), ISCOMS, MF-59 (a squalene-in-water emulsion stabilized with Span 85 and Tween 80; Chiron Corporation, Emeryville, Calif.); the Seppic ISA series of Montanide adjuvants (e.g., Montanide ISA 720; AirLiquide, Paris, France); PROVAX (an oil-in-water emulsion containing a stabilizing detergent and a micelle-forming agent; IDEC Pharmaceuticals Corporation, San Diego, Calif.); Syntext Adjuvant Formulation (SAF; Syntex Chemicals, Inc., Boulder, Colo.); poly[di(carboxylatophenoxy)phosphazene (PCPP polymer; Virus Research Institute, USA) and Leishmania elongation factor (Corixa Corporation, Seattle, Wash.).

The immunostimulatory nucleic acids of the invention may be formulated as pharmaceutical compositions in a pharmaceutically acceptable carrier. The immunostimulatory nucleic acids may be directly administered to the subject or may be administered in conjunction with a nucleic acid delivery complex. A nucleic acid delivery complex shall mean a nucleic acid molecule associated with (e.g., ionically or covalently bound to; or encapsulated within) a targeting means (e.g., a molecule that results in higher affinity binding to target cell (e.g., B-cell surfaces) and/or increased cellular uptake by target cells). Examples of nucleic acid delivery complexes include nucleic acids associated with a sterol (e.g., cholesterol), a lipid (e.g., a cationic lipid, virosome or liposome), or a target cell specific binding agent (e.g., a ligand recognized by target cell specific receptor). Preferred complexes may be sufficiently stable in vivo to prevent significant uncoupling prior to internalization by the target cell. However, the complex can be cleavable under appropriate conditions within the cell so that the nucleic acid is released in a functional form.

The immunostimulatory nucleic acid and/or the antigen and/or other therapeutics may be administered alone (e.g., in saline or buffer) or using any delivery vehicles known in the art. For instance the following delivery vehicles have been described: Cochleates (Gould-Fogerite et al., 1994, 1996); Emulsomes (Vancott et al., 1998, Lowell et al., 1997); ISCOMs (Mowat et al., 1993, Carlsson et al., 1991, Hu et., 1998, Morein et al., 1999); Liposomes (Childers et al., 1999, Michalek et al., 1989, 1992, de Haan 1995a, 1995b); Microspheres (Gupta et al., 1998, Jones et al., 1996, Maloy et al., 1994, Moore et al., 1995, O'Hagan et al., 1994, Eldridge et al., 1989); Polymers (e.g., carboxymethylcellulose, chitosan) (Hamajima et al., 1998, Jabbal-Gill et al., 1998); Polymer rings (Wyatt et al., 1998); Proteosomes (Vancott et al., 1998, Lowell et al., 1988, 1996, 1997); Virosomes (Gluck et al., 1992, Mengiardi et al., 1995, Cryz et al., 1998); Virus-like particles (Jiang et al., 1999, Leibl et al., 1998). Other delivery vehicles are known in the art.

Subject doses of the compounds described herein for mucosal or local delivery typically range from about 0.1 µg to 10 mg per administration, which depending on the application could be given daily, weekly, or monthly and any other amount of time therebetween. More typically mucosal or local doses range from about 10 µg to 5 mg per administration, and most typically from about 100 µg to 1 mg, with 2-4 administrations being spaced days or weeks apart. More typically, immune stimulant doses range from 1 µg to 10 mg per administration, and most typically 10 µg to 1 mg, with daily or weekly administrations. Subject doses of the compounds described herein for parenteral delivery for the purpose of inducing an antigen-specific immune response, wherein the compounds are delivered with an antigen but not another therapeutic agent are typically 5 to 10,000 times higher than the effective mucosal dose for vaccine adjuvant or immune stimulant applications, and more typically 10 to 1,000 times higher, and most typically 20 to 100 times higher. Doses of the compounds described herein for parenteral delivery for the purpose of inducing an innate immune response or for increasing ADCC or for inducing an antigen specific immune response when the immunostimulatory nucleic acids are administered in combination with other therapeutic agents or in specialized delivery vehicles typically range from about 0.1 µg to 10 mg per administration, which depending on the application could be given daily, weekly, or monthly and any other amount of time therebetween. More typically parenteral doses for these purposes range from about 10 µg to 5 mg per administration, and most typically from about 100 µg to 1 mg, with 2-4 administrations being spaced days or weeks apart. In some embodiments, however, parenteral doses for these purposes may be used in a range of 5 to 10,000 times higher than the typical doses described above.

As used herein, "effective amount" shall refer to the amount necessary or sufficient to realize a desired biological effect. For example, an effective amount of an immunostimulatory nucleic acid for treating an infection is that amount necessary to treat the infection. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular immunostimulatory nucleic acid being administered, the antigen, the size of the subject, or the severity of the disease or condition. One of ordinary skill in the art can empirically determine the effective amount of a particular immunostimulatory nucleic acid and/or antigen and/or other therapeutic agent without necessitating undue experimentation.

For any compound described herein the therapeutically effective amount can be initially determined from animal models. A therapeutically effective dose can also be determined from human data for CpG oligonucleotides which have been tested in humans (human clinical trials have been initiated) and for compounds which are known to exhibit similar pharmacological activities, such as other mucosal adjuvants, e.g., LT and other antigens for vaccination purposes, for the mucosal or local administration. Higher doses are required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the immunostimulatory nucleic acid can be administered to a subject by any mode that delivers the nucleic acid to the desired surface, e.g., mucosal, systemic. Administering the pharmaceutical composition of the present invention may be accomplished by any means known to the skilled artisan. Preferred routes of administration include but are not limited to oral, parenteral, intramuscular, intranasal, intratracheal, inhalation, ocular, sublingual, vaginal, and rectal.

For oral administration, the compounds (i.e., immunostimulatory nucleic acids, antigens and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer (1990) *Science* 249:1527-33, which is incorporated herein by reference.

The immunostimulatory nucleic acids and optionally other therapeutics and/or antigens may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulfuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of an immunostimulatory nucleic acid and optionally antigens and/or other therapeutic agents optionally included in a pharmaceutically acceptable carrier. The term "pharmaceutically acceptable carrier" means one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction For treatment of a subject, depending on activity of the compound, manner of administration, purpose of the immunization (i.e., prophylactic or therapeutic), nature and severity of the disorder, age and body weight of the patient, different doses may be necessary. The administration of a given dose can be carried out both by single administration in the form of an individual dose unit or else several smaller dose units. Multiple administration of doses at specific intervals of weeks or months apart is usual for boosting the antigen-specific responses.

Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-, di-, and tri-glycerides; hydrogel release systems; silastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1

ODN 2395 is a Remarkably Strong Activator of NK Cells and IFN-α Production

We previously recognized and described oligodeoxynucleotides (ODN) containing neutralizing motifs consisting of repeats of the sequence CG such as CGCGCG or where the CG is preceded by a C and/or followed by a G. These neutralizing motifs were believed to reduce the stimulatory effects of ODN on multiple readouts, such as secretion of IL-6, IL-12, IFN-γ, TNF-α, and induction of an antigen-specific immune response. Krieg A M et al. (1998) *Proc Natl Acad Sci USA* 95:12631-6.

In many cases, the presence of a neutralizing motif in an oligonucleotide together with a stimulatory motif was believed to prevent immune activation. One such ODN containing both stimulatory and neutralizing motifs is ODN 2136, which has the sequence TCCTGACGTTCG-GCGCGCGCCC (SEQ ID NO: 19). The 3' end of this ODN contains a fairly typical neutralizing motif, CGGCGCGCGCCC (SEQ ID NO: 37), derived from the 3' end of the inhibitory ODN 2010 (GCGGCGGGCG-GCGCGCGCCC, SEQ ID NO: 38). Surprisingly, ODN 2136 had strong activity for inducing NK cell lytic activity (lytic units, L.U.). As shown in Table 1, ODN 2136 at a concentration of 3 µg/ml was actually stronger than our standard B-cell and NK cell stimulatory phosphorothioate ODN 2006 (TCGTCGTTTTGTCGTTTTGTCGTT, SEQ ID NO: 39) for induction of L.U. More strikingly, whereas ODN 2006 only induced the production of 2,396 pg/ml of IFN-α, ODN 2136 induced the production of 14,278 pg/ml (FIG. 1). This indicated that, surprisingly, the presence of this neutralizing sequence was not necessarily to be avoided.

TABLE 1

Human PBL Cultured Overnight With Various ODN.

| ODN | E:T RATIO | | | | | | L.U. |
|---|---|---|---|---|---|---|---|
| | 3.1 | 6.3 | 12.5 | 25.0 | 50.0 | 100.0 | |
| ALONE | 0.86 | 1.47 | 4.15 | 7.25 | 11.66 | 18.57 | 0.13 |
| IL-2 (100 U/ml) | 12.21 | 29.21 | 46.63 | 67.88 | 78.28 | 76.65 | 33.26 |
| 1585 (3 µg/ml) | 6.47 | 12.61 | 24.65 | 36.82 | 49.30 | 53.00 | 11.69 |
| 1585 (10 µg/ml) | 8.52 | 18.17 | 33.20 | 51.26 | 72.13 | 73.89 | 20.94 |
| 1585 (30 µg/ml) | 5.75 | 13.05 | 20.00 | 34.34 | 45.02 | 56.49 | 10.66 |
| 2118 (10 µg/ml) | 0.62 | 2.08 | 3.90 | 8.53 | 12.79 | 15.93 | 0.09 |
| 2006 (0.6 µg/ml) | 1.62 | 2.88 | 8.24 | 14.10 | 21.85 | 31.91 | 1.73 |
| 2006 (3 µg/ml) | 7.07 | 17.02 | 30.28 | 50.66 | 69.13 | 74.27 | 19.41 |
| 2169 (0.6 µg/ml) | 3.65 | 3.81 | 6.67 | 13.45 | 24.48 | 32.42 | 1.84 |
| 2169 (3 µg/ml) | 11.20 | 21.47 | 38.15 | 59.66 | 78.96 | 77.72 | 25.76 |
| 1760 (0.6 µg/ml) | 0.35 | 2.70 | 6.85 | 8.59 | 16.09 | 20.63 | 0.33 |
| 1760 (3 µg/ml) | 7.57 | 12.94 | 27.50 | 46.63 | 62.43 | 66.97 | 16.60 |
| 1758 (0.6 µg/ml) | 2.07 | 6.05 | 12.80 | 23.25 | 34.57 | 44.93 | 5.43 |
| 1758 (3 µg/ml) | 8.40 | 17.84 | 33.41 | 52.20 | 69.52 | 74.46 | 20.78 |
| 2398 (0.6 µg/ml) | 1.83 | 1.92 | 6.21 | 11.21 | 20.38 | 26.71 | 0.98 |
| 2398 (3 µg/ml) | 4.36 | 12.90 | 24.10 | 42.37 | 60.51 | 70.03 | 15.02 |
| 2397 (0.6 µg/ml) | 2.14 | 3.15 | 8.79 | 17.37 | 28.71 | 42.45 | 3.80 |
| 2397 (3 µg/ml) | 10.09 | 22.52 | 38.96 | 61.85 | 77.69 | 74.87 | 26.12 |
| 2396 (0.6 µg/ml) | 2.93 | 5.80 | 13.22 | 25.32 | 36.83 | 46.77 | 6.13 |
| 2396 (3 µg/ml) | 9.03 | 18.65 | 32.71 | 54.62 | 72.62 | 73.67 | 21.64 |
| 2395 (0.6 µg/ml) | 5.10 | 9.22 | 17.21 | 31.67 | 49.53 | 60.53 | 10.59 |
| 2395 (3 µg/ml) | 10.91 | 24.55 | 40.42 | 61.23 | 71.11 | 75.52 | 26.94 |
| 2136 (0.6 µg/ml) | 0.39 | 2.89 | 7.12 | 12.70 | 18.88 | 24.11 | 0.78 |
| 2136 (3 µg/ml) | 11.94 | 23.57 | 39.11 | 55.16 | 70.84 | 71.99 | 25.62 |

ODN sequences for Table 1
1585 GGGGTCAACGTTGAGGGGGG (SEQ ID NO: 35)
1758 TCTCCCAGCGTGCGCCAT (SEQ ID NO: 40)
1760 ATAATCGACGTTCAAGCAAG (SEQ ID NO: 41)
2006 TCGTCGTTTTGTCGTTTTGTCGTT (SEQ ID NO: 39)
2118 GGGGTCAAGCTTGAGGGGGG (SEQ ID NO: 36)
2136 TCCTGACGTTCGGCGCGCGCCC (SEQ ID NO: 19)
2169 TCTATCGACGTTCAAGCAAG (SEQ ID NO: 42)
2395 TCGTCGTTTTCGGCGCGCGCCG (SEQ ID NO: 1)
2396 TCGTCGTTTTTGTCGTTTTTGTCGTT (SEQ ID NO: 43)
2397 TCGTCGTTTTGTCGTTTTTGTCGTTT (SEQ ID NO: 44)
2398 TTCGTGTTTTCGTGTTTTCGTCGT (SEQ ID NO: 45)

However, in an effort to understand this observation, an even stronger NK activator and IFN-α inducer was created by combining the 3' end of ODN 2136 with the 5' end of ODN 2006. The resulting ODN 2395 (TCGTCGTTTTCG-GCGCGCGCCG, SEQ ID NO: 1) serendipitously incorporated a change of the last base on the 3' end from a C to a G. This single base change has the effect of creating a perfect 12-base-long palindrome at the 3' end of ODN 2395 where in ODN 2136 the palindrome is only 10 bases long.

Figure 2:
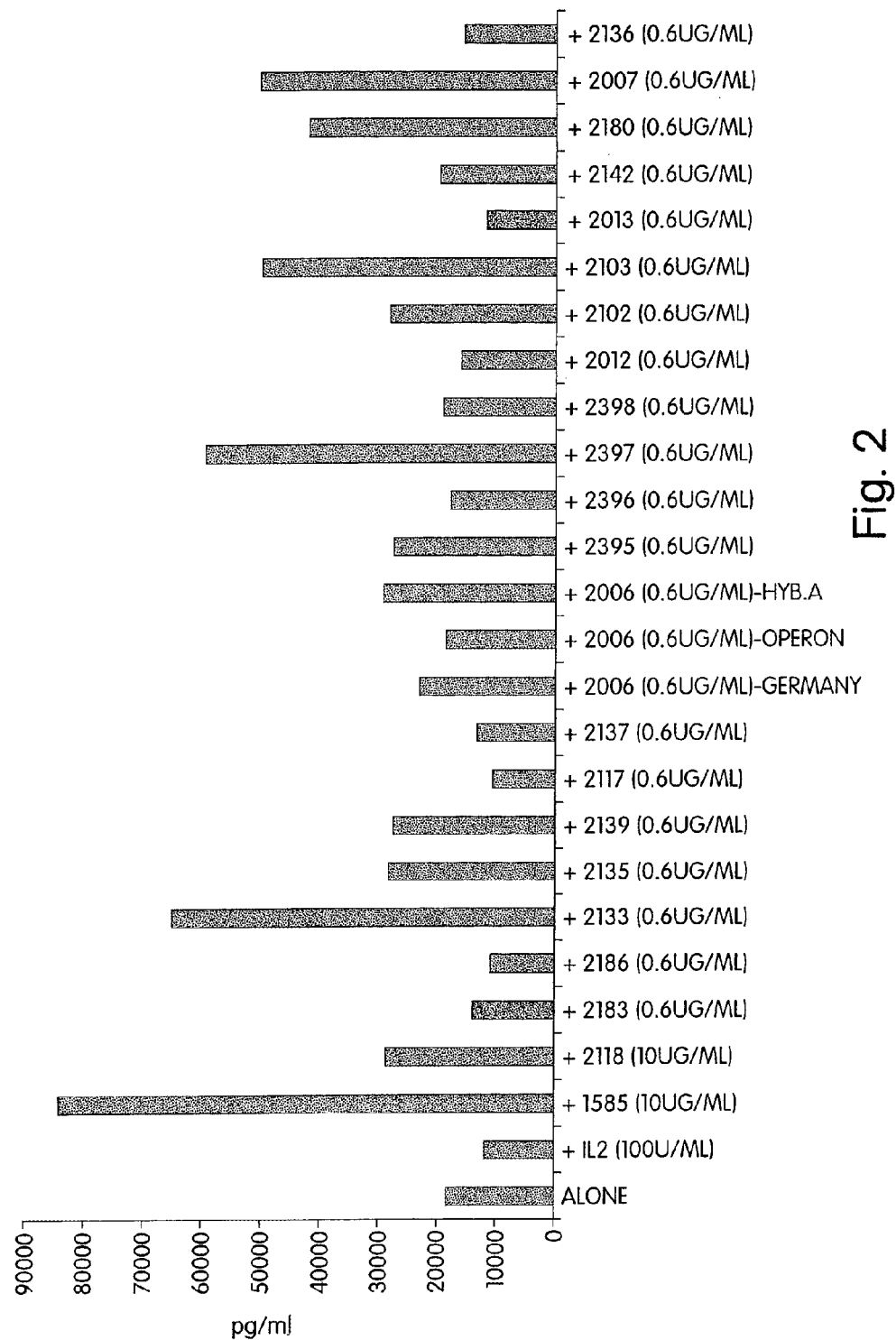
FIG. 2 is a bar graph depicting amounts of MCP-1 (pg/ml) induced in human PBMCs after 24 hours of culture alone, with IL-2, or in the presence of the indicated ODN at the indicated concentrations.
Figure 3:
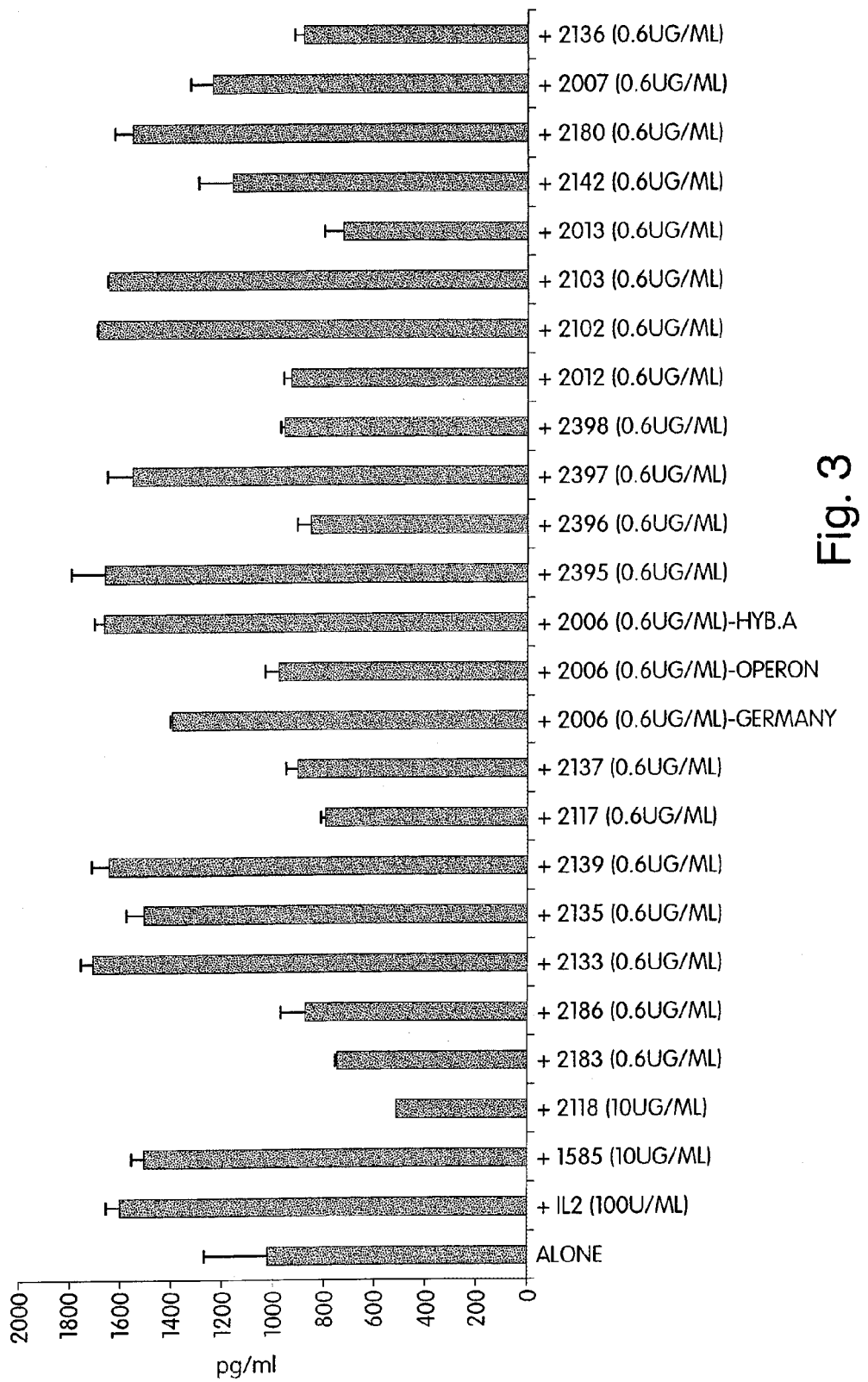
FIG. 3 is a bar graph depicting amounts of IP-10 (pg/ml) induced in human PBMCs after 24 hours of culture alone, with IL-2, or in the presence of the indicated ODN at the indicated concentrations.

Table 2 shows another example of data where ODN 2395 is remarkably potent at inducing NK cell L.U. compared to most other all-phosphorothioate backbone ODN. In this assay ODN 2395 is weaker than the positive control ODN 1585, which has a chimeric phosphorothioate/phosphodiester (SOS) backbone. ODN 1585 (ggGGTCAACGT-TGAggggG, SEQ ID NO: 35), is described in published PCT Application WO 01/22990. At the low concentration of 0.6 µg/ml tested in this experiment, ODN 2136 induced no L.U. above the background of 0.03 in the no-ODN control. FIG. 2 and FIG. 3 show the level of monocyte chemotactic protein (MCP)-1 and IFN-inducible protein (IP)-10, respectively, in the supernatants from the NK cell cultures in Table 2. MCP-1 is a chemokine that is a ligand for CCR2 and is associated with both Th1 and Th2-type immune responses. IP-10 is a CXC chemokine that is a ligand for CXCR3 and is associated with Th1 responses. Loetscher P et al. (2001) *J Biol Chem* 276:2986-91. These data show that ODN 2395 is a relatively strong inducer of IP-10 production, but induces only average levels of MCP-1.

TABLE 2

Human PBL Cultured Overnight With Various ODN.

| ODN | E:T RATIO | | | | | | L.U. |
|---|---|---|---|---|---|---|---|
| | 3.1 | 6.3 | 12.5 | 25.0 | 50.0 | 100.0 | |
| ALONE | 1.73 | 3.10 | 4.25 | 7.72 | 12.07 | 14.56 | 0.03 |
| IL-2 (100 U/ml) | 16.68 | 29.41 | 49.42 | 74.78 | 87.64 | 92.63 | 37.17 |
| 1585 (10 µg/ml) | 9.60 | 17.25 | 35.63 | 55.76 | 77.53 | 87.14 | 22.94 |
| 2118 (10 µg/ml) | 2.99 | 2.88 | 3.41 | 6.72 | 9.26 | 14.18 | 0.01 |
| 2183 (0.6 µg/ml) | 2.13 | 2.28 | 3.29 | 8.17 | 10.47 | 17.87 | 0.07 |
| 2186 (0.6 µg/ml) | 1.23 | 2.18 | 3.50 | 6.26 | 9.58 | 14.51 | 0.02 |
| 2133 (0.6 µg/ml) | 2.13 | 3.45 | 9.69 | 18.85 | 32.72 | 44.67 | 4.63 |
| 2135 (0.6 µg/ml) | 2.07 | 4.06 | 7.70 | 12.63 | 21.90 | 34.58 | 1.92 |
| 2139 (0.6 µg/ml) | 2.94 | 5.15 | 9.63 | 15.15 | 24.90 | 38.71 | 2.83 |
| 2117 (0.6 µg/ml) | 1.21 | 2.32 | 4.08 | 7.61 | 10.09 | 16.27 | 0.05 |
| 2137 (0.6 µg/ml) | 1.66 | 2.79 | 4.43 | 7.92 | 10.64 | 16.91 | 0.06 |
| 2006 (0.6 µg/ml) | 1.92 | 3.38 | 5.06 | 11.57 | 16.82 | 25.30 | 0.65 |
| 2006 (0.6 µg/ml) | 0.91 | 2.19 | 4.52 | 7.39 | 13.86 | 21.57 | 0.28 |
| 2006 (0.6 µg/ml) | 1.92 | 3.59 | 7.67 | 12.51 | 18.99 | 28.03 | 1.04 |
| 2395 (0.6 µg/ml) | 2.88 | 7.20 | 10.80 | 23.96 | 37.97 | 54.38 | 7.02 |
| 2396 (0.6 µg/ml) | 0.92 | 2.18 | 4.07 | 5.78 | 10.18 | 14.95 | 0.03 |
| 2397 (0.6 µg/ml) | 3.05 | 5.24 | 10.51 | 17.50 | 33.51 | 46.50 | 4.92 |
| 2398 (0.6 µg/ml) | 1.37 | 2.82 | 5.16 | 8.48 | 15.72 | 21.72 | 0.34 |
| 2012 (0.6 µg/ml) | 0.88 | 1.71 | 4.41 | 7.07 | 10.97 | 16.47 | 0.06 |
| 2102 (0.6 µg/ml) | 2.36 | 5.82 | 10.59 | 17.88 | 30.96 | 39.79 | 3.81 |
| 2103 (0.6 µg/ml) | 2.12 | 4.32 | 8.83 | 13.49 | 25.23 | 35.47 | 2.37 |
| 2013 (0.6 µg/ml) | 1.11 | 2.42 | 4.42 | 6.01 | 9.15 | 13.44 | 0.01 |
| 2142 (0.6 µg/ml) | 0.94 | 1.55 | 4.38 | 7.44 | 11.45 | 16.84 | 0.08 |
| 2180 (0.6 µg/ml) | 2.06 | 4.08 | 6.91 | 11.54 | 16.82 | 25.76 | 0.67 |
| 2007 (0.6 µg/ml) | 1.83 | 3.30 | 6.68 | 12.34 | 20.74 | 29.10 | 1.25 |
| 2136 (0.6 µg/ml) | | | | | | | 0.01 |

ODN sequences for Table 2
1585 GGGGTCAACGTTGAGGGGGG (SEQ ID NO: 35)
2006 TCGTCGTTTTGTCGTTTTGTCGTT (SEQ ID NO: 39)
2007 TCGTCGTTGTCGTTTTGTCGTT (SEQ ID NO: 46)
2013 TGTCGTTGTCGTTGTCGTTGTCGTT (SEQ ID NO: 48)
2102 TCGTCGTTTTGACGTTTTGTCGTT (SEQ ID NO: 49)
2103 TCGTCGTTTTGACGTTTTGACGTT (SEQ ID NO: 50)
2117 TZGTZGTTTTGTZGTTTTGTZGTT (SEQ ID NO: 51)
2118 GGGGTCAAGCTTGAGGGGGG (SEQ ID NO: 36)
2133 TCGTCGTTGGTTGTCGTTTTGGTT (SEQ ID NO: 17)
2135 ACCATGGACGAGCTGTTTCCCCTC (SEQ ID NO: 18)
2136 TCCTGACGTTCGGCGCGCGCCC (SEQ ID NO: 19)
2137 TGCTGCTTTTGTGCTTTTGTGCTT (SEQ ID NO: 20)
2139 TCGTCGTTTCGTCGTTTTGACGTT (SEQ ID NO: 21)
2142 TCGCGTGCGTTTTGTCGTTTTGACGTT (SEQ ID NO: 22)
2180 TCGTCGTTTTTGTCGTTTTTGTCGTT (SEQ ID NO: 52)
2183 TTTTTTTTTTTTTTTTTTTTTTTT (SEQ ID NO: 53)
2186 TCGTCGCTGTCTCCGCTTCTTCTTGCC (SEQ ID NO: 54)
2395 TCGTCGTTTTCGGCGCGCGCCG (SEQ ID NO: 1)
2396 TCGTCGTTTTTGTCGTTTTTGTCGTT (SEQ ID NO: 43)
2397 TCGTCGTTTTGTCGTTTTTGTCGTTT (SEQ ID NO: 44)
2398 TTCGTGTTTTCGTGTTTTCGTCGT (SEQ ID NO: 45)

Based on these and other data, we concluded that the ODN 2395 sequence was a remarkably strong activator of NK cells and IFN-α production.

Example 2

ODN Related to ODN 2395 are Also Strong Activators of NK Cells and IFN-α Production Additional ODN 2427-2433 (SEQ ID NOs: 2-8) were designed and synthesized to test the possibility that the palindrome at the 3' end of ODN 2395 may be important in its immune stimulatory activity. Table 3 compares the ability of these different ODN to activate NK L.U. As is evident from these data, the strongest ODN at the concentration of 1 µg/ml is ODN 2429 (TCGTCGTTTTCGGCGGCCGCCG, SEQ ID NO: 4) which induced 2.85 L.U. of NK activity. ODN 2006 was very weak in the experiment, and all of the other oligos that were tested except for the control ODN 2118 (GGGGT-CAAGCTTGAGGGGGG, SEQ ID NO: 36) that has no CG were stronger than 2006. ODN 2429 is notable because it is the only one that maintains a 12-base palindrome, although this is a different palindrome from the one that was present in 2395. ODN 2430 (TCGTCGTTTTCGGCGCGCCGCG, SEQ ID NO: 5), which is the second strongest ODN at the 1 µg/ml concentration, is similar; but the palindrome has been slightly shortened to 10 bases long. The remainder of the ODN have either no or shorter palindromic sequences, and induce less NK activity.

TABLE 3

Human PBL Cultured Overnight With Various ODN.

| ODN | E:T RATIO | | | | | | L.U. |
|---|---|---|---|---|---|---|---|
| | 3.1 | 6.3 | 12.5 | 25.0 | 50.0 | 100.0 | |
| ALONE | 0.37 | 0.64 | 0.25 | 1.02 | 2.15 | 3.23 | 0.00 |
| IL-2 (100 U/ml) | 3.01 | 4.20 | 9.01 | 18.92 | 27.37 | 38.17 | 3.22 |
| 1585 (10 µg/ml) | 1.35 | 2.30 | 4.38 | 8.07 | 13.96 | 22.31 | 0.31 |
| 2118 (10 µg/ml) | −0.31 | −0.21 | 0.22 | 1.57 | 1.24 | 2.41 | 0.00 |
| 2395 (1 µg/ml) | 1.01 | 2.61 | 5.73 | 11.39 | 18.92 | 28.16 | 1.04 |
| 2395 (3 µg/ml) | 1.59 | 2.55 | 5.96 | 12.09 | 20.46 | 33.87 | 1.71 |
| 2006 (1 µg/ml) | −0.08 | 0.73 | 1.45 | 3.03 | 7.11 | 12.49 | 0.01 |
| 2006 (3 µg/ml) | 0.16 | 0.76 | 2.98 | 4.98 | 9.79 | 20.58 | 0.15 |
| 2427 (1 µg/ml) | 0.85 | 1.80 | 4.03 | 6.37 | 12.53 | 24.12 | 0.34 |
| 2427 (3 µg/ml) | 0.96 | 2.24 | 4.40 | 8.00 | 15.01 | 21.85 | 0.33 |
| 2428 (1 µg/ml) | 1.19 | 1.97 | 3.64 | 7.72 | 16.27 | 24.74 | 0.53 |
| 2428 (3 µg/ml) | 1.42 | 2.36 | 5.67 | 11.06 | 19.11 | 28.17 | 1.03 |
| 2429 (1 µg/ml) | 1.47 | 3.84 | 7.83 | 14.17 | 25.47 | 38.99 | 2.85 |
| 2429 (3 µg/ml) | 0.57 | 2.38 | 4.21 | 8.98 | 16.88 | 26.36 | 0.72 |
| 2430 (1 µg/ml) | 1.49 | 3.55 | 6.25 | 12.76 | 20.51 | 31.67 | 1.51 |
| 2430 (3 µg/mi) | 1.23 | 1.52 | 3.89 | 8.78 | 15.28 | 25.56 | 0.57 |
| 2431 (1 µg/ml) | 0.96 | 2.90 | 3.58 | 8.29 | 15.23 | 25.29 | 0.53 |
| 2431 (3 µg/ml) | 1.82 | 3.25 | 5.53 | 9.67 | 21.04 | 32.78 | 1.51 |
| 2432 (1 µg/ml) | 1.67 | 2.97 | 4.87 | 8.54 | 19.26 | 27.10 | 0.84 |
| 2432 (3 µg/ml) | 1.03 | 2.39 | 5.22 | 9.41 | 18.48 | 25.74 | 0.76 |
| 2433 (1 µg/ml) | 0.74 | 1.84 | 2.30 | 6.97 | 12.43 | 18.94 | 0.15 |
| 2433 (3 µg/ml) | 1.25 | 3.13 | 4.47 | 9.85 | 14.77 | 22.75 | 0.38 |

ODN sequences for Table 3
1585 GGGGTCAACGTTGAGGGGGG (SEQ ID NO: 35)
2006 TCGTCGTTTTGTCGTTTTGTCGTT (SEQ ID NO: 39)
2118 GGGGTCAAGCTTGAGGGGGG (SEQ ID NO: 36)
2395 TCGTCGTTTTCGGCGCGCGCCG (SEQ ID NO: 1)
2427 TCGTCGTTTTCGTCGCGCGCCG (SEQ ID NO: 2)
2428 TCGTCGTTTTCGTCGCGCGGCG (SEQ ID NO: 3)
2429 TCGTCGTTTTCGGCGGCCGCCG (SEQ ID NO: 4)
2430 TCGTCGTTTTCGGCGCGCCGCG (SEQ ID NO: 5)
2431 TCGTCGTTTTCGGCGCCGGCCG (SEQ ID NO: 6)
2432 TCGTCGTTTTCGGCCCGCGCGG (SEQ ID NO: 7)
2433 TCGTCGTTTTCCGCCGCCGGGG (SEQ ID NO: 8)

Figure 4:
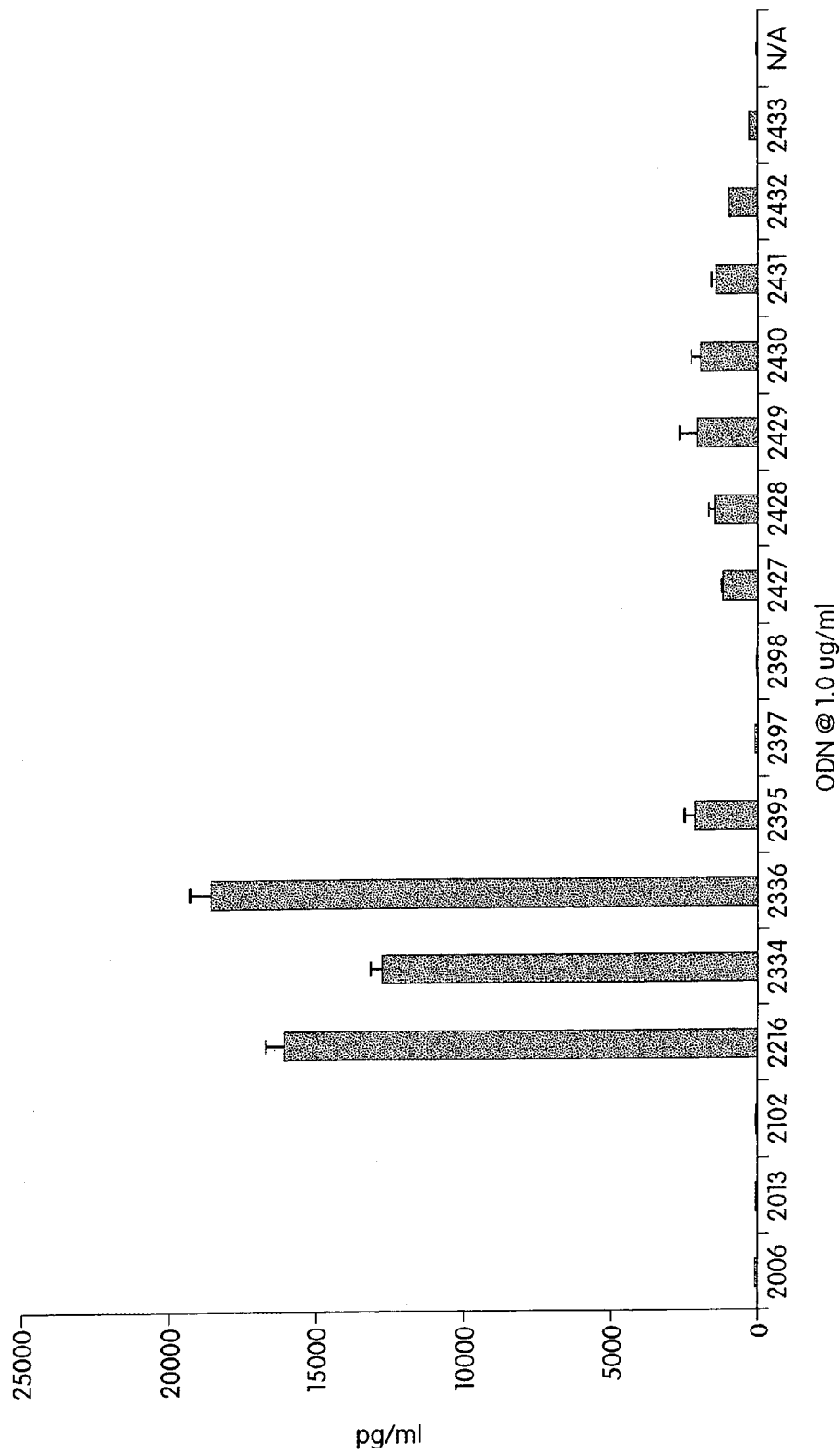
FIG. 4 is a bar graph depicting amounts of IFN-α (pg/ml) induced in human PBMCs after 48 hours of culture alone (N/A) or in the presence of the indicated ODN at 1.0 μg/ml.

FIG. 4 shows the ability of these oligos to induce IFN-α production compared to the positive control SOS ODN 2216 (GGGGGACGATCGTCGGGGG, SEQ ID NO: 55), 2334 (GGGGTCGACGTCGACGTCGAGGGGGGG, SEQ ID NO: 56), and 2336 (GGGGACGACGTCGTGGGGGGG, SEQ ID NO: 57). All of the 2395-related ODN induce a higher level of IFN-α production than ODN 2006, although the levels are below the levels induced by the chimeric SOS ODN. The rank order of induction of IFN-α expression is roughly similar to that of NK L.U., with the strongest effects seen by ODN 2395 and 2429.

Figure 5A:
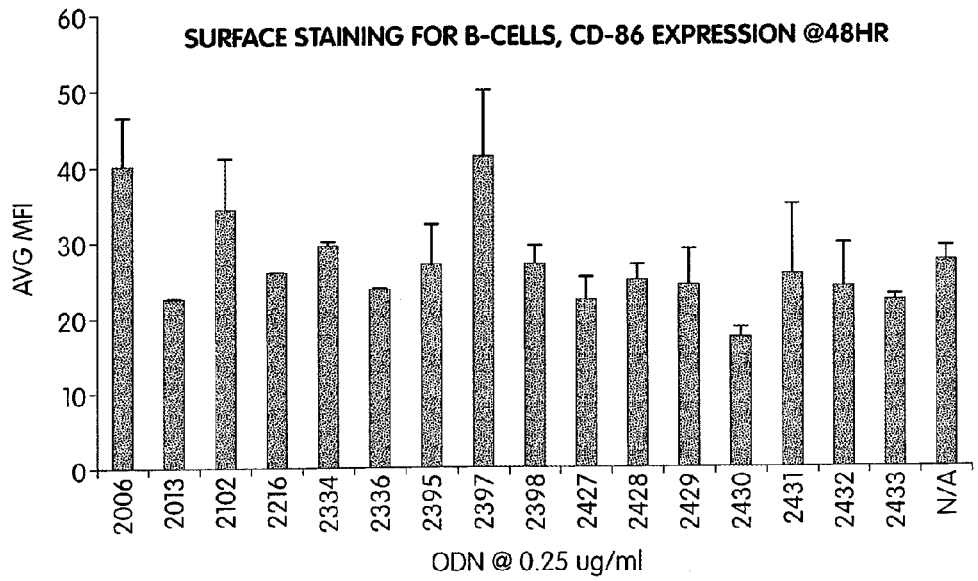
FIG. 5 is a pair of bar graphs depicting surface staining on B cells for CD86 (MFI) after 48 hours of culture alone (N/A) or in the presence of the indicated ODN at 0.25 μg/ml (panel A) or 1.0 μg/ml (panel B).
Figure 5B:
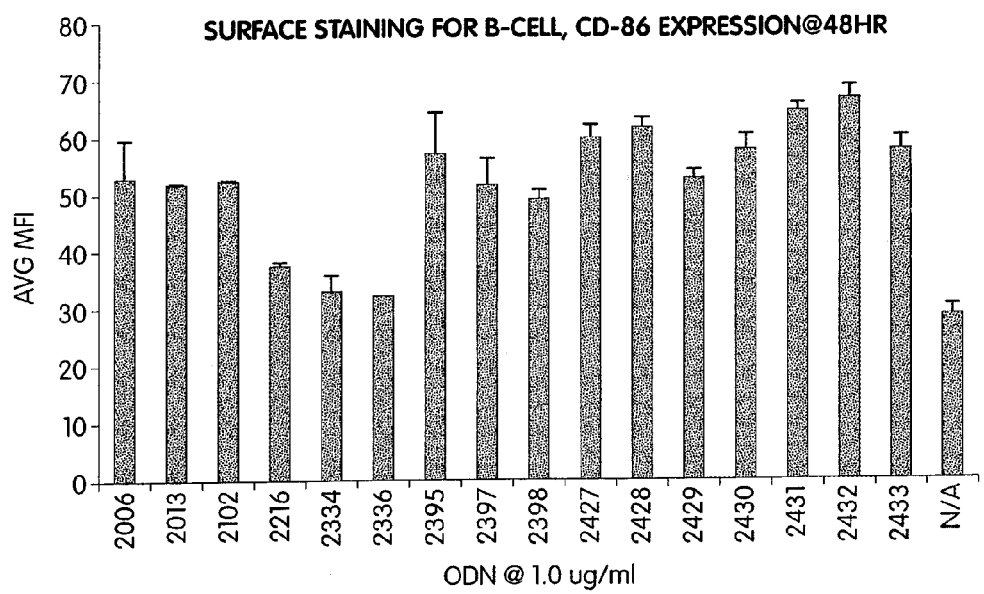
Figure 6A:
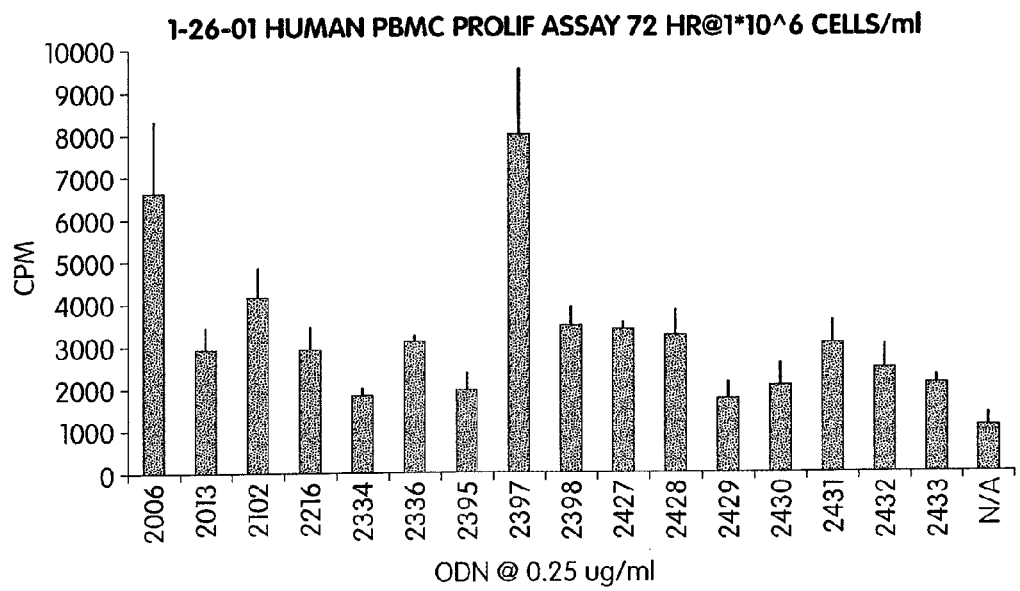
FIG. 6 is a pair of bar graphs depicting results of a 72 hour B cell proliferation assay (cpm $^3$H-thymidine incorporation) alone (N/A) or in the presence of the indicated ODN at 0.25 μg/ml (panel A) or 1.0 μg/ml (panel B).
Figure 6B:
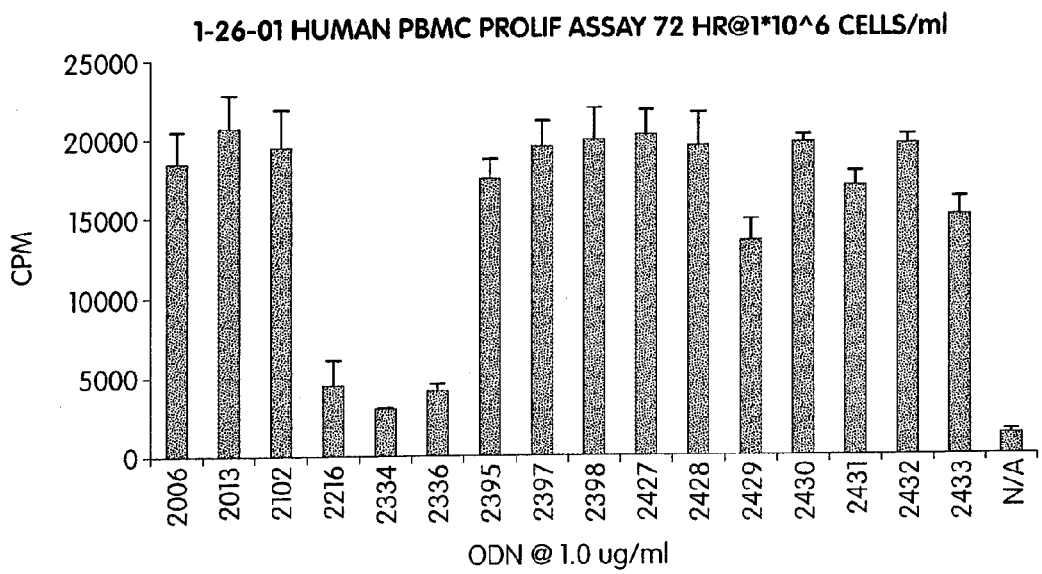

Example 3 the Strong Stimulatory Effects on NK Cells and IFN-α Production do not Correspond to B-Cell Effects As shown in FIG. 5A, ODN 2395 and its relatives were significantly weaker at a 0.25 µg/ml concentration than ODN 2006 or its relative 2397, in terms of their ability to induce B-cell expression of CD86 at 48 hours. As we have noticed previously, at higher ODN concentrations such as 1 µg/ml, less difference was seen between the various ODN (FIG. 5B). In the same experiment, we also measured B-cell activation by a proliferation assay ($^3$H-thymidine incorporation; FIG. 6). Again, at the 0.25 µg/ml concentration ODN 2006 and ODN 2397 (SEQ ID NO: 44) were by far the strongest (FIG. 6A). However, at higher concentrations, the 2395-related ODN were similar in their efficacy (FIG. 6B).

Example 4

ODN 2395 and Related ODN are Weak Inducers of IL-10

Figure 7A:
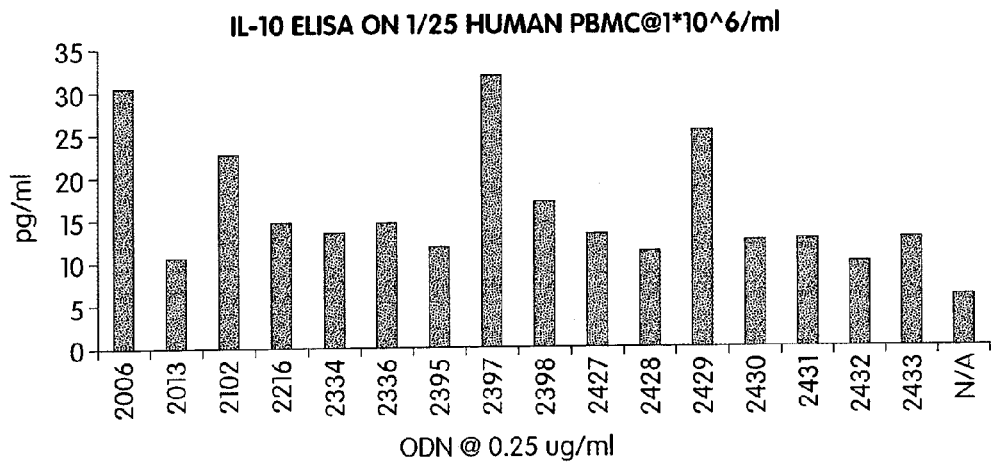
FIG. 7 is a pair of bar graphs depicting amounts of IL-10 (pg/ml) induced in human PBMCs after 24 hours of culture either alone (N/A) or in the presence of the indicated ODN at 0.25 μg/ml (panel A) or 1.0 μg/ml (panel B).
Figure 7B:
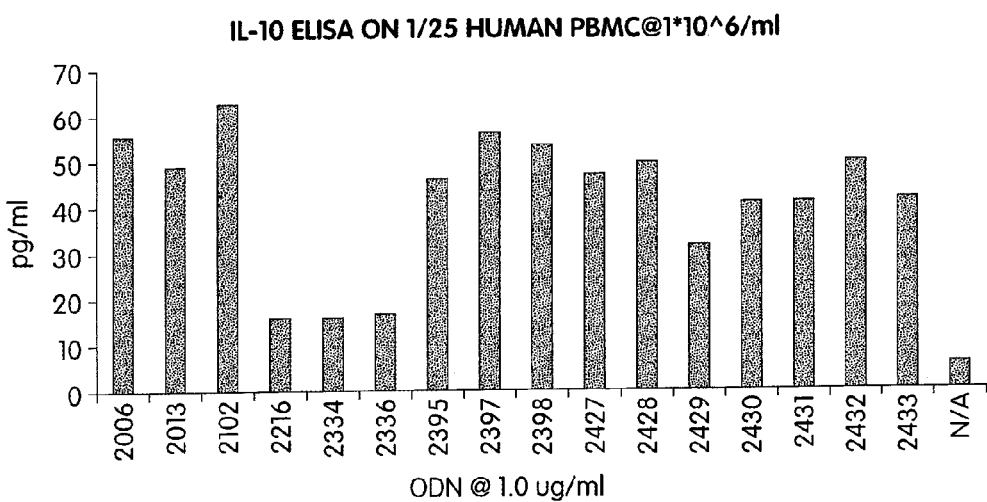

Our previous studies have suggested that most of the IL-10 production that is induced by CpG is derived from B cells. As shown in FIG. 7, IL-10 expression correlated well with B-cell proliferation. Again, ODN 2006 and its relative ODN 2397 were the strongest at the low concentration of 0.25 µg/ml. ODN 2395 and its relatives induced less IL-10 production at this concentration.

Example 5

Concentration Dependence of Immune Stimulatory Effect

Figure 8:
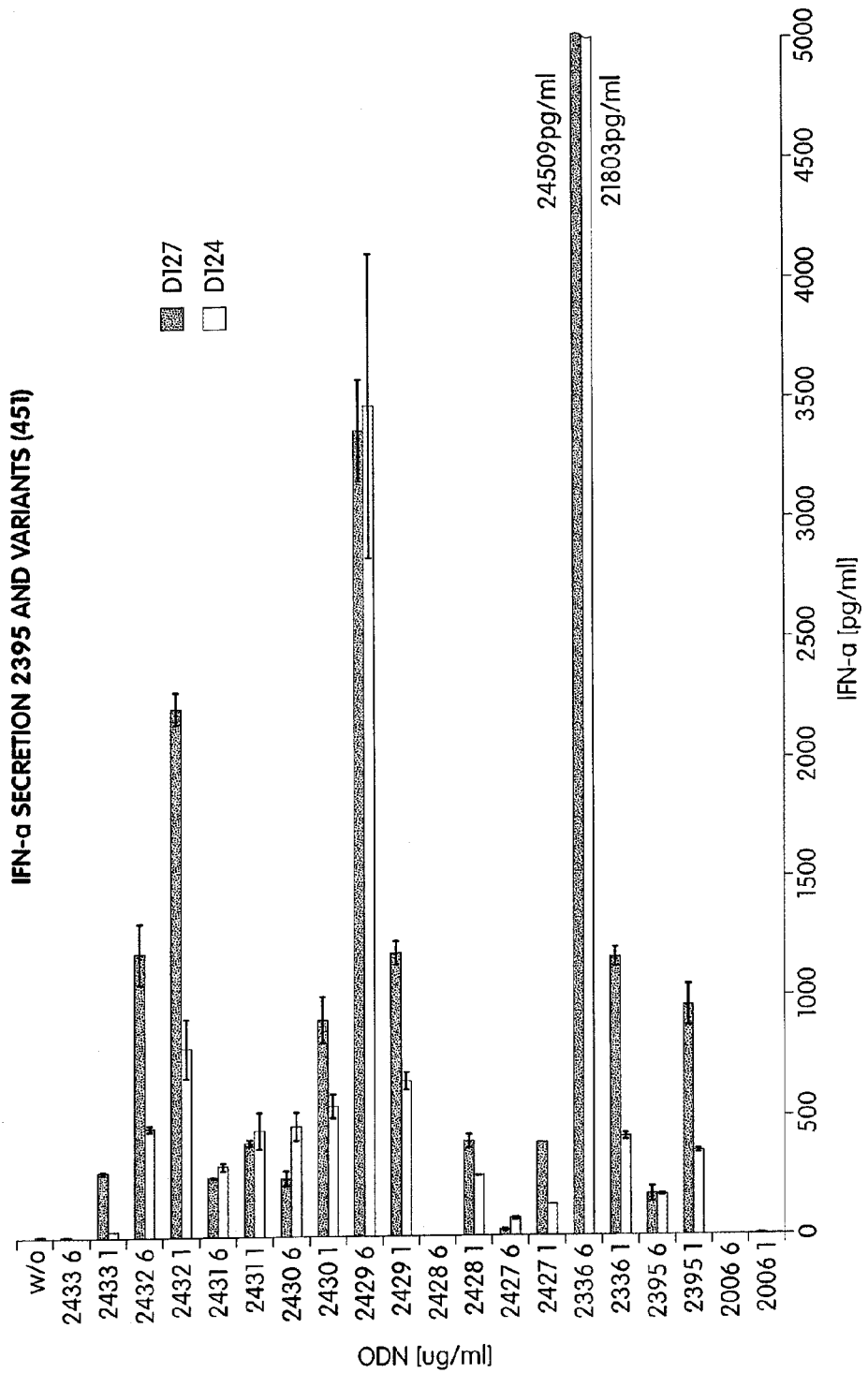
FIG. 8 is a bar graph depicting amounts of IFN-α (pg/ml) induced in PBMC from two donors (D127, solid bars, and D124, open bars) following 24 hours of culture alone (w/o) or in the presence of the indicated ODN at the indicated concentrations (1 or 6 μg/ml).

Additional studies on this class of oligonucleotides and the derivatives involved ODN numbers 2427-2433 (SEQ ID NOs: 2-8). Data for these ODN are shown in FIG. 8. This demonstrates again that ODN 2006 was very weak at inducing IFN-α production at a concentration of either 1 or 6 µg/ml. However, ODN 2395 induced substantial amounts of IFN-α, especially at the lower concentration of 1 µg/ml. We have occasionally seen ODN where the stimulatory activity was reduced at higher concentrations, such as 6 µg/ml, in comparison to the effects seen at lower concentrations such as 1 µg/ml. In the experiments shown in FIG. 8, ODN 2395 was more potent at the lower concentration than at the higher concentration, but ODN 2429 was more potent at the higher concentration. In contrast to the common inverted dose-response curve of phosphorothioate ODN, chimeric ODN such as ODN 2336 in this experiment typically showed increased immune stimulatory effects at higher concentrations. The stimulatory effect of ODN 2432 in this experiment shown in FIG. 8 was interesting considering that this ODN has no good palindrome. This system with the relatively weak B cell stimulatory activity is shown in FIG. 5 and FIG. 6.

Example 6

Figure 9:
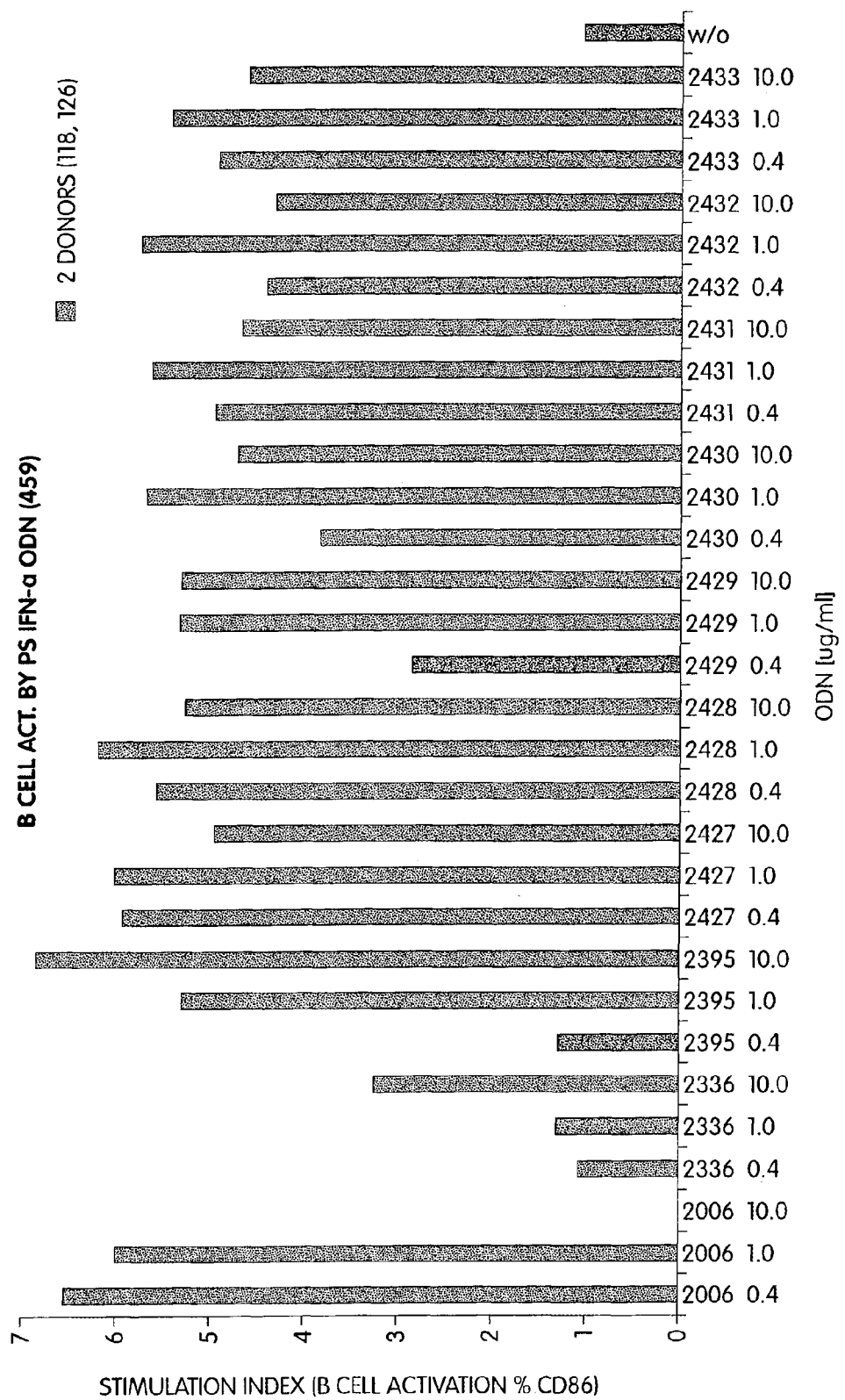
FIG. 9 is a bar graph depicting B cell activation as measured by percent CD86-positive cells in human PBMC cultured for 24 hours alone (w/o) or in the presence of the indicated ODN at the indicated concentrations (0.4, 1.0, or 10.0 μg/ml).
Figure 10:
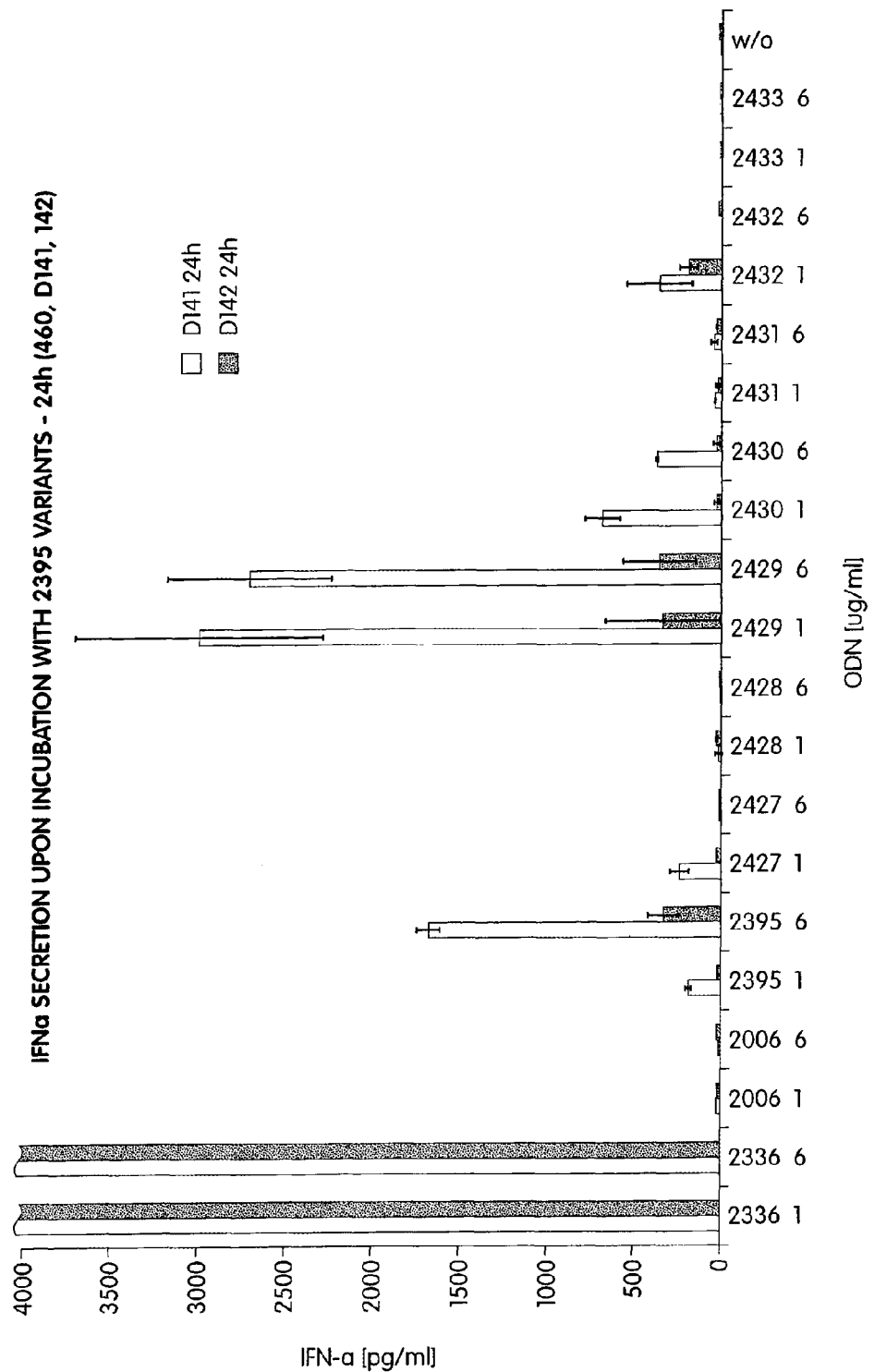
FIG. 10 is a bar graph depicting the amount of IFN-α (pg/ml) secreted by PBMC from two donors (D141, open bars, and D142, solid bars) following 24 hours of culture alone (w/o) or in the presence of the indicated ODN at the indicated concentrations (1 or 6 μg/ml).
Figure 11:
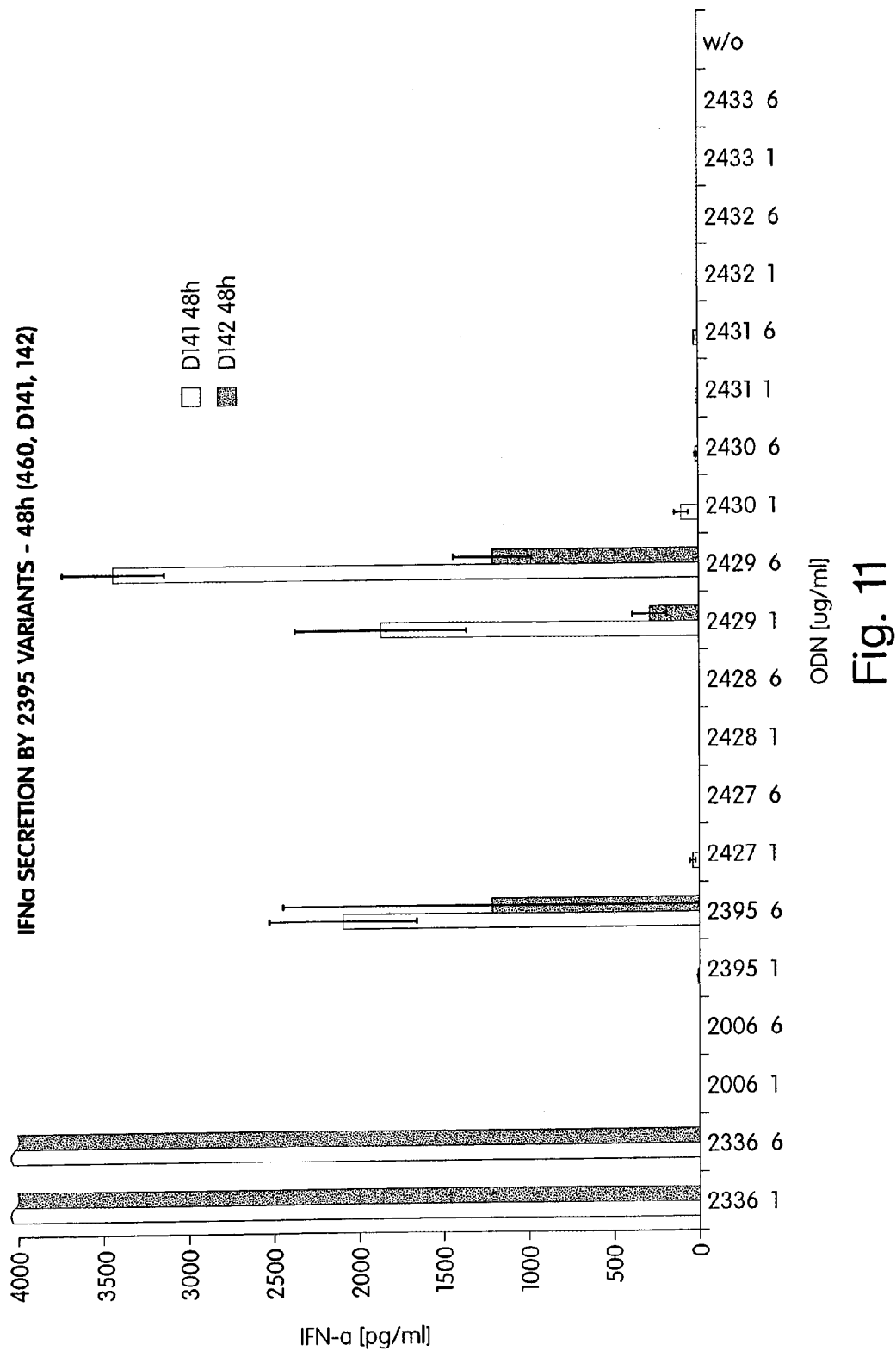
FIG. 11 is a bar graph depicting the amount of IFN-α (pg/ml) secreted by PBMC from two donors (D141, open bars, and D142, solid bars) following 48 hours of culture alone (w/o) or in the presence of the indicated ODN at the indicated concentrations (1 or 6 μg/ml).
Figure 12:
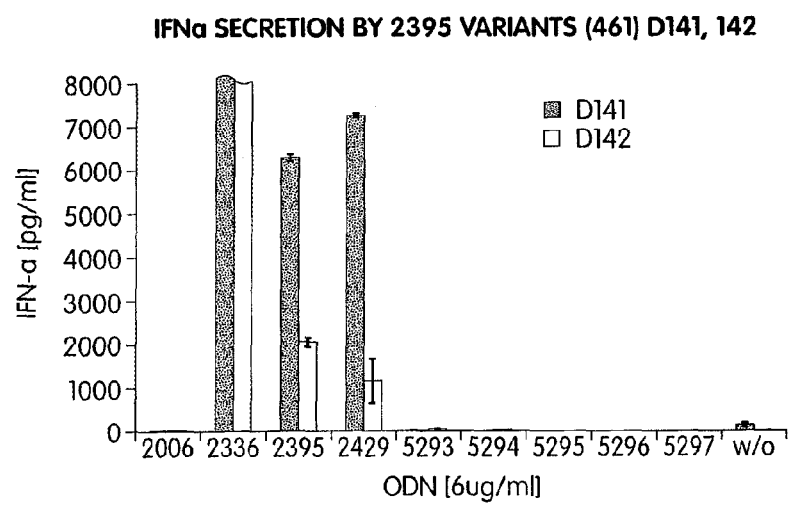
FIG. 12 is a bar graph depicting the amount of IFN-α (pg/ml) secreted by PBMC from two donors (D141, shaded bars, and D142, open bars) following 24 hours of culture alone (w/o) or in the presence of the indicated ODN at 6 μg/ml.

Reciprocal Relationship Between B-Cell Stimulation and NK Stimulation and IFN-α Secretion FIG. 9 shows another experiment, where ODN 2395 at a low concentration of 0.4 µg/ml was significantly weaker than ODN 2006 at inducing B cell expression of CD86. The other relatives of 2395 show a less marked loss of B cell stimulation. Interestingly, there is the suggestion of the same rank order for loss of B cell stimulation that had previously been seen for gain of NK stimulation: ODN 2429, followed by ODN 2430, are the weakest B cell stimulators among the 2395 relatives. This raises the possibility that the loss of B cell stimulation by the 2395-like ODN is closely related to the gain of NK stimulation and IFN-α secretion. FIG. 10 and FIG. 11 show the IFN-α induction is seen with ODN 2395 and ODN 2429, followed by ODN 2430. Table 4 and FIG. 12, from a separate experiment, also show the strong ability of ODN 2395 and ODN 2429 to induce IFN-α secretion in two different human donors (D141 and D142).

TABLE 4

IFN-α Secretion by Variants of ODN 2395[1]

| ODN, 6 µg/ml | IFN-α, pg/ml | |
| --- | --- | --- |
| | D141 | D142 |
| 2006 | 10 ± 10 | 7 ± 0.5 |
| 2336 | 83,297 ± 1876.5 | 53530.5 ± 4840 |
| 2395 | 6214 ± 84.5 | 2031 ± 96 |
| 2429 | 7215 ± 68 | 1117.5 ± 495 |
| 5293 | 10 ± 0.5 | 27 ± 27 |
| 5294 | 2.5 ± 0.1 | 23 ± 23 |
| 5295 | 5 ± 0.5 | 0 ± 0 |
| 5296 | 10 ± 0 | 10 ± 0 |
| 5297 | 10 ± 0.5 | 26.5 ± 1 |
| without(w/o) | 110 ± 77.5 | 12 ± 12 |

[1]Data expressed in units of pg/ml as mean ± standard deviation.

ODN sequences for Table 4
2006 TCGTCGTTTTGTCGTTTTGTCGTT (SEQ ID NO: 39)
2336 GGGGACGACGTCGTGGGGGGG (SEQ ID NO: 57)
2395 TCGTCGTTTTCGGCGCGCGCCG (SEQ ID NO: 1)
2429 TCGTCGTTTTCGGCGGCCGCCG (SEQ ID NO: 4)
5293 TCGTCGTTTTCGGCGGCCGCC (SEQ ID NO: 58)
5294 TCGTCGTTTTCGGCCGCCGCC (SEQ ID NO: 59)
5295 TCGTCGTTTTCGGCCGCCGCCG (SEQ ID NO: 60)
5296 TCGTCGTTTTCGCCGCCGCCG (SEQ ID NO: 61)
5297 TGCTGCTTTTCGGCGGCCGCCG (SEQ ID NO: 62)

Example 7

Characteristics of the GC-Rich Domain

Surprisingly, none of the ODN 5293-5297 demonstrated strong immune stimulatory responses. ODN 5293 contains a 10-base palindrome, but the palindrome differs from that in 2395 in that the central CG is inverted to a GC. However, it is believed that this change by itself cannot explain the loss of activity since ODN 2429 also has such an inversion. Rather, greater levels of activity may occur with a 12-base palindrome unless there is a central CG in the palindrome. However, ODN 2430 also has only a 10-base palindrome with a central GC dinucleotide. The immune stimulatory activity of ODN 2430 may be enhanced by the fact that it contains five CpG dinucleotides in the 3' terminus, whereas ODN 5293 contains only three.

ODN 5294 contains only a 6-base palindrome, which could possibly be related to its low activity. ODN 5295 likewise has no good palindrome. The low activity of ODN 5296 suggests that simple repeats of CCG are not sufficient to confer the immune stimulatory effects of ODN 2395. ODN 2397 has a perfect 12-base palindrome at the 3' end, but has no CpG motifs at the 5' end. Since the 12-base palindrome in ODN 5297 is the same at that in ODN 2429, it can be concluded that the 5' TCGTCG motif of ODN 2429 is important for its immune stimulatory activity. That is, it is believed that the presence of the neutralizing palindrome of ODN 2429 at one end of an oligonucleotide will be insufficient to provide immune stimulatory activity in the absence of at least one stimulatory motif at the other end.

Example 8

Effects on IFN-γ Production

Figure 13A:
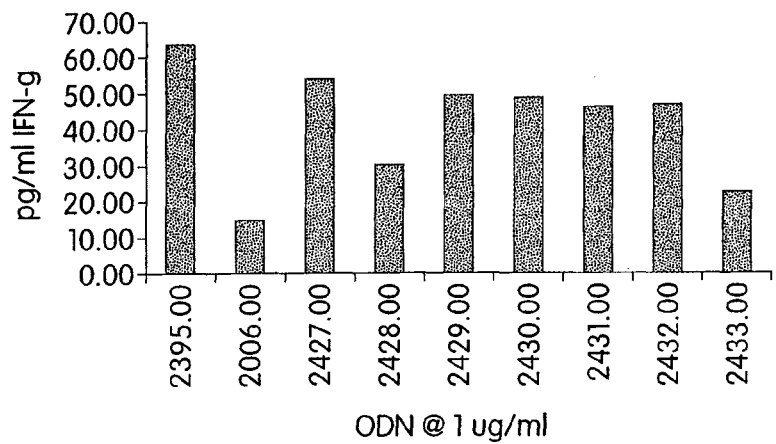
FIG. 13 is a series of three bar graphs depicting the amount of IFN-γ (pg/ml) secreted by PBMC following 24 hours of culture alone (n/a) or in the presence of the indicated ODN at the indicated concentrations (1, 3 or 10 μg/ml in panels A, B, and C, respectively).
Figure 13B:
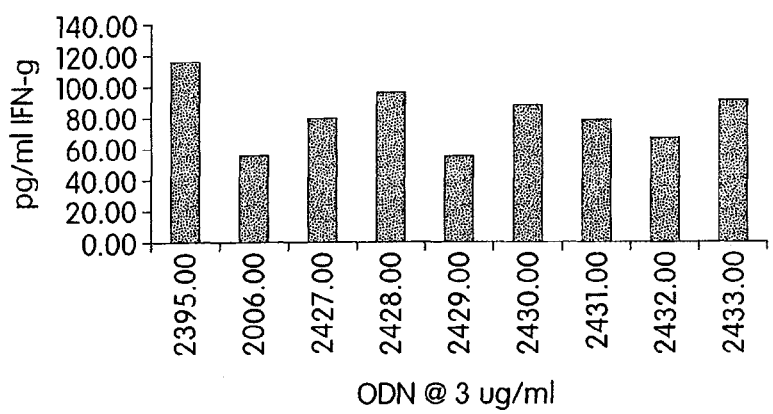
Figure 13C:
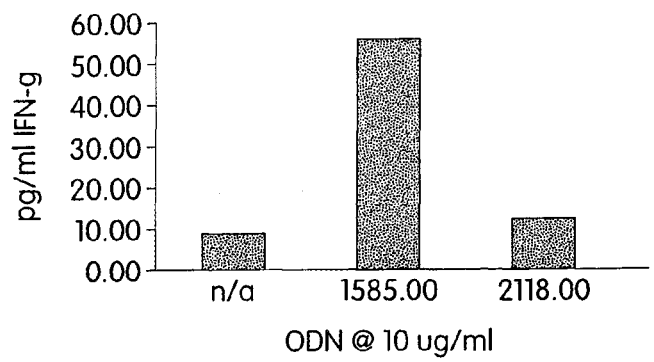

Several additional types of assays have been performed to better understand the range of immune stimulatory effects of this new class of immune stimulatory nucleic acid. FIG. 13 shows some of the effects of these ODN on IFN-γ production from the supernatants of human PBMCs. These cells were the same as those used in the experiments shown in Table 3, but the supernatants from the cultures were assayed for their IFN-γ levels. Panel C in FIG. 13 shows that SOS CpG ODNs such as ODN 1585 induce some IFN-γ production, whereas ODNs without the CpG motif (e.g., control ODN 2118) do not. Panels A and B of FIG. 13 show that ODN 2006 is relatively weak at inducing IFN-γ production, while ODN 2395 and its cousins are somewhat stronger.

Figure 14:
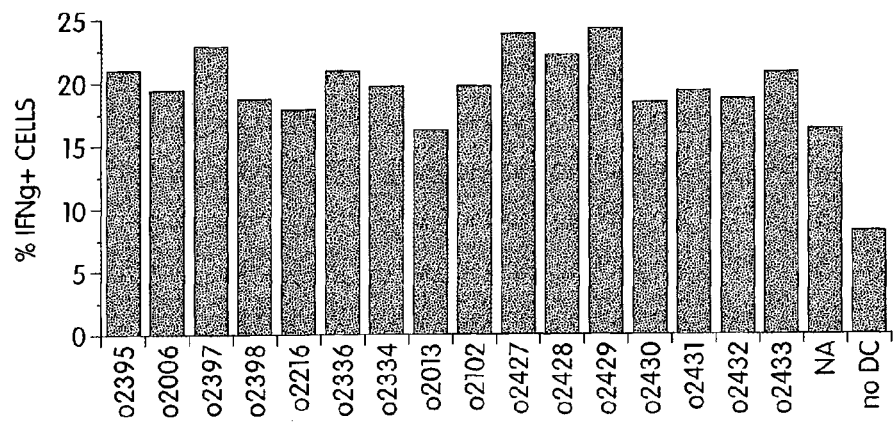
FIG. 14 is a bar graph depicting the percentage of CD3+ cells staining positive for IFN-γ following 48 hours of culture alone (NA) or in the presence of the indicated ODN.
Figure 15:
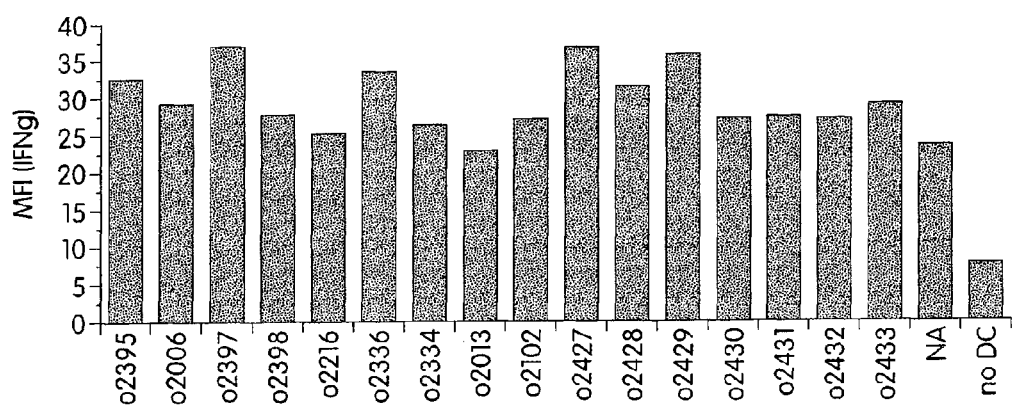
FIG. 15 is a bar graph depicting the mean fluorescence intensity (MFI) of IFN-γ staining in T cells following 48 hours of culture alone (NA) or in the presence of the indicated ODN.

Another set of studies was performed to examine the effects of these different ODN on dendritic cells. The plasmacytoid DC (pDC) is the source of the IFN-α that is produced in response to ODN 2395 and its relatives. The effects of the various ODN on myeloid DC (mDC) are relatively similar in that all of the ODN induce partially purified mDC to activate CD4+ T cells to produce IFN-γ (FIG. 14 and FIG. 15). Myeloid DC were isolated from a buffy coat and incubated with GM-CSF (4.4 ng/ml) and various ODN for 2 days. CD4+ naïve T cells were then isolated from a different donor and mixed with the DC at selected effector to target (E:T) ratios and incubated for 6 more days. Cells were then stained and analyzed by fluorescence activated cell sorting (FACS). Results were measured in terms of the percentage of CD3+ cells that stained for IFN-γ. FIG. 14 shows the percentage of T cells that stained positive for IFN-γ and FIG. 15 shows the mean fluorescence intensity (MFI) of IFN-γ staining in these T cells.

Example 9 not all GC-Rich Palindromes are Effective

Figure 16:
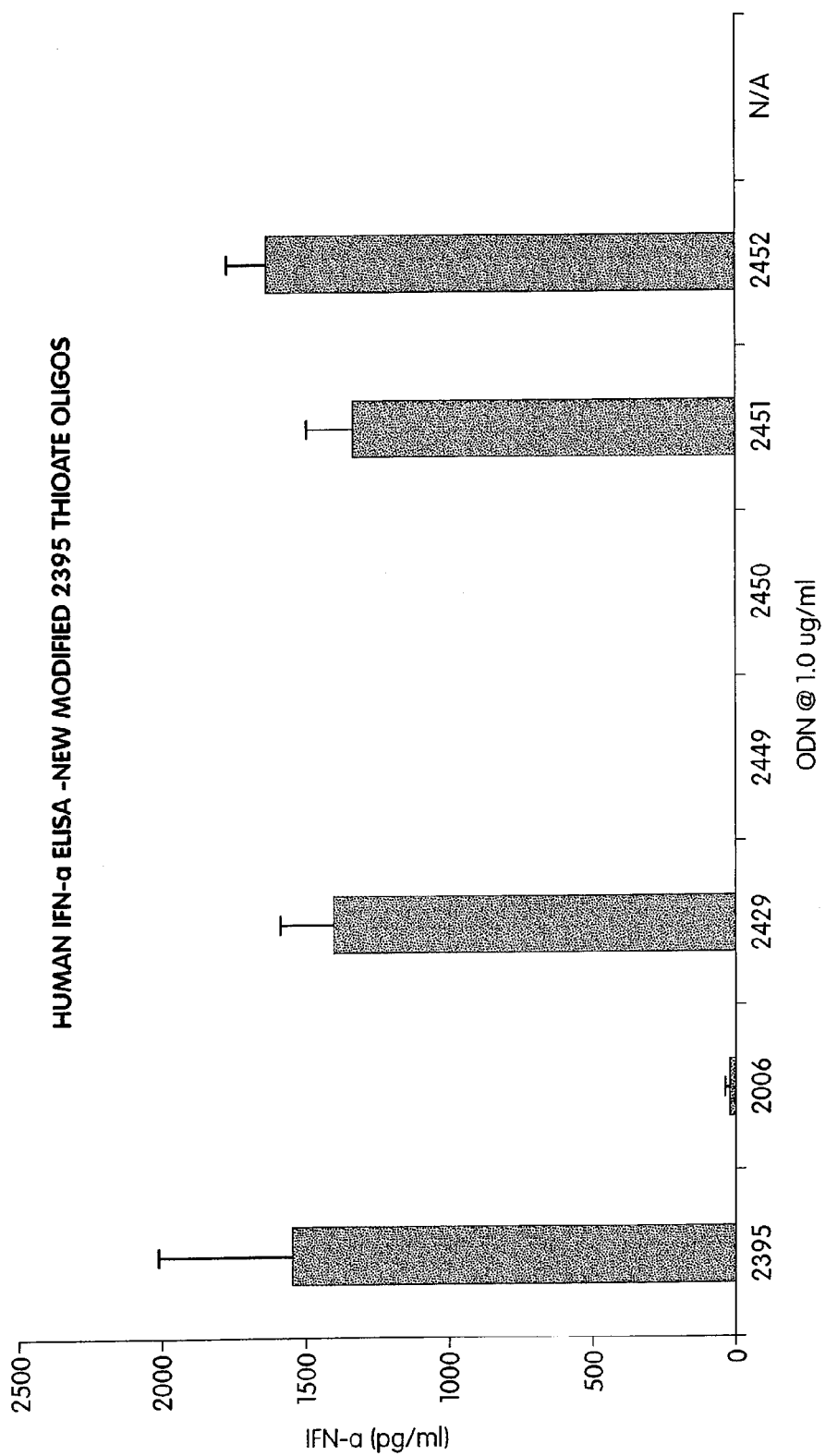
FIG. 16 is a bar graph depicting the amount of IFN-α (pg/ml) secreted by human PBMC following 24 hours of culture alone (N/A) or in the presence of the indicated ODN at 1.0 μg/ml.

Several additional ODN were synthesized in order better to understand the structural requirements for this new class of ODN. Since we noted that potent immune stimulatory ODN contained GC-rich palindromes, ODN 2449 (TCGTCGTTTTCGGGGGGCCCCC, SEQ ID NO: 9) and 2450 (TCGTCGTTTTCCCCCCGGGGGG, SEQ ID NO: 10) were synthesized to have GC-rich palindromes which were simply straight Gs followed by straight Cs, or straight Cs followed by straight Gs. As shown in FIG. 16, neither of these ODN induced IFN-α production.

Example 10

Effect of Orientation of Immune Stimulatory Sequence and Neutralizing Motif

ODN 2451 (TCGGCGCGCGCCGTCGTCGTTT, SEQ ID NO: 11) was synthesized to test the possibility that the 5' and 3' orientation of the "stimulatory" TCGTCG motif and the "neutralizing" CGGCGCGCGCCG (SEQ ID NO: 23) palindrome could be inverted without losing immune stimulatory activity. Indeed, ODN 2451 was highly stimulatory (FIG. 16). ODN 2452 (TCGTCGTTTTCGGCGCGCGCCGTTTT, SEQ ID NO: 12) was synthesized to determine whether additional sequence could be added to the 3' end of the CGGCGCGCCCCG (SEQ ID NO: 23) palindrome without reducing the immune stimulatory activity, provided the stimulatory TCGTCG motif was on the 5' end. Indeed, this ODN was also highly immune stimulatory (FIG. 16).

Example 11

Variants of ODN 2395 and their Induction of IFN-α

To study in more detail the structural requirements of this new class of ODN to induce IFN-α secretion, variants of ODN 2395 were synthesized and tested for their immunostimulatory activity. Table 5 summarizes the data concerning IFN-α induction.

Figure 17A:
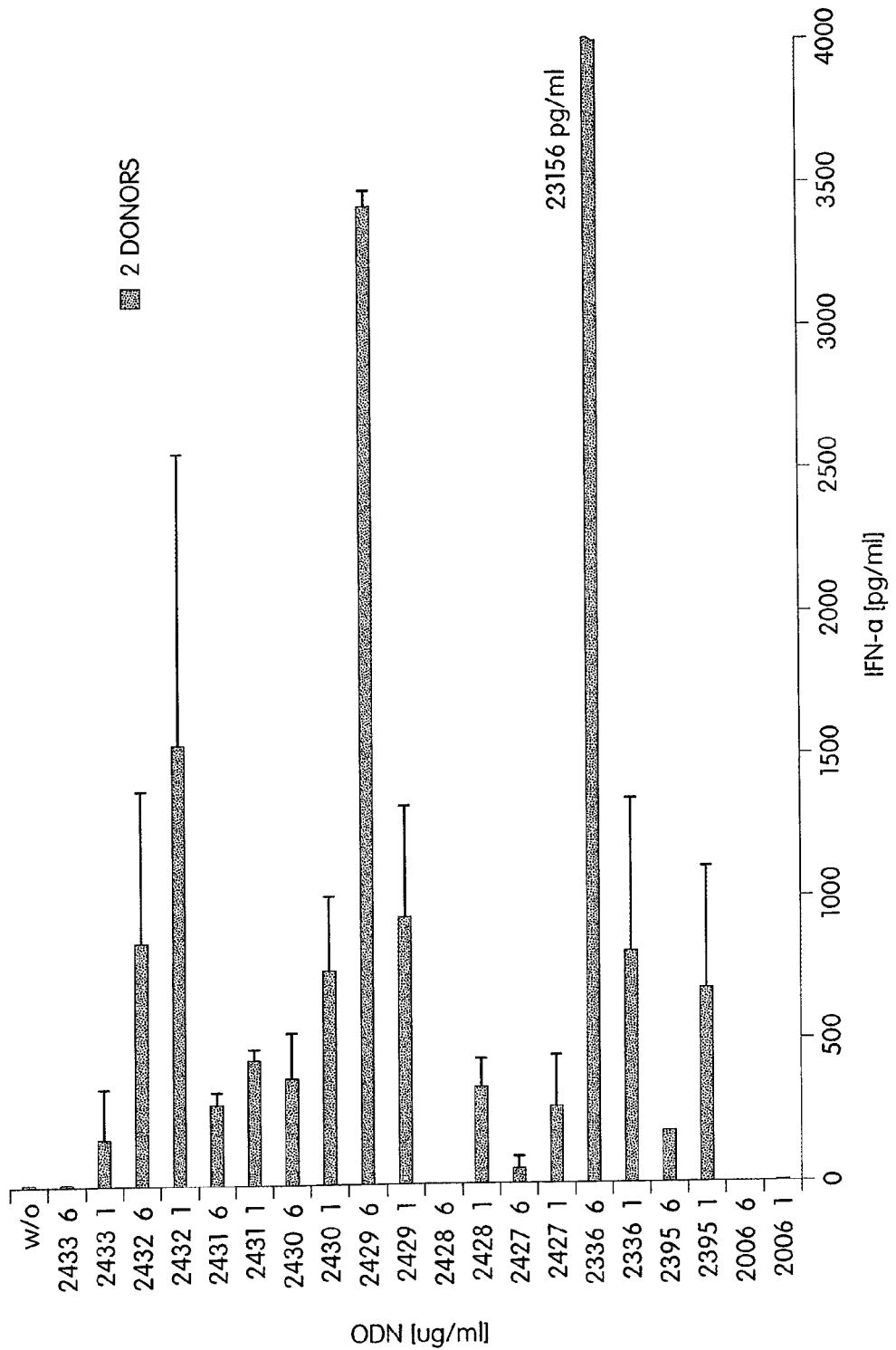
FIG. 17 is a pair of bar graphs depicting the amount of IFN-α (pg/ml) secreted by human PBMC following 24 or 48 hour culture alone (w/o) or in the presence of the indicated ODN at the indicated concentration (1 or 6 μg/ml). Panel A depicts results for PBMC pooled from two donors. Panel B depicts results for PBMC obtained from two donors (D141 and D142).

From the first set of experiments using the phosphorothioate ODNs 2395 and 2427-2433 it became clear that the palindromic sequence at the 3' end of the ODN has an important role for induction of IFN-α secretion by dendritic cells that are the main producers of IFN-α (see 2395 and 2429), although some ODN without such a palindrome at the 3' end (e.g., ODN 2430 and ODN 2432) also induced IFN-α in somewhat lower amounts (example in FIG. 17A). ODN 2395 and ODN 2429 induced the highest amounts of IFN-α, whereas 2006 (class B ODN) induced none to minimal amounts, and ODN 2336 (class A ODN) induced large amounts of this cytokine. Most experiments demonstrated that ODN 2429 induced even higher amounts of this cytokine (FIG. 17B). An introduction of an additional TCG motif (e.g., ODN 2427 and ODN 2428) appeared to have negative effects

TABLE 5

Variants of ODN 2395 and their induction of IFN-α[1,2]

| ODN | SEQ ID NO: | Sequence | Palindrome | Description | IFN-α Induction |
|---|---|---|---|---|---|
| 2006 | 39 | tcgtcgttttgtcgttttgtcgtt | / | ODN class B | − |
| 2336 | 57 | ggGGACGACGTCCTGggggggG | + | ODN class A | +++++ |
| 2395 | 1 | tcgtcgttttcggcgcgcgccg | + | 2006-2136 | ++ |
| 2427 | 2 | tcgtcgttttcgtcgcgcgccg | − | | − |
| 2428 | 3 | tcgtcgttttcgtcgcgcggcg | − | | − |
| 2429 | 4 | tcgtcgttttcggcggccgccg | − | cg→gc by preserving palindrome | +++ |
| 2430 | 5 | tcgtcgttttcggcgcgccgcg | − | | + |
| 2431 | 6 | tcgtcgttttcggcgcgccgcg | − | | +/− |
| 2432 | 7 | tcgtcgttttcggcccgcgcgg | − | | + |
| 2433 | 8 | tcgtcgttttccgcgccggag | − | | − |
| 5293 | 58 | tcgtcgttttcggcggccgcc | (+) | 2429 w/o 3' g | − |
| 5294 | 59 | tcgtcgttttcggccgccgcc | − | 3xgcc w/o 3' g | − |
| 5295 | 60 | tcgtcgttttcggccgccgccg | − | 5295 w/3' g | − |
| 5296 | 61 | tcgtcgttttcgccgccgccg | − | | − |
| 5297 | 62 | tgctgcttttcggcggccgcg | + | gc of 2429 | − |
| 5327 | 14 | tgctzgttttzggzgzgzgzzg | + | 2395 w/methyl-c (z) | + |
| 5328 | 15 | tgctgcttttcggcgcgcgcg | + | gc of 2395 | − |
| 2136 | 19 | tcctgacgttcggcgcgcgcc | (+) | | +/− |
| 5315 | 13 | tcctgacgttcggcgcgcgcg | + | 2136 w/3' g longer palindrome | + |
| 5329 | 16 | tcgtcgttttcgcgcgcgcg | + | 2006 +1631 | (−) |

[1]Underlined are nucleotides that differ from 2395; palindromic sequences are in italics.
[2]All except ODN 2336, that represents a chimeric backbone ODN (capitals indicate phosphodiester linkage and lower case represent phosphorothioate linkage), are completely phosphorothioate ODNs.

on IFN-α secretion. Based on data from these and other studies of ODN 2186, the gcc at the 3' end seemed to play a possible role in the observed effects.

Therefore, we tested another set of ODNs all having GCC sequences at the 3' end. None of these ODN were observed to induce IFN-α. Therefore, only GCC itself in a palindrome seems not to be sufficient for the observed effects.

In addition, ODN 5297 with a TGC at the 5' end did not induce any IFN-α despite bearing the palindromic 3' sequence. This led to the conclusion that not only the 3' palindromic sequence but also the 5' TCG motif is important for the activity of these ODNs.

This was confirmed by using ODN 5328 (2395 with 5' TGC motif). In contrast to methylation of class A ODNs, methylation at least of the 5' motif decreased, but did not abrogate, IFN-α secretion. This finding is in accordance with results obtained with class B ODNs. Nevertheless, an ODN with part of the 3' palindrome but a different sequence at the 5' end with only one CpG dinucleotide (ODN 2136) also induced IFN-α. In preliminary results using this ODN and an ODN with the full 3' palindrome (ODN 5315), ODN 5315 was better than ODN 2136 but not as good as ODN 2395.

The fact that ODN 5329 seems to induce no or only very low amounts of IFN-α although having a full CG palindrome at the 3' end indicates that specific palindromic sequences are preferred for IFN-α activity.

Example 12

Reciprocal Relationship Between B-Cell Activation and Induction of IFN-α

Figure 18:
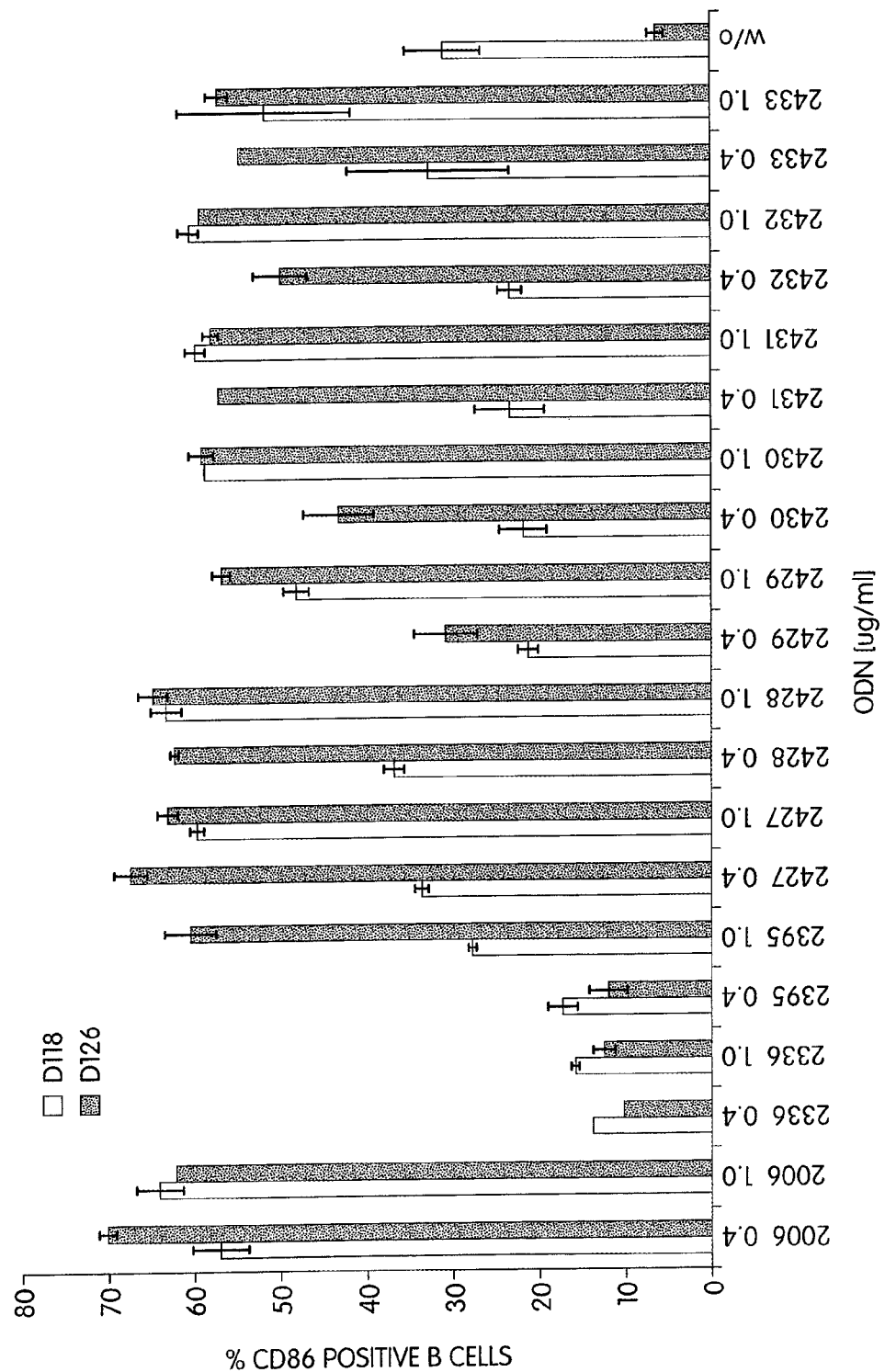
FIG. 18 is a bar graph depicting the percent CD86-positive B cells following 24 hours of culture alone (w/o) or in the presence of the indicated ODN at the indicated concentrations (0.4 and 1.0 μg/ml).

An additional B-cell activation experiment was performed with a panel of some of the ODNs of Example 11 (FIG. 18). The results indicated that the better is an ODN for induction of IFN-α, the less active it is on B cells (compare especially ODNs 2006, 2336, 2395 and 2429). Nevertheless, it also demonstrated that all of these ODNs were superior to 2336 (class A ODN) in stimulating B cells.

Example 13

Effect on Secretion of IFN-γ

Figure 19C:
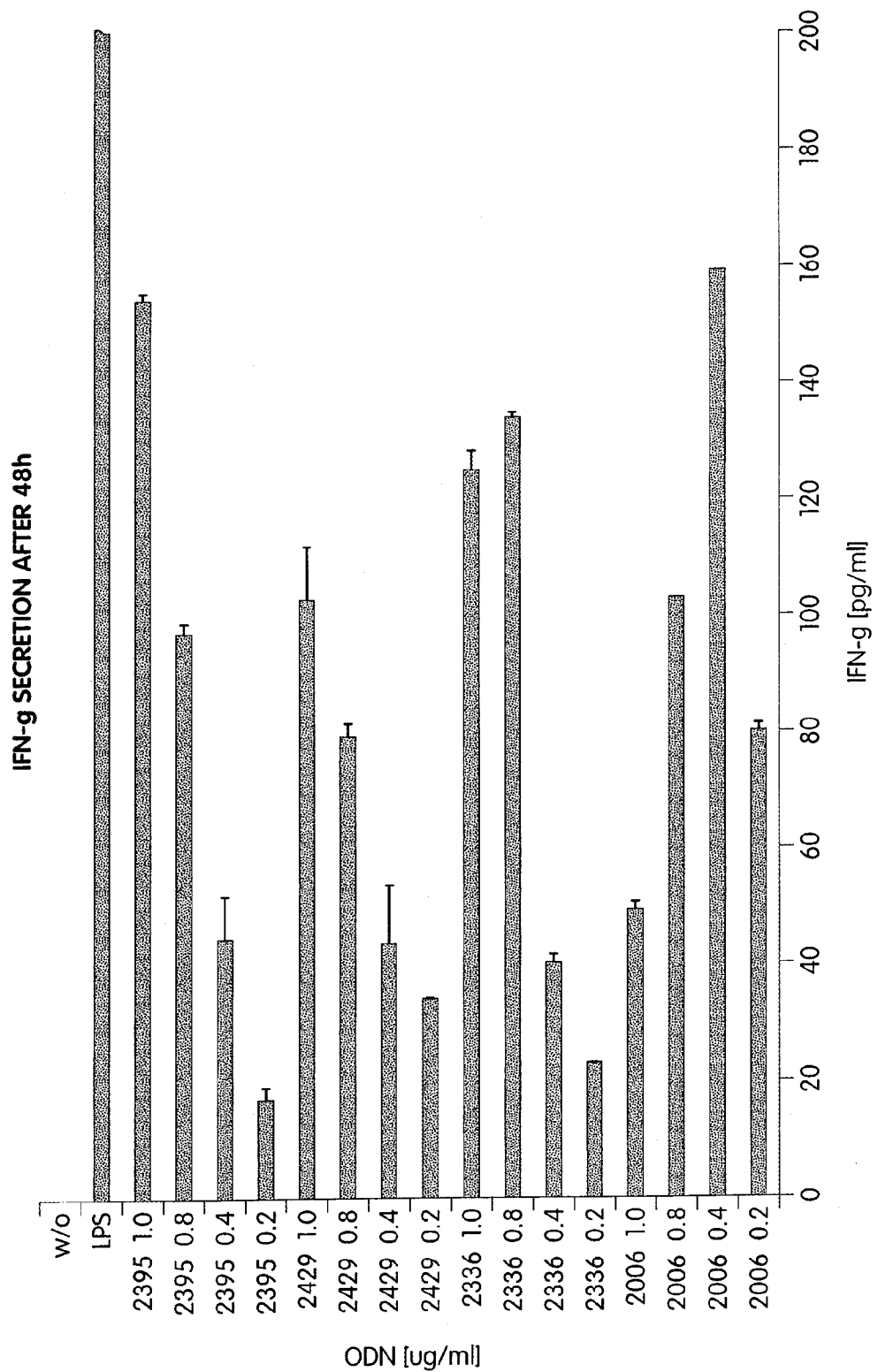
FIG. 19 is a series of three bar graphs depicting the concentration of IFN-γ (pg/ml) in culture supernatants of human PBMC after incubation alone (w/o), with LPS, or with the indicated ODN at the indicated concentrations (0.2 to 1.0 μg/ml) for 6 hours (panel A), 24 hours (panel B), or 48 hours (panel C).

We also determined secretion of IFN-γ upon incubation of PBMCs with different concentrations of ODN at different time points (FIG. 19 A-C). The ODNs tested induced IFN-γ secretion with the rank order 2336>2395, 2429>2006. Nevertheless, the difference between the ODNs was not as clear as by using IFN-α as a read-out.

Example 14

Effect on IFN-γ in MLR

Figure 20:
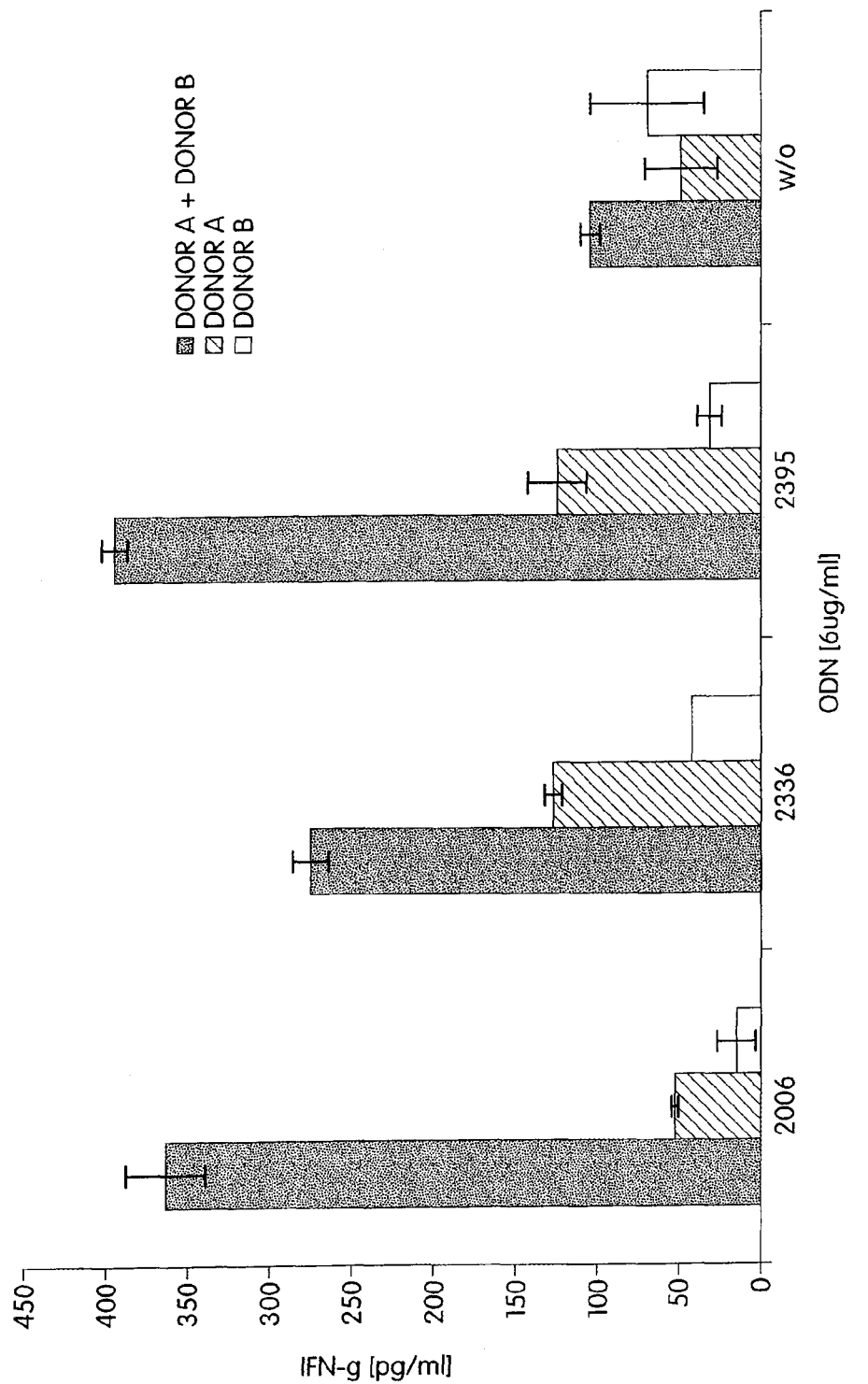
FIG. 20 is a bar graph depicting the amount IFN-γ (pg/ml) generated in a two-way mixed lymphocyte reaction (MLR) in which lymphocytes obtained from two donors were cultured for 24 hours alone (w/o) or in the presence of the indicated ODN at 6 μg/ml and then mixed.

We also determined the effect of these ODN on the induction of IFN-γ in a mixed lymphocyte reaction (MLR). In this setting lymphocytes of one donor respond to antigens expressed on cells of another donor. The results demonstrated that ODNs 2006, 2336, as well as 2395 were able to enhance IFN-γ secretion during such an antigen-specific response (FIG. 20). This indicated that all these ODN were able to enhance the reactivity to specific antigen(s).

Example 15

ODN 2395 Induces Less IL-10 than ODN 2006

Figure 21A:
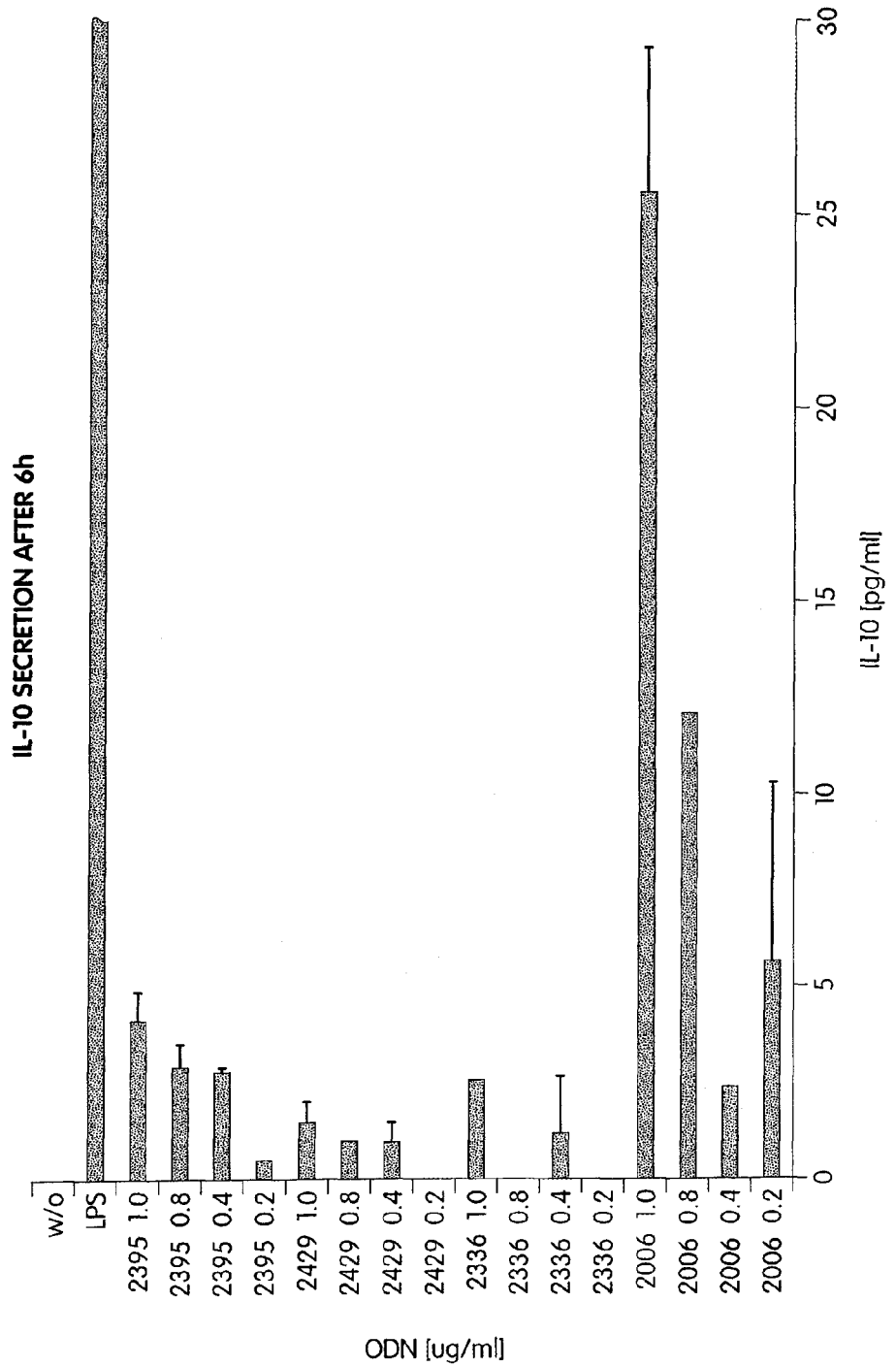
FIG. 21 is a series of three bar graphs depicting the concentration of IL-10 (pg/ml) in culture supernatants of human PBMC after incubation alone (w/o), with LPS, or with the indicated ODN at the indicated concentrations (0.2 to 1.0 μg/ml) for 6 hours (panel A), 24 hours (panel B), or 48 hours (panel C).
Figure 21B:
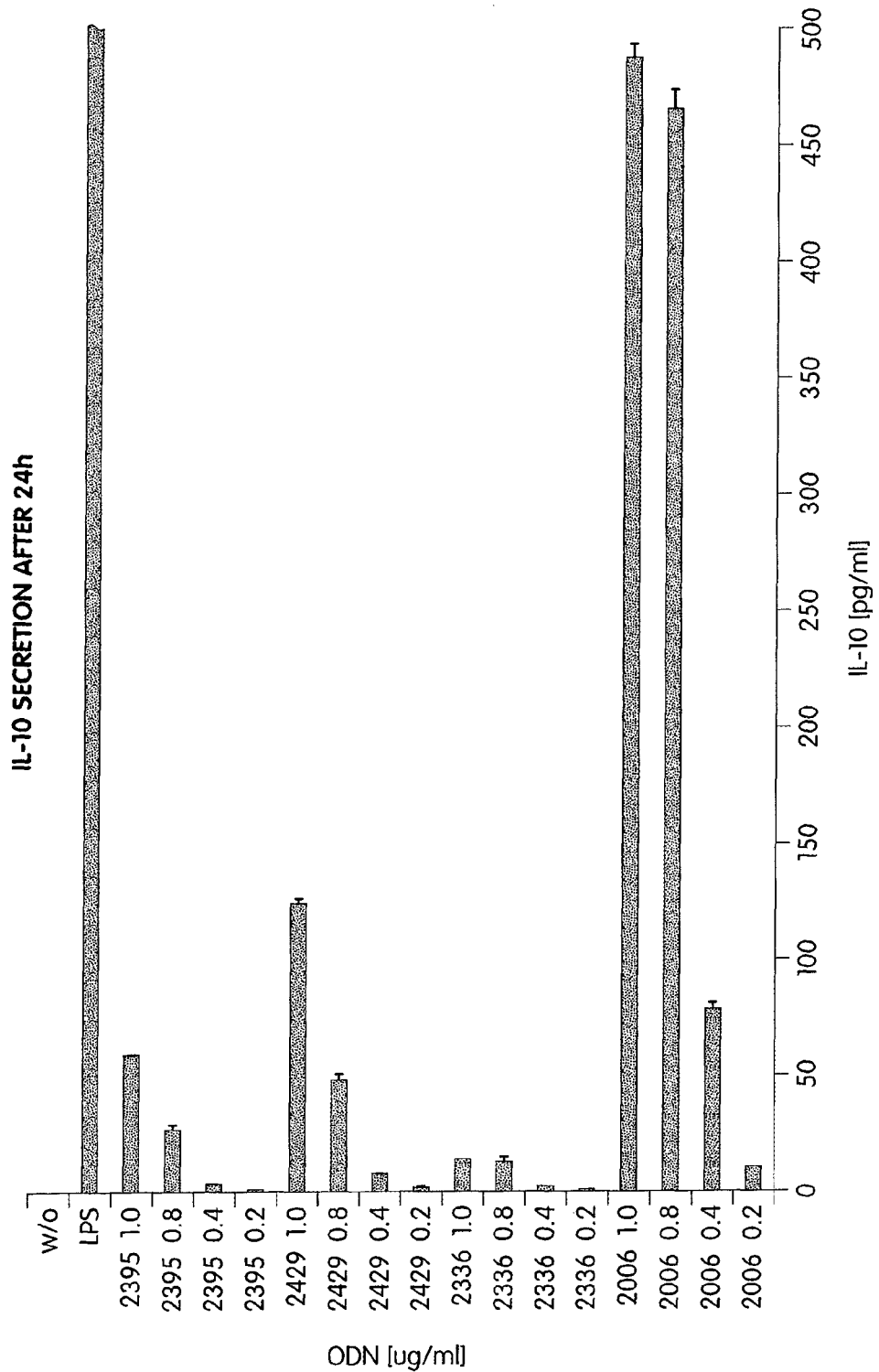

A further set of experiments focused on the induction of the pro-inflammatory cytokine IL-10. Again, as before for IFN-γ, PBMCs were incubated for different times and with different concentrations of ODNs (FIG. 21 A-C). The results demonstrate that, as shown before, ODN 2006 induces relatively high amounts of IL-10 in contrast to ODN 2336 that induces only minimal to low amounts. In contrast, ODNs 2395 as well as ODN 2429 induce more IL-10 than ODN 2336 but less than ODN 2006. This again confirms that ODN of this new class of immune stimulatory ODN have stimulatory activities that place them between those described for ODNs of class A and class B.

Example 16

ODN 2395 Induces Less TNF-α than ODN 2006 but More than ODN 8954

Human PBMCs were cultured for 6 hours with 1.6 μg/ml of ODN 2006, 8954, 2395, 2429, or LPS, and supernatants were then harvested and TNF-α measured by specific ELISA. Results are shown in Table 6.

TABLE 6

Induction of TNF-α by representative ODN of different classes

| ODN | TNF-α, pg/ml |
|---|---|
| (LPS) | >120 |
| 2006 | 40 |
| 2429 | 35 |
| 2395 | 21 |
| 8954 | 14 |
| none | 16 |

Additional experiments indicated that cytokines IL-5 as well as IL-15 could not be detected in our experimental settings upon incubation of PBMCs with these ODNs.

Example 17

Induction of IP-10

Figure 22:
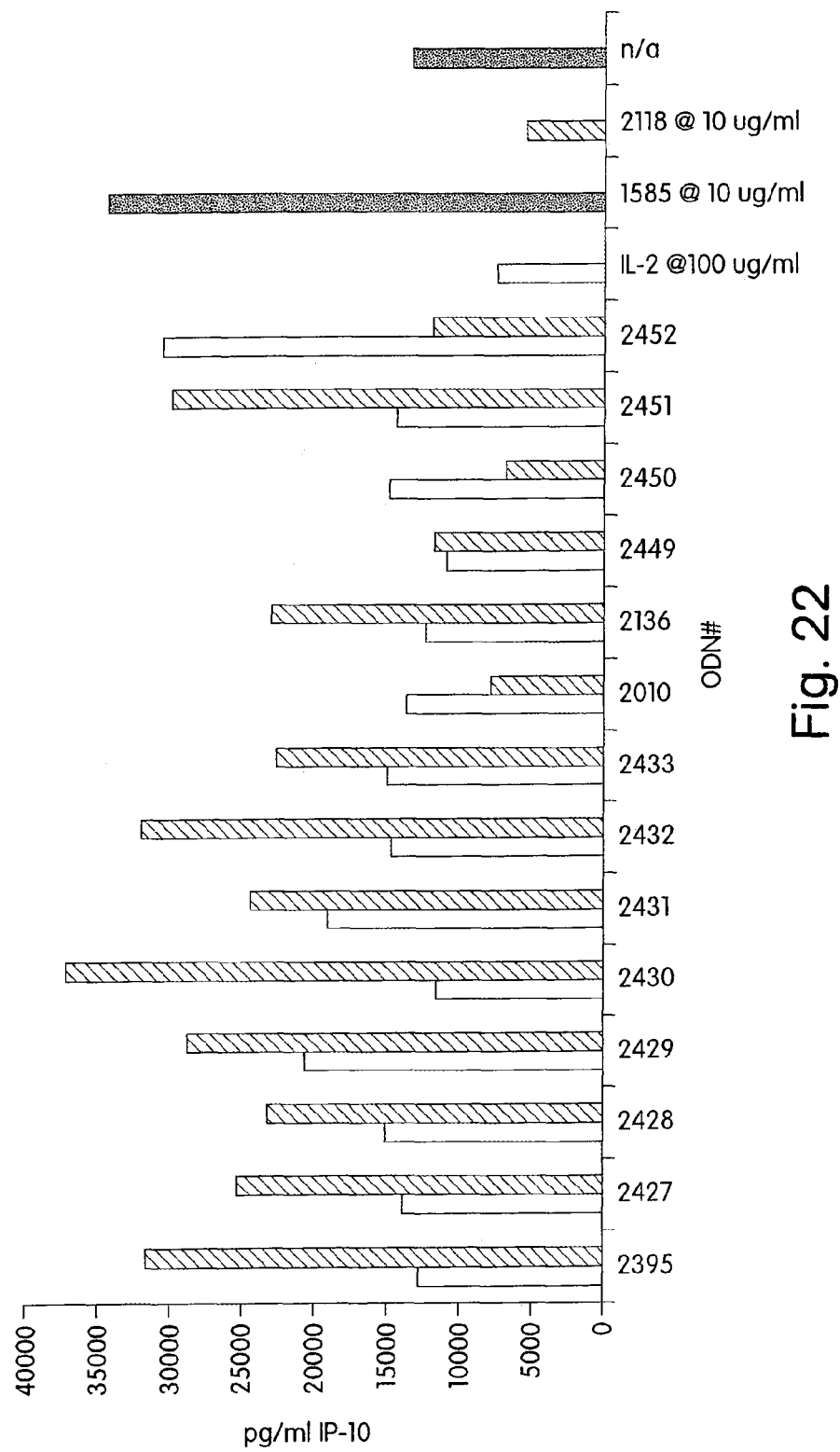
FIG. 22 is a bar graph depicting the amounts of IP-10 (pg/ml) in PBMC supernatants after 24 hours of incubation alone (n/a) or in the presence of controls (IL-2, ODN 1585 (GGGGTCAACGTTGAGGGGGG, SEQ ID NO: 35) and ODN 2118 (GGGGTCAAGCTTGAGGGGGG, SEQ ID NO: 36)) or various indicated ODN at either 0.6 μg/ml (open bars) or 3.0 μg/ml (solid bars).

Human PBMCs were cultured either alone, in the presence of IL-2, in the presence of control ODN 1585 or control ODN 2118 at 10 μg/ml, or in the presence of various ODN at 0.6 or 3.0 μg/ml. Supernatants were harvested after 24 hours and IP-10 was measured by specific enzyme-linked immunosorbant assay (ELISA). Results are shown in FIG. 22. ODNs 2395, 2429, 2430, 2432, and 2451 at 3.0 μg/ml, and ODN 2452 at 0.6 μg/ml, all induced large amounts of IP-10.

Example 18

Induction of IFN-α

Figure 23A:
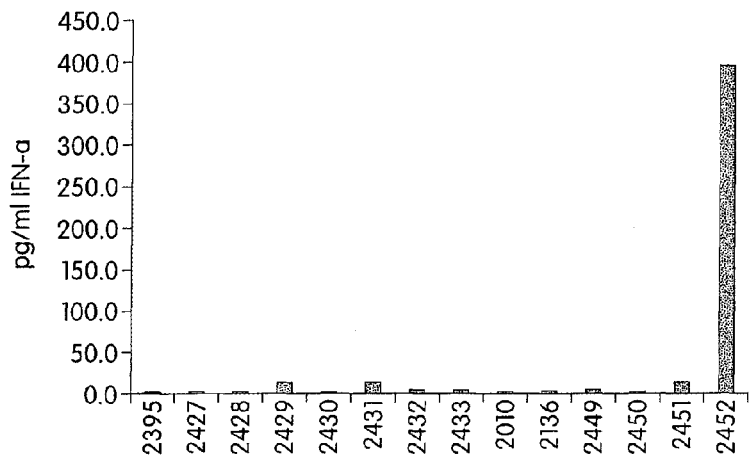
FIG. 23 is a pair of bar graphs depicting the amounts of IFN-α (pg/ml) in PBMC supernatants after 24 hours of incubation alone (n/a) or in the presence of controls (IL-2, ODN 1585, and ODN 2118) or various indicated ODN at either 0.6 μg/ml (panel A) or 3.0 μg/ml (panel B).
Figure 23B:
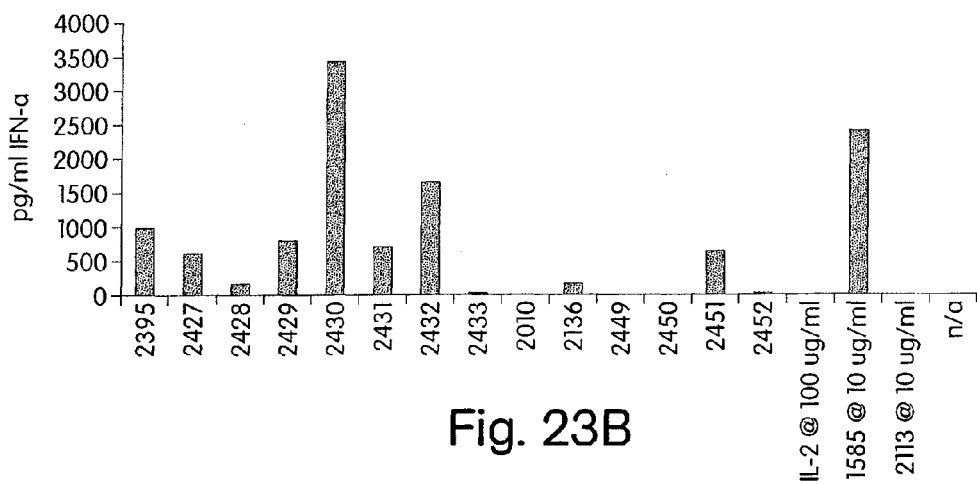

Human PBMCs were cultured either alone, in the presence of IL-2, in the presence of control ODN 1585 or control ODN 2118 at 10 μg/ml, or in the presence of various ODN at 0.6 or 3.0 μg/ml. Supernatants were harvested after 24 hours and IFN-α was measured by specific ELISA. Results are shown in FIG. 23A (ODN at 0.6 μg/ml) and FIG. 23B (ODN at 3.0 μg/ml). ODNs 2395, 2427, 2429, 2430, 2431, 2432, and 2451 at 3.0 μg/ml, and ODN 2452 at 0.6 μg/ml, all induced large amounts of IFN-α.

Example 19

Induction of IFN-γ

Figure 24:
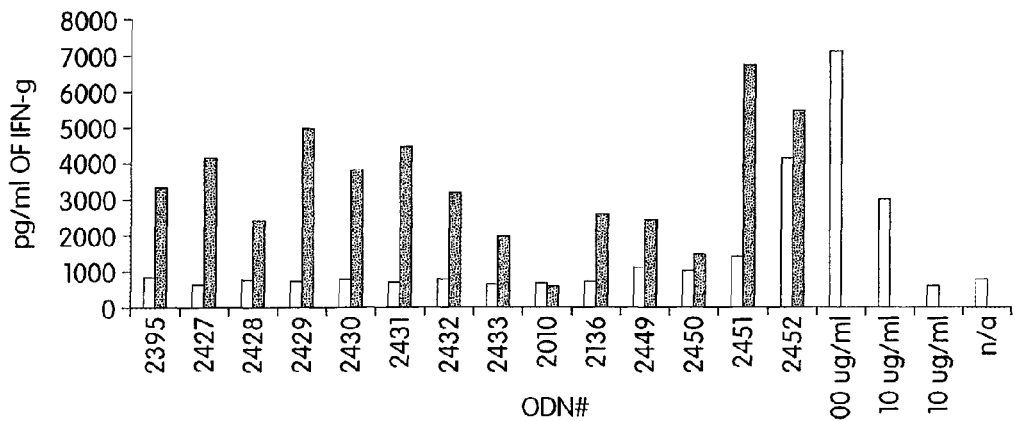
FIG. 24 is a bar graph depicting the amounts of IFN-γ (pg/ml) in PBMC supernatants after 24 hours of incubation alone (n/a) or in the presence of controls (IL-2, ODN 1585, and ODN 2118) or various indicated ODN at either 0.6 μg/ml (open bars) or 3.0 μg/ml (filled bars).

Human PBMCs were cultured either alone, in the presence of IL-2, in the presence of control ODN 1585 or control ODN 2118 at 10 µg/ml, or in the presence of various ODN at 0.6 or 3.0 µg/ml. Supernatants were harvested after 24 hours and IFN-γ was measured by specific ELISA. Results are shown in FIG. 24. ODNs 2395, 2427, 2429, 2430, 2431, 2432, 2451 and 2452 at 3.0 µg/ml, and ODN 2352 at 0.6 µg/ml, all induced large amounts of IFN-γ.

Example 20

Induction of IL-6

Figure 25:
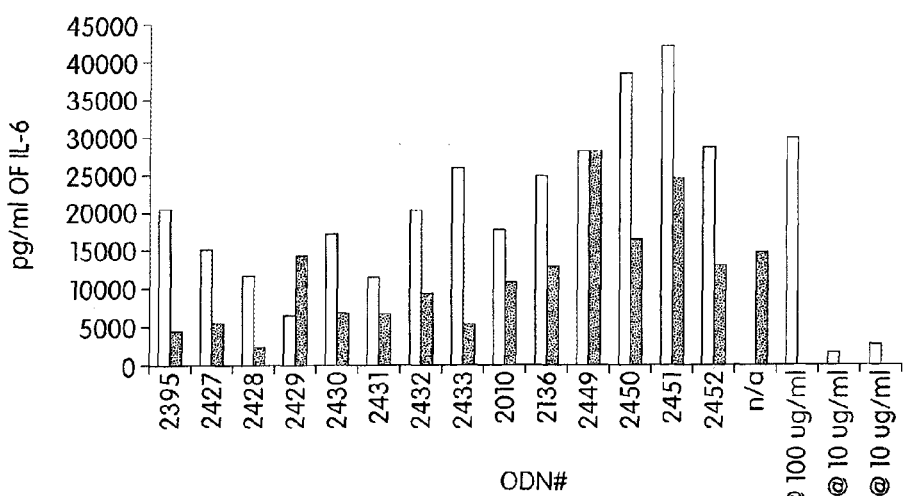
FIG. 25 is a bar graph depicting the amounts of IL-6 (pg/ml) in PBMC supernatants after 24 hours of incubation alone (n/a) or in the presence of controls (IL-2, ODN 1585, and ODN 2118) or various indicated ODN at either 0.6 μg/ml (open bars) or 3.0 μg/ml (filled bars).

Human PBMCs were cultured either alone, in the presence of IL-2, in the presence of control ODN 1585 or control ODN 2118 at 10 µg/ml, or in the presence of various ODN at 0.6 or 3.0 µg/ml. Supernatants were harvested after 24 hours and IL-6 was measured by specific ELISA. Results are shown in FIG. 25. ODNs 2395, 2430, 2432, 2433, 2136, 2449, 2450, 2451 and 2452 at 0.6 µg/ml, and ODN 2449 and ODN 2451 at 3.0 µg/ml, all induced large amounts of IL-6.

Example 21

Induction of IFN-α

Human PBMCs were cultured either alone or in the presence of various ODN at 3.0 or 6.0 µg/ml. ODNs included 2006, 8954, 2395, 2449, 2450, 2451, 2452, 5373 (CG-GCGCGCGCCG, SEQ ID NO: 23), 5374 (CGGCGCGCGC-CGCGGCGCGCCG, SEQ ID NO: 24), 5375 (CG-GCGCGCGCCGTCGTCGTTT, SEQ ID NO: 25), 5376 (TCGGCGCGCGCCGTGCTGCTTT, SEQ ID NO: 26), and 5377 (CCGCCGTTTTCGGCGCGCGCCG, SEQ ID NO: 27). Supernatants were harvested after 24 hours and IFN-α was measured by specific ELISA. Results are shown in FIG. 26. ODNs 2395, 2451, 2452, and 5376 all induced IFN-α.

Example 22

Induction of IFN-α by ODN 5515 and ODN 5516

Human PBMCs obtained from two donors (D346 and D240) were cultured either alone or in the presence of ODN 2006, ODN 5515, or ODN 5516 at 0.8, 2.4, or 6.0 µg/ml. Supernatants were harvested after 24 hours and IFN-α was measured by specific ELISA. Results are shown in Table 7. ODN 5515 and ODN 5516 induced IFN-α more effectively than ODN 2006, particularly at ODN concentrations of 2.4 and 6.0 µg/ml.

Example 23

Induction of IFN-α by ODN 20184, 20185, and 20186

Human PBMCs obtained from three donors (D445, D446, and D448) were cultured either alone or in the presence of ODN 2006, ODN 20184, ODN 20185, or ODN 20186 at 0.05, 0.1, 0.2, 0.5, or 1.0 µg/ml. Supernatants were harvested after 24 hours and IFN-α was measured by specific ELISA. Results are shown in Table 8. ODN 20184, ODN 20185, and ODN 20186 induced IFN-α more effectively than ODN 2006, particularly at 0.2-0.5 µg/ml.

TABLE 7

Induction of IFN-α (pg/ml) by ODN 5515 and ODN 5516

| ODN | Conc. µg/ml | D346 Mean ± SD | D240 Mean ± SD |
|---|---|---|---|
| 2006 | 0.8 | 18.5 ± 13.8 | 36 ± 3.3 |
|  | 2.4 | 0 ± 0 | 19.7 ± 6.4 |
|  | 6 | 2.7 ± 0 | 2.8 ± 0 |
| 5515 | 0.8 | 34.1 ± 6.9 | 16.5 ± 2.8 |
|  | 2.4 | 36.6 ± 2.1 | 106.7 ± 17.3 |
|  | 6 | 39.2 ± 26.5 | 127.3 ± 7.7 |
| 5516 | 0.8 | 4.3 ± 0 | 22.3 ± 0.1 |
|  | 2.4 | 31.9 ± 0 | 172.5 ± 82.3 |
|  | 6 | 26.6 ± 19 | 90.4 ± 15.4 |
| none | — | 0 ± 0 | 20.9 ± 6.5 |

TABLE 8

Induction of IFN-α (pg/ml) by ODN 20184, 20185, and 20186

| ODN | Conc. µg/ml | D445 Mean ± SD | D446 Mean ± SD | D448 Mean ± SD |
|---|---|---|---|---|
| 2006 | 0.05 | 5.2 ± 0.0 | 58.8 ± 1.9 | 0.9 ± 0.0 |
|  | 0.1 | 27.7 ± 14.4 | 283.5 ± 16.1 | 23.5 ± 3.8 |
|  | 0.2 | 54.9 ± 17.6 | 503.7 ± 9.7 | 39.1 ± 5.0 |
|  | 0.5 | 61.1 ± 14.6 | 227.8 ± 12.7 | 49.8 ± 0.4 |
|  | 1.0 | 26.4 ± 15.5 | 142.6 ± 23.1 | 48.7 ± 29.8 |
| 20184 | 0.05 | 25.6 ± 2.1 | 88.0 ± 12.2 | 0.0 ± 0.0 |
|  | 0.1 | 32.9 ± 7.3 | 691.2 ± 32.3 | 129.1 ± 24.8 |
|  | 0.2 | 256.2 ± 8.2 | 2155.1 ± 35.1 | 314.0 ± 22.2 |
|  | 0.5 | 757.2 ± 5.7 | 2171.8 ± 95.9 | 268.7 ± 15.9 |
|  | 1.0 | 194.3 ± 5.7 | 1181.9 ± 15.1 | 5.8 ± 3.4 |
| 20185 | 0.05 | 65.0 ± 10.8 | 217.9 ± 28.4 | 54.3 ± 14.2 |
|  | 0.1 | 63.6 ± 1.3 | 467.4 ± 23.7 | 150.9 ± 5.9 |
|  | 0.2 | 79.3 ± 2.4 | 1420.5 ± 83.7 | 160.2 ± 5.5 |
|  | 0.5 | 281.3 ± 0.2 | 1965.7 ± 72.3 | 162.4 ± 3.8 |
|  | 1.0 | 176.9 ± 12.5 | 1710.3 ± 19.7 | 181.1 ± 0.1 |
| 20186 | 0.05 | 21.9 ± 1.7 | 223.1 ± 1.2 | 79.8 ± 1.6 |
|  | 0.1 | 58.3 ± 7.6 | 812.2 ± 28.1 | 111.3 ± 6.8 |
|  | 0.2 | 153.6 ± 1.5 | 1302.5 ± 56.2 | 193.5 ± 10.5 |
|  | 0.5 | 267.7 ± 7.9 | 1744.1 ± 54.7 | 227.4 ± 6.9 |
|  | 1.0 | 153.0 ± 0.3 | 1113.6 ± 6.4 | 13.7 ± 15.4 |
| Medium | — | 0.0 ± 0.0 | 12.8 ± 2.0 | 64.8 ± 32.7 |
|  | — | 0.0 ± 0.0 | 45.3 ± 12.9 | 36.4 ± 2.6 |

Example 24

Induction of IFN-α by ODN 8954, 5569, and 5570

Human PBMCs obtained from three donors (D521, D525, and D526) were cultured either alone or in the presence of ODN 2006 (SEQ ID NO: 39), ODN 8954, ODN 5569 (TIGTIGTTTTCGGCGGCCGCCG SEQ ID NO: 63), or ODN 5570 (TCITCITTTTCGGCGGCCGCCG SEQ ID NO: 70) at 0.03, 0.06, 0.125, 0.25, or 1.0 µg/ml. Supernatants were harvested after 24 hours and IFN-α and IL-10 were measured by specific ELISA. Results are shown in Table 9 and 10.

TABLE 9

Induction of IFN-α (pg/ml) by ODN 8954, 5569, and 5570

| ODN | Conc. µg/ml | D521 Mean ± SD | D525 Mean ± SD | D526 Mean ± SD |
|---|---|---|---|---|
| 2006 | 0.03 | 238.674 | 239.286 | 216.393 |
|  | 0.06 | 2405.63 | 385.161 | 126.516 |
|  | 0.125 | 3826.53 | 549.612 | 86.173 |
|  | 0.25 | 2248.94 | 532.67 | 74.493 |
|  | 1.0 | 362.74 | 161.892 | 57.087 |

TABLE 9-continued

Induction of IFN-α (pg/ml) by ODN 8954, 5569, and 5570

| ODN | Conc. μg/ml | D521 Mean ± SD | D525 Mean ± SD | D526 Mean ± SD |
|---|---|---|---|---|
| 8954 | 0.03 | 305.626 | 309.581 | 599.971 |
| | 0.06 | 6039.51 | 2028.52 | 4707.01 |
| | 0.125 | 7322.45 | 4669.31 | 5340.21 |
| | 0.25 | 7651.13 | 4641.1 | 5324.55 |
| | 1.0 | 7078.59 | 4679.59 | 5474.94 |
| 5569 | 0.03 | 112.784 | 121.422 | 87.751 |
| | 0.06 | 110.723 | 65.753 | 47.888 |
| | 0.125 | 104.547 | 49.365 | 41.046 |
| | 0.25 | 111.755 | 62.383 | 43.216 |
| | 1.0 | 2247.97 | 115.77 | 1101.58 |
| 5570 | 0.03 | 822.648 | 427.535 | 250.196 |
| | 0.06 | 1858.16 | 1021.18 | 218.201 |
| | 0.125 | 3470.67 | 1657.3 | 477.938 |
| | 0.25 | 5612.53 | 3369.99 | 669.706 |
| | 1.0 | 6798.3 | 3501.59 | 2560.93 |
| Medium | — | 145.436 | 214.212 | 66.853 |
| | — | 245.121 | 218.622 | 0 |

TABLE 10

Induction of IL10 (pg/ml) by ODN 8954, 10101-2, 5569, and 5570

| ODN | Conc. μg/ml | D521 Mean ± SD | D525 Mean ± SD | D526 Mean ± SD |
|---|---|---|---|---|
| 2006 | 0.03 | 151.976 | 112.414 | 485.823 |
| | 0.06 | 384.377 | 218.651 | 898.299 |
| | 0.125 | 404.352 | 242.289 | 991.614 |
| | 0.25 | 357.657 | 247.405 | 1150.94 |
| | 1.0 | 255.344 | 162.444 | 1171.72 |
| 8954 | 0.03 | 7.456 | 6.617 | 6.919 |
| | 0.06 | 5.34 | 5.721 | 19.787 |
| | 0.125 | 10.723 | 2.986 | 35.892 |
| | 0.25 | 15.308 | 13.056 | 67.18 |
| | 1.0 | 48.904 | 30.892 | 230.725 |
| 5569 | 0.03 | 0 | 1.287 | 1.348 |
| | 0.06 | 0 | 0.127 | 4.592 |
| | 0.125 | 18.815 | 3.615 | 62.963 |
| | 0.25 | 105.32 | 30.094 | 350.529 |
| | 1.0 | 256.785 | 136.833 | 1156.07 |
| 5570 | 0.03 | 0 | 0.31 | 5.867 |
| | 0.06 | 6.599 | 7.027 | 29.879 |
| | 0.125 | 98.553 | 38.528 | 455.145 |
| | 0.25 | 259.812 | 107.164 | 1169.46 |
| | 1.0 | 312.189 | 206.126 | 1595.63 |
| Medium | — | 1.755 | 10.543 | 0 |
| | — | 0.29 | 11.192 | 0 |

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, patents and patent publications that are recited in this application are incorporated in their entirety herein by reference.

We claim:

1. An isolated immunostimulatory nucleic acid of 14-100 nucleotides in length having a sequence comprising the formula:

5' $PX_1DCGHX_2$ 3' or 5' $X_1DCGHX_2P$ 3' wherein $X_1$ and $X_2$ are independently any sequence 0 to 10 nucleotides long, D is a nucleotide other than C, C is unmethylated, H is a nucleotide other than G, and P is a GC-rich palindrome containing sequence at least 10 nucleotides long, wherein the immunostimulatory nucleic acid has a completely nuclease-resistant backbone such that each internucleotide linkage is modified, wherein at least one of a), or b) is in the nucleic acid:
 a) P is completely palindromic, H is T, and $X_2$ is selected from the group consisting of CG, CGT, CGTTT, and CGTTTT, wherein when P is 12 nucleotides $X_2$ is not CGTTTT,
 b) P includes at least one inosine.

2. The immunostimulatory nucleic acid of claim 1, wherein the immunostimulatory nucleic acid comprises 5' $X_1DCGHX_2PX_3$ 3', wherein $X_3$ is any sequence 0 to 10 nucleotides long.

3. The immunostimulatory nucleic acid of claim 1, wherein the immunostimulatory nucleic acid comprises 5' $X_1DCGHPX_3$ 3', wherein $X_3$ is any sequence 0 to 10 nucleotides long.

4. The immunostimulatory nucleic acid of claim 1, wherein the immunostimulatory nucleic acid comprises 5' $DCGHX_2PX_3$ 3', wherein $X_3$ is any sequence 0 to 10 nucleotides long.

5. The immunostimulatory nucleic acid of claim 1, wherein the immunostimulatory nucleic acid comprises 5' $TCGHX_2PX_3$ 3', wherein $X_3$ is any sequence 0 to 10 nucleotides long.

6. The immunostimulatory nucleic acid of claim 1, wherein the immunostimulatory nucleic acid comprises 5' $DCGHPX_3$ 3', wherein $X_3$ is any sequence 0 to 10 nucleotides long.

7. The immunostimulatory nucleic acid of claim 1, wherein the immunostimulatory nucleic acid comprises 5' DCGHP 3'.

8. The immunostimulatory nucleic acid of claim 1, wherein D is T.

9. The immunostimulatory nucleic acid of claim 1, wherein H is T.

10. The immunostimulatory nucleic acid of claim 1, wherein P is completely palindromic, H is T, and X2 is selected from the group consisting of CG, CGT, CGTTT, and CGTTTT.

11. The immunostimulatory nucleic acid of claim 10, wherein H is T and $X_2$ is CG.

12. The immunostimulatory nucleic acid of claim 1, wherein H is T and $X_2$ is CGTTT or CGTTTT.

13. An isolated immunostimulatory nucleic acid of 14-100 nucleotides in length having a sequence comprising the formula:

5' $PX_1DCGHX_2$ 3' or 5' $X_1DCGHX_2P$ 3' wherein $X_1$ and $X_2$ are independently any sequence 0 to 10 nucleotides long, D is a nucleotide other than C, C is unmethylated, H is a nucleotide other than G, and P is a GC-rich palindrome containing sequence at least 10 nucleotides long, the immunostimulatory nucleic acid has a nuclease-resistant backbone and wherein:
 H is T and $X_2$ is selected from the group consisting of CG, CGT, CGTT, CGTTT, and CGTTTT, and wherein P includes at least one inosine.

14. The immunostimulatory nucleic acid of claim 1, wherein the immunostimulatory nucleic acid has a phosphorothioate backbone.

15. The immunostimulatory nucleic acid of claim 1, further comprising a poly-T sequence at the 5' end.

16. The immunostimulatory nucleic acid of claim 1, further comprising a poly-T sequence at the 3' end.

17. The immunostimulatory nucleic acid of claim 1, wherein the immunostimulatory nucleic acid is 14-40 nucleotides in length.

18. The immunostimulatory nucleic acid of claim 1, wherein the immunostimulatory nucleic acid is 14-30 nucleotides in length.

19. A pharmaceutical composition, comprising an immunostimulatory nucleic acid of claim 1, and a pharmaceutically acceptable carrier.

20. A vaccine composition of an isolated immunostimulatory nucleic acid of 14-100 nucleotides in length having a sequence comprising the formula:

5' $NX_1DCGHX_2$ 3' or 5' $X_1DCGHX_2N$ 3' wherein $X_1$ and $X_2$ are independently any sequence 0 to 10 nucleotides long, D is a nucleotide other than C, C is unmethylated, H is a nucleotide other than G, and N is a B-cell neutralizing sequence, wherein N begins with CGG and is at least 10 nucleotides long, wherein:
 a) for 5' $NX_1DCGHX_2$ 3'
  H is T and $X_2$ is selected from the group consisting of CG, CGT, CGTT, CGTTT, and CGTTTT,
 b) for 5' $X_1DCGHX_2N$ 3'
  H is T and $X_2$ is selected from the group consisting of CG, CGT, CGTT, and CGTTT,
 and wherein the immunostimulatory nucleic acid has a fully nuclease-resistant backbone, and an antigen.

21. The immunostimulatory nucleic acid of claim 20, wherein N comprises at least four CG dinucleotides and no more than two CCG trinucleotides.

22. The immunostimulatory nucleic acid of claim 20, wherein the immunostimulatory nucleic acid has a phosphorothioate backbone.

23. The immunostimulatory nucleic acid of claim 20, further comprising a poly-T sequence at the 5' end.

24. The immunostimulatory nucleic acid of claim 20, further comprising a poly-T sequence at the 3' end.

25. The immunostimulatory nucleic acid of claim 20, wherein the immunostimulatory nucleic acid is 14-40 nucleotides in length.

26. The immunostimulatory nucleic acid of claim 20, wherein the immunostimulatory nucleic acid is 14-30 nucleotides in length.

27. A pharmaceutical composition, comprising an immunostimulatory nucleic acid of claim 20, and a pharmaceutically acceptable carrier.

28. An immunostimulatory nucleic, wherein the immunostimulatory nucleic acid is TCGTCGTTTTCGGCGGC-CGCCG (SEQ ID NO: 4).

* * * * *

SEQUENCE LISTING

<160> NUMBER OF SEQ ID NOS: 81

<210> SEQ ID NO 1
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 1
tcgtcgtttt cggcgcgcgc cg                                              22

<210> SEQ ID NO 2
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 2
tcgtcgtttt cgtcgcgcgc cg                                              22

<210> SEQ ID NO 3
<211> LENGTH: 22
<212> TYPE: DNA
<213> ORGANISM: Artificial Sequence
<220> FEATURE:
<223> OTHER INFORMATION: Synthetic Oligonucleotide -continued

<400> SEQUENCE: 3
tcgtcgtttt cgtcgcgcgg cg                                          22

<210> SEQ ID NO 4
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 4
tcgtcgtttt cggcggccgc cg                                          22

<210> SEQ ID NO 5
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 5
tcgtcgtttt cggcgcgccg cg                                          22

<210> SEQ ID NO 6
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 6
tcgtcgtttt cggcgccggc cg                                          22

<210> SEQ ID NO 7
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 7
tcgtcgtttt cggcccgcgc gg                                          22

<210> SEQ ID NO 8
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 8
tcgtcgtttt ccgccgccgg gg                                          22

<210> SEQ ID NO 9
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 9
tcgtcgtttt cggggggccc cc                                          22

<210> SEQ ID NO 10
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 10
tcgtcgtttt cccccgggg gg                                              22

<210> SEQ ID NO 11
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 11
tcggcgcgcg ccgtcgtcgt tt                                             22

<210> SEQ ID NO 12
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 12
tcgtcgtttt cggcgcgcgc cgttttt                                        27

<210> SEQ ID NO 13
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 13
tcctgacgtt cggcgcgcgc cg                                             22

<210> SEQ ID NO 14
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: n = 5-methylcytosine
<220> FEATURE:
<221> NAME/KEY: misc_feature
<222> LOCATION: (5)..(5)
<223> OTHER INFORMATION: n = 5-methylcytosine
<220> FEATURE:
<221> NAME/KEY: misc_feature
<222> LOCATION: (11)..(11)
<223> OTHER INFORMATION: n = 5-methylcytosine
<220> FEATURE:
<221> NAME/KEY: misc_feature
<222> LOCATION: (14)..(14)
<223> OTHER INFORMATION: n = 5-methylcytosine
<220> FEATURE:
<221> NAME/KEY: misc_feature
<222> LOCATION: (16)..(16)
<223> OTHER INFORMATION: n = 5-methylcytosine
<220> FEATURE:
<221> NAME/KEY: misc_feature
<222> LOCATION: (18)..(18)
<223> OTHER INFORMATION: n = 5-methylcytosine

```
<220> FEATURE:
<221> NAME/KEY: misc_feature
<222> LOCATION: (20)..(21)
<223> OTHER INFORMATION: n = 5-methylcytosine

<400> SEQUENCE: 14
tngtngtttt nggngngngn ng                                              22

<210> SEQ ID NO 15
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 15
tgctgctttt cggcgcgcgc cg                                              22

<210> SEQ ID NO 16
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 16
tcgtcgtttt cgcgcgcgcg cg                                              22

<210> SEQ ID NO 17
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 17
tcgtcgttgg ttgtcgtttt ggtt                                            24

<210> SEQ ID NO 18
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 18
accatggacg agctgtttcc cctc                                            24

<210> SEQ ID NO 19
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 19
tcctgacgtt cggcgcgcgc cc                                              22

<210> SEQ ID NO 20
<211> LENGTH: 24
<212> TYPE: DNA
<213> ORGANISM: Artificial Sequence
<220> FEATURE:
<223> OTHER INFORMATION: Synthetic Oligonucleotide
```

```
<400> SEQUENCE: 20
tgctgctttt gtgcttttgt gctt                                          24

<210> SEQ ID NO 21
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 21
tcgtcgtttc gtcgttttga cgtt                                          24

<210> SEQ ID NO 22
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 22
tcgcgtgcgt tttgtcgttt tgacgtt                                       27

<210> SEQ ID NO 23
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 23
cggcgcgcgc cg                                                       12

<210> SEQ ID NO 24
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 24
cggcgcgcgc cgcggcgcgc gccg                                          24

<210> SEQ ID NO 25
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 25
cggcgcgcgc cgtcgtcgtt t                                             21

<210> SEQ ID NO 26
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 26
tcggcgcgcg ccgtgctgct tt                                            22
```

```
<210> SEQ ID NO 27
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 27
ccgccgtttt cggcgcgcgc cg                                              22

<210> SEQ ID NO 28
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 28
cggcggccgc cg                                                         12

<210> SEQ ID NO 29
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 29
cgcgcgcgcg cg                                                         12

<210> SEQ ID NO 30
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 30
gcgcgcgcgc gc                                                         12

<210> SEQ ID NO 31
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 31
ccccccgggg gg                                                         12

<210> SEQ ID NO 32
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 32
ggggggcccc cc                                                         12

<210> SEQ ID NO 33
<211> LENGTH: 10
<212> TYPE: DNA
<213> ORGANISM: Artificial Sequence
<220> FEATURE:
<223> OTHER INFORMATION: Synthetic Oligonucleotide
```

```
<400> SEQUENCE: 33 ccccccggggg                                                         10

<210> SEQ ID NO 34
<211> LENGTH: 10
<212> TYPE: DNA
<213> ORGANISM: Artificial Sequence
<220> FEATURE:
<223> OTHER INFORMATION: Synthetic Oligonucleotide

<400> SEQUENCE: 34
gggggccccc                                                          10

<210> SEQ ID NO 35
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 35
ggggtcaacg ttgagggggg                                               20

<210> SEQ ID NO 36
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 36
ggggtcaagc ttgagggggg                                               20

<210> SEQ ID NO 37
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 37
cggcgcgcgc cc                                                       12

<210> SEQ ID NO 38
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 38
gcggcgggcg gcgcgcgccc                                               20

<210> SEQ ID NO 39
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 39
tcgtcgtttt gtcgttttgt cgtt                                          24
```

```
<210> SEQ ID NO 40
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 40
tctcccagcg tgcgccat                                                   18

<210> SEQ ID NO 41
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 41
ataatcgacg ttcaagcaag                                                 20

<210> SEQ ID NO 42
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 42
tctatcgacg ttcaagcaag                                                 20

<210> SEQ ID NO 43
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 43
tcgtcgtttt tgtcgttttt gtcgtt                                          26

<210> SEQ ID NO 44
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 44
tcgtcgtttt gtcgttttg tcgttt                                           26

<210> SEQ ID NO 45
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 45
ttcgtgtttt cgtgttttcg tcgt                                            24

<210> SEQ ID NO 46
<211> LENGTH: 22
<212> TYPE: DNA
<213> ORGANISM: Artificial Sequence
<220> FEATURE:
<223> OTHER INFORMATION: Synthetic Oligonucleotide
```

```
<400> SEQUENCE: 46
tcgtcgttgt cgttttgtcg tt                                              22

<210> SEQ ID NO 47
<211> LENGTH: 10
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: n = inosine
<220> FEATURE:
<221> NAME/KEY: misc_feature
<222> LOCATION: (6)..(6)
<223> OTHER INFORMATION: n = inosine

<400> SEQUENCE: 47 tcntcntttt                                                            10

<210> SEQ ID NO 48
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 48
tgtcgttgtc gttgtcgttg tcgtt                                           25

<210> SEQ ID NO 49
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 49
tcgtcgtttt gacgttttgt cgtt                                            24

<210> SEQ ID NO 50
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 50
tcgtcgtttt gacgttttga cgtt                                            24

<210> SEQ ID NO 51
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: n = 5-methylcytosine
<220> FEATURE:
<221> NAME/KEY: misc_feature
<222> LOCATION: (5)..(5)
<223> OTHER INFORMATION: n = 5-methylcytosine
<220> FEATURE:
<221> NAME/KEY: misc_feature
<222> LOCATION: (13)..(13)
<223> OTHER INFORMATION: n = 5-methylcytosine
```

```
<220> FEATURE:
<221> NAME/KEY: misc_feature
<222> LOCATION: (21)..(21)
<223> OTHER INFORMATION: n = 5-methylcytosine

<400> SEQUENCE: 51
tngtngtttt gtngttttgt ngtt                                              24

<210> SEQ ID NO 52
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 52
tcgtcgtttt tgtcgtttt ttgtcgtt                                            28

<210> SEQ ID NO 53
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 53
tttttttttt tttttttttt tttt                                              24

<210> SEQ ID NO 54
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 54
tcgtcgctgt ctccgcttct tcttgcc                                           27

<210> SEQ ID NO 55
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 55
gggggacgat cgtcggggg                                                    19

<210> SEQ ID NO 56
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 56
ggggtcgacg tcgacgtcga ggggggg                                           27

<210> SEQ ID NO 57
<211> LENGTH: 21
<212> TYPE: DNA
<213> ORGANISM: Artificial Sequence
<220> FEATURE:
<223> OTHER INFORMATION: Synthetic Oligonucleotide
```

```
<400> SEQUENCE: 57 gggggacgacg tcctgggggg g                                            21

<210> SEQ ID NO 58
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 58
tcgtcgtttt cggcggccgc c                                             21

<210> SEQ ID NO 59
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 59
tcgtcgtttt cggccgccgc c                                             21

<210> SEQ ID NO 60
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 60
tcgtcgtttt cggccgccgc cg                                            22

<210> SEQ ID NO 61
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 61
tcgtcgtttt cgccgccgcc g                                             21

<210> SEQ ID NO 62
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 62
tgctgctttt cggcggccgc cg                                            22

<210> SEQ ID NO 63
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: n = inosine
<220> FEATURE:
<221> NAME/KEY: misc_feature
<222> LOCATION: (5)..(5)
<223> OTHER INFORMATION: n = inosine
```

```
<400> SEQUENCE: 63
tngtngtttt cggcggccgc cg                                          22

<210> SEQ ID NO 64
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 64
tcgtcgtttt cggcggccga cg                                          22

<210> SEQ ID NO 65
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 65
tcgtcgtttt cgtcggccgc cg                                          22

<210> SEQ ID NO 66
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 66
tcgtcgtttt cgacggccgc cg                                          22

<210> SEQ ID NO 67
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 67
tcgtcgtttt cggcggccgt cg                                          22

<210> SEQ ID NO 68
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 68
cgacgatcgt cg                                                     12

<210> SEQ ID NO 69
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 69
cgacgtacgt cg                                                     12
```

```
<210> SEQ ID NO 70
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: n = inosine
<220> FEATURE:
<221> NAME/KEY: misc_feature
<222> LOCATION: (6)..(6)
<223> OTHER INFORMATION: n = inosine

<400> SEQUENCE: 70
tcntcntttt cggcggccgc cg                                    22

<210> SEQ ID NO 71
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 71
tcgtcgtttc gacggccgtc g                                     21

<210> SEQ ID NO 72
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 72
tcgtcgtttc gacgatcgtc g                                     21

<210> SEQ ID NO 73
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 73
tcgtcgtttc gacgtacgtc g                                     21

<210> SEQ ID NO 74
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 74
tcgtcgcgac ggccgtcg                                         18

<210> SEQ ID NO 75
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 75
tcgtcgcgac gatcgtcg                                         18
```

```
<210> SEQ ID NO 76
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 76
tcgtcgcgac gtacgtcg                                                 18

<210> SEQ ID NO 77
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 77
tcgttttttt cgacggccgt cg                                            22

<210> SEQ ID NO 78
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 78
tcgttttttt cgacgatcgt cg                                            22

<210> SEQ ID NO 79
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 79
tcgttttttt cgacgtacgt cg                                            22

<210> SEQ ID NO 80
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 80
cgacgttcgt cg                                                       12

<210> SEQ ID NO 81
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 81
cggcgccgtg ccg                                                      13
```